United States Patent
Pasternak et al.

(10) Patent No.: US 10,160,751 B2
(45) Date of Patent: Dec. 25, 2018

(54) INHIBITORS OF THE RENAL OUTER MEDULLARY POTASSIUM CHANNEL

(71) Applicant: Merck Sharp & Dohme Corp., Rahway, NJ (US)

(72) Inventors: Alexander Pasternak, Princeton, NJ (US); Jessica Frie, Harleysville, PA (US); Shuzhi Dong, Plainsboro, NJ (US); Takao Suzuki, Shanghai (CN); Shouning Xu, Shanghai (CN)

(73) Assignee: Merck Sharp & Dohme Corp.

( * ) Notice: Subject to any disclaimer, the term of this patent is extended or adjusted under 35 U.S.C. 154(b) by 0 days.

(21) Appl. No.: 15/545,891

(22) PCT Filed: Feb. 8, 2016

(86) PCT No.: PCT/US2016/016918
§ 371 (c)(1),
(2) Date: Jul. 24, 2017

(87) PCT Pub. No.: WO2016/130444
PCT Pub. Date: Aug. 18, 2016

(65) Prior Publication Data
US 2018/0016263 A1  Jan. 18, 2018

(30) Foreign Application Priority Data

Feb. 12, 2015  (WO) ............... PCT/CN2015/072865

(51) Int. Cl.
*A01N 43/54* (2006.01)
*A61K 31/505* (2006.01)
*C07D 405/14* (2006.01)
*C07D 413/14* (2006.01)
*A61K 31/496* (2006.01)
*A61P 9/00* (2006.01)

(52) U.S. Cl.
CPC .......... *C07D 405/14* (2013.01); *A61K 31/496* (2013.01); *A61P 9/00* (2018.01); *C07D 413/14* (2013.01); *A61K 2300/00* (2013.01)

(58) Field of Classification Search
CPC ........................... A61K 31/513; C07D 413/14
USPC .......................................... 514/269; 544/295
See application file for complete search history.

(56) References Cited

U.S. PATENT DOCUMENTS

| | | |
|---|---|---|
| 1,000,484 A | 8/1911 | Auchu |
| 2,988,551 A | 6/1961 | Morren |
| 3,749,722 A | 7/1973 | Holub |
| 4,806,536 A | 2/1989 | Cross et al. |
| 4,992,547 A | 2/1991 | Berner et al. |
| 5,145,885 A | 9/1992 | Berner et al. |
| 5,215,989 A | 6/1993 | Baldwin et al. |
| 5,614,526 A | 3/1997 | Godel et al. |
| 5,736,546 A | 4/1998 | Kawashima et al. |
| 6,258,813 B1 | 7/2001 | Arlt et al. |
| 8,673,920 B2 | 3/2014 | Pasternak et al. |
| 8,952,166 B2 | 2/2015 | Ding et al. |
| 8,999,990 B2 | 4/2015 | Tang et al. |
| 8,999,991 B2 | 4/2015 | Tang et al. |
| 9,018,211 B2 | 4/2015 | Pasternak et al. |
| 9,056,859 B2 | 6/2015 | Pasternak et al. |
| 9,062,070 B2 | 6/2015 | Pasternak et al. |
| 9,073,882 B2 | 7/2015 | Tang et al. |
| 9,108,947 B2 | 8/2015 | Wals et al. |
| 9,139,585 B2 | 9/2015 | Walsh et al. |
| 9,206,198 B2 | 12/2015 | Ding et al. |
| 9,206,199 B2 | 12/2015 | Pio et al. |
| 9,493,474 B2 | 11/2016 | Walsh et al. |
| 9,527,830 B2 | 12/2016 | Walsh et al. |
| 9,573,961 B2 | 2/2017 | Pasternak et al. |
| 9,604,998 B2 | 3/2017 | Pasternak et al. |
| 9,718,808 B2 | 8/2017 | Biswas et al. |
| 9,751,881 B2 | 9/2017 | Tang et al. |
| 9,765,074 B2 | 9/2017 | Pasternak et al. |

(Continued)

FOREIGN PATENT DOCUMENTS

| | | |
|---|---|---|
| EP | 1939175 A1 | 7/2009 |
| FR | 2673182 | 8/1992 |

(Continued)

OTHER PUBLICATIONS

Bhave,G., Development of a selective small-molecule inhibitor Kir1.1, the renal outer medullary potassium channel, Mol. Pharmacol., 2011, 42-50, 79.
Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.
Fringuelli, F. et al, A Simple Procedure for the Synthesis of Labile Aryl Oxiranes by Epoxidation, Organic Preparations and Procedures Int., 1989, p. 757-761, vol. 21, No. 6.
Hebert, S. C. et al., Molecular Diversity and Regulation of Renal Potassium Channels, Physiol Rev., 2005, p. 319-371, vol. 85.
Ho, K. et al., Cloning and expression of an inwardly rectifying ATP-regulated potassium channel, Nature, 1993, p. 31-38, vol. 362.

(Continued)

*Primary Examiner* — Jeffrey H Murray
(74) *Attorney, Agent, or Firm* — Sarah Hooson; Catherine D. Fitch

(57) ABSTRACT

The present invention provides compounds of Formula (I); and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

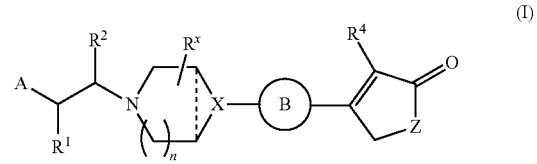

14 Claims, No Drawings

(56) References Cited

U.S. PATENT DOCUMENTS

| | | | |
|---|---|---|---|
| 9,777,002 B2 | 10/2017 | Walsh et al. |
| 9,839,629 B2 | 12/2017 | Dong et al. |
| 9,850,245 B2 | 12/2017 | Pasternak et al. |
| 9,862,720 B2 | 1/2018 | Ding et al. |
| 9,926,317 B2 | 3/2018 | Pasternak et al. |
| 9,951,052 B2 | 4/2018 | Pasternak et al. |
| 2004/0204404 A1 | 10/2004 | Zelle et al. |
| 2005/0215526 A1 | 9/2005 | Hulme et al. |
| 2005/0267121 A1 | 12/2005 | Li et al. |
| 2006/0183739 A1 | 8/2006 | Tsaklakidis et al. |
| 2007/0004750 A1 | 1/2007 | Lorsbach et al. |
| 2007/0072865 A1 | 3/2007 | Fukatsu et al. |
| 2007/0093472 A1 | 4/2007 | Mederski et al. |
| 2007/0275990 A1 | 11/2007 | Ohmoto et al. |
| 2008/0003214 A1 | 1/2008 | Cezanne et al. |
| 2008/0090794 A1 | 4/2008 | Dinsmore et al. |
| 2010/0286123 A1 | 11/2010 | Pasternak et al. |
| 2013/0131042 A1 | 5/2013 | Duffy et al. |
| 2014/0031349 A1 | 1/2014 | Ding et al. |
| 2015/0299198 A1 | 10/2015 | Walsh et al. |

FOREIGN PATENT DOCUMENTS

| | | | |
|---|---|---|---|
| FR | 2673182 A1 | 8/1992 |
| GB | 949088 A | 2/1964 |
| GB | 1575310 A | 9/1980 |
| GB | 2116967 | 7/1986 |
| WO | 9744329 | 11/1997 |
| WO | 0051611 A1 | 9/2000 |
| WO | 0250061 A1 | 6/2002 |
| WO | 2004037817 A1 | 5/2004 |
| WO | 2004046110 A1 | 6/2004 |
| WO | 2005037843 A1 | 4/2005 |
| WO | 2005044797 A1 | 5/2005 |
| WO | 2006034341 A2 | 3/2006 |
| WO | 2006034769 A1 | 4/2006 |
| WO | 2006129199 A1 | 12/2006 |
| WO | 2007075629 A2 | 7/2007 |
| WO | 2008147864 A2 | 12/2008 |
| WO | 2009149508 A1 | 11/2009 |
| WO | 2013066717 A1 | 5/2013 |
| WO | 2014015495 A1 | 1/2014 |
| WO | 2014018764 A1 | 1/2014 |
| WO | 2014085210 A1 | 6/2014 |
| WO | 2014150132 A1 | 9/2014 |
| WO | 2016010802 A1 | 1/2016 |
| WO | 2016060941 A1 | 4/2016 |
| WO | 2016069428 A1 | 5/2016 |
| WO | 2016069430 A1 | 5/2016 |
| WO | 2016122994 A1 | 8/2016 |
| WO | WO2016130444 | 8/2016 |

OTHER PUBLICATIONS

Ji, W. et al., Rare independent mutations in renal salt handling genes contribute to blood pressure variation, Nature Genetics, 2008, p. 592-599, vol. 40, No. 5.

Lerman, Lilach, O. et al., Animal Models of hypertension : An overview, J Lab Clin Med, 2005, p. 160-173, vol. 146, No. 3.

Lewis, L. M., High-throughput screening reveals a small-molecule inhibitor of the Renal Outer Medullary Potassium Channel and Kir7.1, Mol. Phamcol., 2009, 1094-1103, 76.

Lifton, R. P. et al., Molecular Mechanisms of Human Hypertension, Cell, 2001, p. 545-556, vol. 104.

Lorenz, J. N. et al, Impaired Renal NaCl Absorption inMic Lacking the ROMK Potassium Cannel, a Model for Type II Bartter's Syndrome, The Journal of Biological Chemistry, 2002, p. 37871-37880, vol. 277, No. 40.

Lu, M. et al, Absence of Small Conductance K+ Channel (SK) Activity in Apical Membranes of Thick Ascending Limb and Cortical Collectiong Duct in ROMK (Bartter's) Knockout Mice, The Journal of Biological Chemistry, 2002, p. 37881-37887, vol. 277, No. 40.

Molander, G. A. et al., Stereoselective Suzuki-Miyaura Cross-Coupling Reactions of Potassium Alkenyltrifluoroborates with Alkenyl Bromides, J. Org. Chem, 2005, p. 3950-3956, vol. 70.

Nomura, Y. et al, Synthesis and Structure-Activity Relationships of 2-(4-Benzhydryl-1-piperazinyl)-1-phenylethanols as New Calcium Blockers, Chem. Phar. Bull, 1995, p. 241-246, vol. 43, No. 2.

PubChem-CID-72950246, Create Date Mar. 3, 2014, 10 pages.

Reinalter, S. C. et al., Pharmacotyping of hypokalaemic salt-losing tubular disorders, Acta Physiol Scand, 2004, p. 513-521, vol. 181.

Showell, Graham, A. et al, (R)-Sila-venlafaxine: A selective noradrenaline reuptake inhibitor for the treatment of emesis, Bioorganic & Medicinal Chemistry Letters, 2006, pp. 2555-2558, vol. 16.

Shuck, M. E. et al, Cloning and Characterization of Multiple Forms of the Human Kidney ROM-K Potassium Channel, The Journal of Biological Chemistry, 1994, p. 24261-24270, vol. 269, No. 39.

Tobin, M. D. et al., Common Variants in Genes Underlying Monogenic Hypertension and Hypotension and Blood Pressure in the General Population, Hypertension, 2008, p. 1658-1664, vol. 51. No. 6.

Wang, W. et al., Renal potassium channesl: recent developments, Current Opinion in Nephrology and Hypertension, 2004, p. 549-555, vol. 13, No. 5.

ACCF/AHA Practice Guideline, 2009 Focused update incorporated into the ACC/AHA 2005 guidelines for the Diagnosis and Management of Heart Failure in Adults, Circulation, 2009, e391-e436, 119.

Baltzly, R., The preparation of N-mono-substituted and unsymmetrically disubstituted piperazines, J. Am. Chemoc., 1944, 263-266, 66.

Bhave, G., Small-molecule modulators of inward rectifier K+ channels: recent advances and future possibilities, Future Med Chem, 2010, 757-774, 2(5).

Brater et al., Diuretic Therapy, Drug Therapy, 1998, 387-395, 339.

Dorwald, Side reactions in Organic Synthesis: A Guide to Successful Synthesis Design, 2005, Chapter 1.

Felix et al., The Inwardly Rectifying Potassium Channel Kir1.1: Development of Functional Assays to Identify and Characterize Channel Inhibitors, ASSAY and Drug Development Technologies, 2012, 417-431, vol. 10 No. 5.

Frank, Managing hypertension using combination therapy, Am. Fam. Physician, 2008, 1279-1286, 77.

Kulkarni, YD, Possible antifertility agents, part III. Synthesis of 4-(substituted aminomethyl)-5,6,7-trimethoxy phthalid methiodides and 1-N-aminoacetyl-benz [1, 6] diazocin-5-ones (abstract), Biol. Mem., 1987, 141-144, 13.

Lanyi et al., Piperazine-Derivatives II, Res. Lab. of Chinoin-Fabrik Chemisch-Pharma. Prod., 1968, 1431-1435 (English trans.), 18.

Patani, G.A.et al, Bioiososterism: A Rational Approach to Drug Design, Chem. Rev., 1996, 3147-3176, 96.

Sica, D. A., Diuretic use in renal disease, Nature, 2012, 100-109, 8.

INHIBITORS OF THE RENAL OUTER MEDULLARY POTASSIUM CHANNEL

CROSS REFERENCE TO RELATED APPLICATIONS

This application is a U.S. National Phase application under 35 U.S.C. § 371 of PCT Application No. PCT/US2016/016918 filed Feb. 8, 2016, which claims priority from Chinese PCT Application No. PCT/CN2015/072865, filed Feb. 12, 2015.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem. 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K-channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

Since then, other ROMK inhibitors have been described.

The continued discovery of selective small molecule inhibitors of ROMK is needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

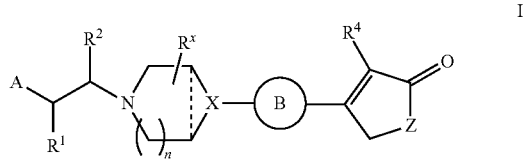

and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION THE INVENTION

The present invention provides compounds of Formula I

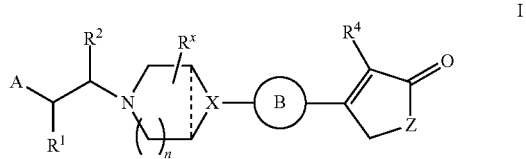

wherein X is N or CR$^b$;
Z is O or CH$_2$;

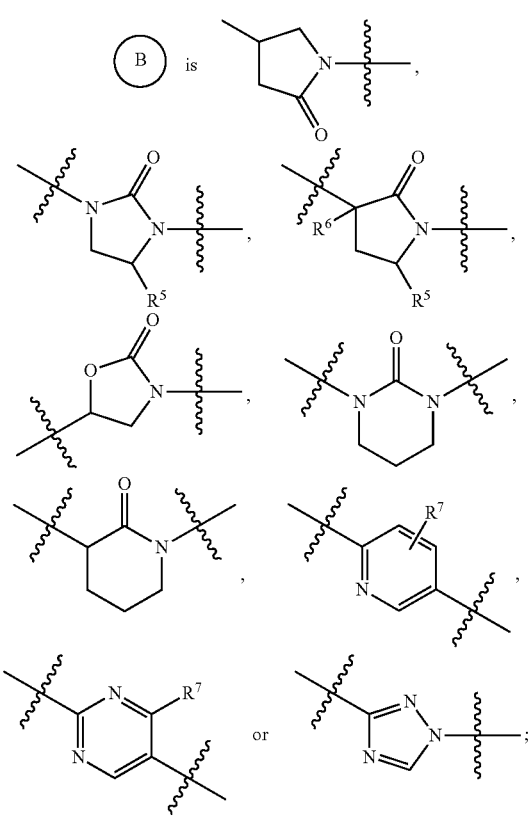

A is or a six-membered aromatic ring containing one or two nitrogen atoms which is optionally substituted with one or two substituents independently selected from the group consisting of tetrazolyl and C$_{1-3}$ alkyl;
R$^1$ is H, OH or O(C$_{1-3}$ alkyl);
R$^2$ is H or C$_{1-3}$ alkyl;
R$^4$ is H or C$_{1-3}$ alkyl;
R$^5$ is H or C$_{1-3}$ alkyl;
R$^6$ is H or C$_{1-3}$ alkyl;
R$^7$ is H, C$_{1-3}$ alkyl or O(C$_{1-3}$ alkyl);
R$^a$ is H or C$_{1-3}$ alkyl;
R$^b$ is H, OH, C$_{1-3}$ alkyl or (C=O)OC$_{1-3}$ alkyl;
R$^x$ is H, halo, C$_{1-3}$ alkyl or O(C$_{1-3}$ alkyl);
n is 0, 1 or 2;
- - - - is an optional bond;
or a pharmaceutically acceptable salt thereof.

The present invention also relates to compounds of Formula Ia:

Ia wherein

B is

A is or a six-membered aromatic ring containing one or two nitrogen atoms which is optionally substituted with one or two substituents independently selected from the group consisting of tetrazolyl and C$_{1-3}$ alkyl;
R$^1$ is H, OH or O(C$_{1-3}$ alkyl);
R$^2$ is H or C$_{1-3}$ alkyl;
R$^4$ is H or C$_{1-3}$ alkyl;
R$^5$ is H or C$_{1-3}$ alkyl;
R$^6$ is H or C$_{1-3}$ alkyl;
R$^a$ is H or C$_{1-3}$ alkyl;
R$^b$ is H, OH, C$_{1-3}$ alkyl or (C=O)OC$_{1-3}$ alkyl;
R$^x$ is H, halo, C$_{1-3}$ alkyl or O(C$_{1-3}$ alkyl);
or a pharmaceutically acceptable salt thereof.

In an embodiment of the invention, X is N. In another embodiment of the invention, N is CR$^b$.

In an embodiment of the invention, Z is O. In another embodiment of the invention, Z is CH$_2$.

In an embodiment of the invention, A is

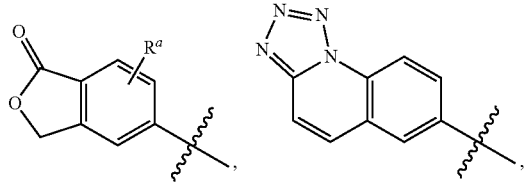

pyridinyl, pyrazinyl or pyridazinyl, wherein said pyridinyl, pyrazinyl or pyridazinyl are optionally substituted with one or two substituents independently selected from the group consisting of tetrazolyl and $C_{1-3}$ alkyl. In a class of the embodiment, A is

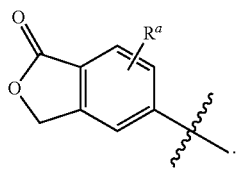

In another class of the embodiment, A is

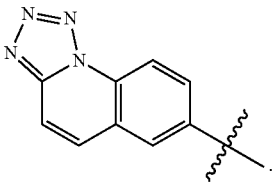 [SMILES: *c1ccc2c(ccc3nnnn32)c1]

In another class of the embodiment, A is pyridinyl, which is optionally substituted with one or two substituents independently selected from the group consisting of tetrazolyl and $C_{1-3}$ alkyl. In another class of the embodiment, A is pyrazinyl, which is optionally substituted with one or two substituents independently selected from the group consisting of tetrazolyl and $C_{1-3}$ alkyl. In another class of the embodiment, A is pyridazinyl, which is optionally substituted with one or two substituents independently selected from the group consisting of tetrazolyl and $C_{1-3}$ alkyl.

In an embodiment of the invention,

B is

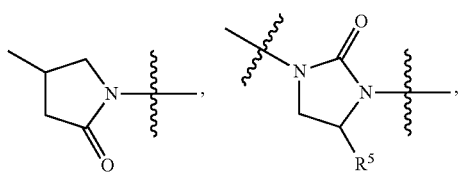

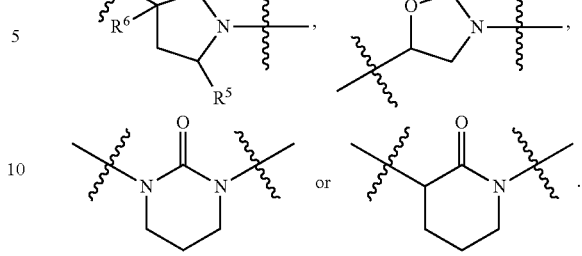

In an embodiment of the invention, $R^1$ is H. In another embodiment of the invention, $R^1$ is OH. In another embodiment of the invention, $R^1$ is $O(C_{1-3}$ alkyl). In a class of the embodiment, $R^1$ is $OCH_3$. In another class of the embodiment, $R^1$ is $OCH_2CH_3$.

In an embodiment of the invention, $R^2$ is H. In another embodiment of the invention, $R^2$ is $C_{1-3}$ alkyl. In a class of the embodiment, $R^2$ is $CH_3$.

In an embodiment of the invention, $R^4$ is H. In another embodiment of the invention, $R^4$ is $C_{1-3}$ alkyl. In a class of the embodiment, $R^4$ is $CH_3$.

In an embodiment of the invention, $R^5$ is H. In another embodiment of the invention, $R^5$ is $C_{1-3}$ alkyl. In a class of the embodiment, $R^5$ is $CH_3$. In another class of the embodiment, $R^5$ is $CH_2C_3$.

In an embodiment of the invention, $R^6$ is H. In another embodiment of the invention, $R^6$ is $C_{1-3}$ alkyl. In a class of the embodiment, $R^6$ is $CH_3$.

In an embodiment of the invention, $R^7$ is H. In another embodiment of the invention, $R^7$ is $O(C_{1-3}$ alkyl). In a class of the embodiment, $R^7$ is $OCH_3$.

In an embodiment of the invention, $R^a$ is H. In another embodiment of the invention, $R^a$ is $C_{1-3}$ alkyl. In a class of the embodiment, $R^1$ is $CH_3$.

In an embodiment of the invention, $R^b$ is H. In another embodiment of the invention, $R^b$ is OH. In another embodiment of the invention, $R^b$ is $C_{1-3}$ alkyl. In another embodiment of the invention, $R^b$ is $(C=O)OC_{1-3}$ alkyl. In a class of the embodiment, $R^b$ is $(C=O)OCH_2CH_3$.

In an embodiment of the invention, $R^x$ is H. In another embodiment of the invention, $R^x$ is halo. In another embodiment of the invention, $R^x$ is $C_{1-3}$ alkyl. In another embodiment of the invention, $R^x$ is $O(C_{1-3}$ alkyl).

In an embodiment of the invention, n is 0. In another embodiment of the invention, n is 1. In another embodiment of the invention, n is 2.

Reference to the preferred classes and subclasses set forth above is meant to include all combinations of particular and preferred groups unless stated otherwise.

Specific embodiments of the present invention include, but are not limited to the compounds identified herein as Examples 1 to 61, or pharmaceutically acceptable salts thereof.

Also included within the scope of the present invention is a pharmaceutical composition which is comprised of a compound of Formula I or Formula Ia as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

It will be understood that, as used herein, the compounds of the instant invention can also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isethionate, lactate, lactobionate, laurate, malate, maleate, mandelate, mesylate, methylbromide, methylnitrate, methyl sulfate, methanesulfonate, mutate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glutamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I or Formula Ia. Unless a specific stereochemistry is indicated, the present invention is meant to comprehend all such isomeric forms of these compounds. Centers of asymmetry that are present in the compounds of Formula I or Formula Ia can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or Formula Ia or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. Unless a particular isomer, salt, solvate (including hydrates) or solvated salt of such racemate, enantiomer, diastereomer or tautomer is indicated, the present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I or Formula Ia are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Reference to the compounds of this invention as those of a specific formula or embodiment, e.g., Formula I or Formula Ia or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I or Formula Ia simultaneously contain acidic and basic groups in the molecule the invention also includes, in addition to the salt forms mentioned, inner salts or betaines (zwitterions). Salts can be obtained from the compounds of Formula I or Formula Ia by customary methods which are known to the person skilled in the art, for example by combination with an organic or inorganic acid or base in a solvent or dispersant, or by anion exchange or cation exchange from other salts. The present invention also includes all salts of the compounds of Formula I or Formula Ia which, owing to low physiological compatibility, are not directly suitable for use in pharmaceuticals but which can be used, for example, as intermediates for chemical reactions or for the preparation of pharmaceutically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$ alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

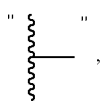

ethyl may be represented by "Et" or CH₂CH₃, propyl may be represented by "Pr" or CH₂CH₂CH₃, butyl may be represented by "Bu" or CH₂CH₂CH₂CH₃, etc. "$C_{1-4}$ alkyl" (or "$C_1$-$C_4$ alkyl") for example, means linear or branched chain alkyl groups, including all isomers, having the specified number of carbon atoms. For example, the structures

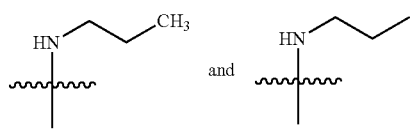

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted, the term "halogen" or "halo" means fluorine, chlorine, bromine or iodine.

"Celite®" (Fluka) diatomite is diatomaceous earth, and can be referred to as "celite".

Except where noted herein, structures containing substituent variables such as variable "R" below:

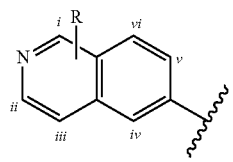

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spire ring systems, where two rings share one atom.

The invention also includes derivatives of the compounds of Formula I or Formula Ia, acting as prodrugs and solvates. Prodrugs, following administration to the patient, are converted in the body by normal metabolic or chemical processes, such as through hydrolysis in the blood, to the compound of Formula I or Formula Ia. Such prodrugs include those that demonstrate enhanced bioavailability, tissue specificity, and/or cellular delivery, to improve drug absorption of the compound of Formula I or Formula Ia. The effect of such prodrugs may result from modification of physicochemical properties such as lipophilicity, molecular weight, charge, and other physicochemical properties that determine the permeation properties of the drug.

The invention also relates to medicaments containing at least one compound of the Formula I or Formula Ia and/or of a pharmaceutically acceptable salt of the compound of the Formula I or Formula Ia and/or an optionally stereoisomeric form of the compound of the Formula I or Formula Ia or a pharmaceutically acceptable salt of the stereoisomeric form of the compound of Formula I or Formula Ia, together with a pharmaceutically suitable and pharmaceutically acceptable vehicle, additive and/or other active substances and auxiliaries.

The compounds of Formula I or Formula Ia according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I or Formula Ia in a ROMK-inhibitory effective amount to a patient in need thereof. This also encompasses the use of the compounds for inhibiting ROMK in a patient comprising administering a compound of Formula I or Formula Ia in a therapeutically effective amount to a patient in need of diueresis, natriuresis or both. The inhibition of ROMK by the compounds of Formula I or Formula Ia can be examined, for example, in the Thallium Flux Assay described below. Moreover, this invention also relates to the use of the compounds of Formula I or Formula Ia or salts thereof to validate in vitro assays, for example but not limited to the Thallium Flux Assay described herein.

The compounds of this invention could be used in a method for causing diuresis, natriuresis or both, comprising administering a compound of Formula I or Formula Ia in a therapeutically effective amount to a patient in need thereof. Therefore, the compounds of Formula I of this invention could be used in methods for treatment of prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I or Formula Ia could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I or Formula Ia may potentially have reduced unintended effects (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an IC50 of 5 µM or less, preferably 1 µM or less, and more particularly 0.25 µM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I or Formula Ia. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, particularly 0.001 to 30 mg/kg, in particular 0.001 to 10 mg/kg (in each case mg per kg of bodyweight) is appropriate for administration to an adult weighing approximately 75 kg in order to obtain the desired results. The daily dose is particularly administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, particularly mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I or Formula Ia and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I or Formula Ia with a pharmaceutically acceptable carrier. Also encompassed is the pharmaceutical composition which is made by combining a compound of Formula I or Formula Ia with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I or Formula Ia and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I or Formula Ia inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I or Formula Ia can also be employed as intermediates for the preparation of other pharmaceutically active compounds.

One or more additional pharmacologically active agents may be administered in combination with a compound of Formula I or Formula Ia. The additional active agent (or agents) is intended to mean a medicinal compound that is different from the compound of Formula I or Formula Ia, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I or Formula Ia in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®)), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); angiotensin receptor neprilysin inhibitors (e.g., LCZ696); aldosterone antagonists; aldosterone synthase inhibitors; renin inhibitors (e.g., enalkrein; RO 42-5892; A 65317; CP 80794; ES 1005; ES 8891; SQ 34017; aliskiren (2(S),4(S),5(S),7(S)—N-(2-carbamoyl-2-methyl-propyl)-5-amino-4-hydroxy-2,7-diisopropyl-8-[4-methoxy-3-(3-methoxypropoxy)-phenyl]-octanamid hemifumarate), SPP600, SPP630 and SPP635); endothelin receptor antagonists; vasodilators (e.g. nitroprusside); calcium channel blockers (e.g., amlodipine, nifedipine, verapamil, diltiazem, felodipine, gallapamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone prodrug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), SGLT2 inhibitors (e.g., canagliflozin, dapagliflozin, ipragliflozin, empagliflozin, tofogliflozin, luseogliflozin/TS-071, ertugliflozin, and remogliflozin), dipeptidyl peptidase inhibitors, (e.g., sitagliptin (JANUVIA®), omarigliptin, alogliptin, vildagliptin, saxagliptin, linagliptin dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); a stimulator of soluble guanylate cyclase (sGC), such as riociguat, vericiguat; or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I or Formula Ia, or the active agent(s) therein could be used in a fixed dose drug combination including a compound of Formula I or Formula Ia.

EXAMPLES

Several methods for preparing the compounds of this invention are described in the following Schemes and Examples. Starting materials and intermediates are purchased, made from known procedures, or as otherwise illustrated. Some frequently applied routes to the compounds of Formula I or Formula Ia are also described by the Schemes as follows. In some cases the order of carrying out the steps of reaction schemes may be varied to facilitate the reaction or to avoid unwanted reaction products. The "R" substituents in the Schemes correspond to the substituents defined in Formula I or Formula Ia at the same positions on the structures.

Compound 1.3, which is substituted at the benzylic position with an OH group, can be prepared following the sequence detailed in Scheme 1. Coupling of epoxide 1.1 to amines 1.2 at elevated temperatures leads to the formation of alcohols 1.3 (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol, 2-propanol and toluene. Amines 1.2 may be free bases, or they may be salts, in which case a base such as triethylamine or N;N-diisopropylethylamine may be added. Note that when enantiomerically pure chiral epoxides are employed (such as (R)-1.1 in Scheme 1) epoxide opening occurs with retention of stereochemistry in the benzylic position and individual isomer (R)-1.3 may be obtained (and if the (S)-epoxide is employed the alcohol produced will have the opposite stereochemistry to that shown). Alternatively, chiral HPLC separation of enantiomers or diastereomers of 1.3 may be performed to provide single enantiomers or diastereomers.

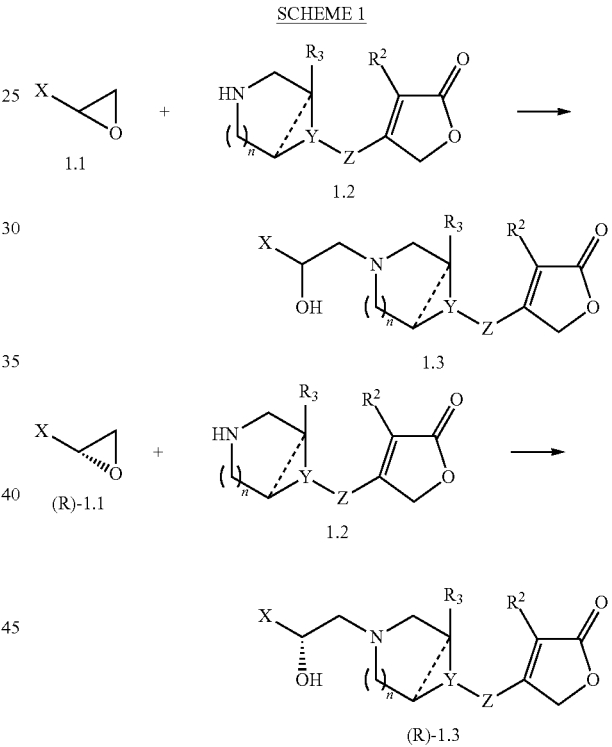

Compounds of formula. 2.3 can be prepared by the sequence detailed in Scheme 2. Aldehydes or ketones 2.1 may be used in reductive alkylation reactions of amines 1.2 to afford ROMK inhibitors of the formula 2.3 by using various conditions (for example using sodium cyanoborohydride, sodium triacetoxy borohydride, or titanium tetra-isopropoxide, followed by sodium borohydride or sodium cyanoborohydride). Alternatively, compounds of formula 2.3 can be prepared by addition of amine 1.2 to an olefin of type 2.2 in the presence of a catalyst Rh(COD)$_2$BF$_4$/DPEP-hos. Under this condition, the olefins of type 2.2 may be required to be activated by a nitrogen atom or other electron-withdrawing group at the position ortho to the double bond on the aromatic ring.

SCHEME 2

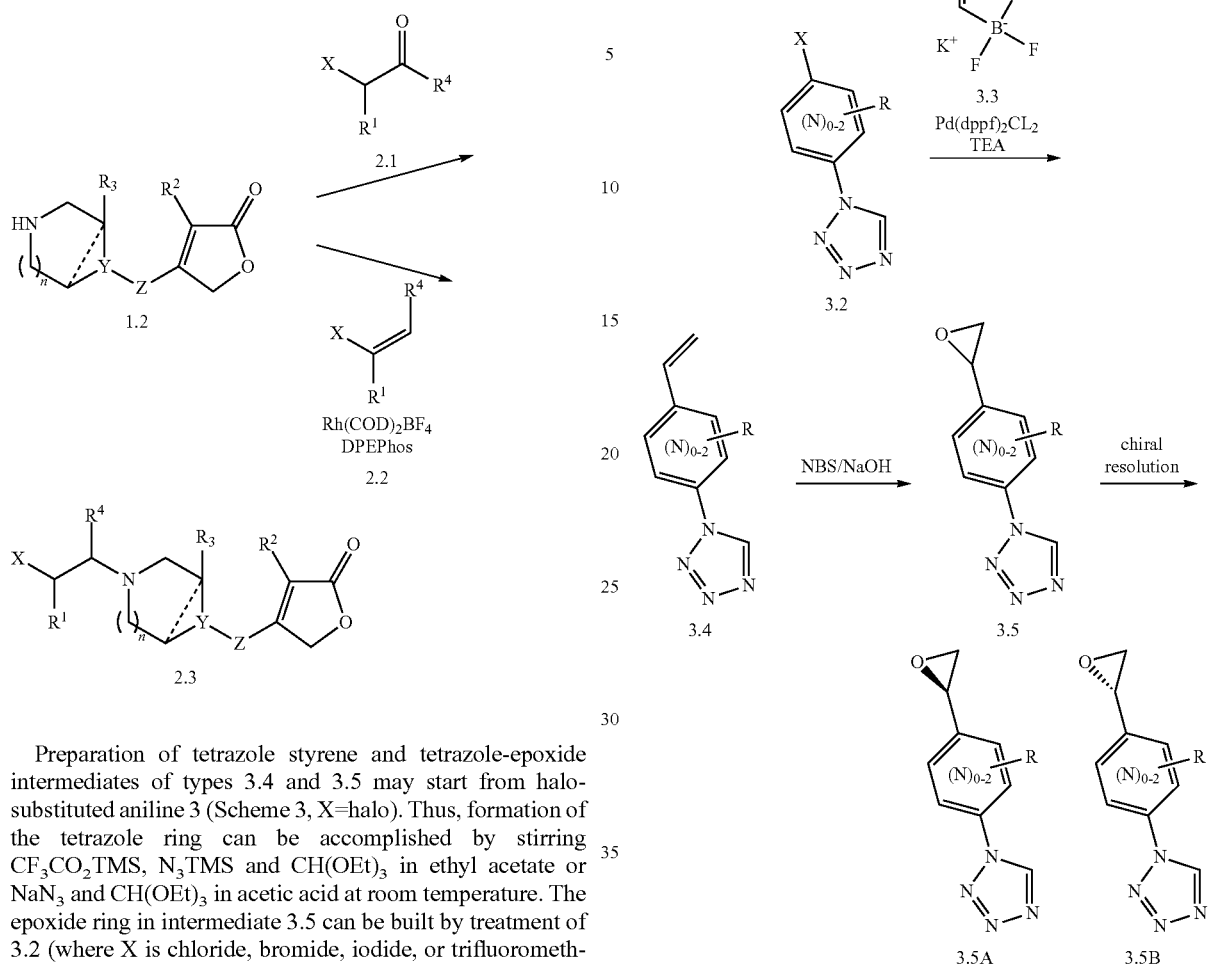

Preparation of tetrazole styrene and tetrazole-epoxide intermediates of types 3.4 and 3.5 may start from halo-substituted aniline 3 (Scheme 3, X=halo). Thus, formation of the tetrazole ring can be accomplished by stirring CF$_3$CO$_2$TMS, N$_3$TMS and CH(OEt)$_3$ in ethyl acetate or NaN$_3$ and CH(OEt)$_3$ in acetic acid at room temperature. The epoxide ring in intermediate 3.5 can be built by treatment of 3.2 (where X is chloride, bromide, iodide, or trifluoromethanesulfonate) with potassium vinyl trifluoroborate (Molander, G.; Luciana, A. Journal of Organic Chemistry, 2005, 70(10), 3950-3956) under palladium catalyzed coupling conditions followed by epoxidation of the formed styrene with NBS/NaOH. The intermediate styrene 3.4 can be used to prepare ROMK inhibitors in place of 2.2 according to Scheme 2. Other methods for formation of styrene may be employed, for example, using vinylstannane reagents and palladium catalysis, and other methods for epoxidation of the styrene may be used, for rexample, mCPBA. The racemic epoxides of formula 3.5 can be resolved under chiral HPLC chromatography conditions to afford its enantiomers (R)-3.5 and (S)-3.5, which can be used in place of 1.1 according to Scheme 1.

SCHEME 3

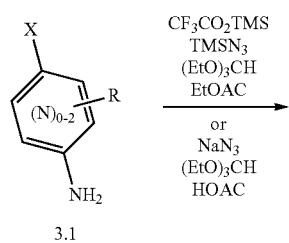

Aldehydes 4.3 can be prepared in numerous ways, including as described in Scheme 4. Aldehyde 4.3 can be prepared by hydrogenation of intermediate epoxides 3.5 followed by oxidation with Dess-Martin periodinane. Aldehydes 4.3 can be used in place of intermediates 2.1 in Scheme 2 to prepare ROMK inhibitors.

SCHEME 4

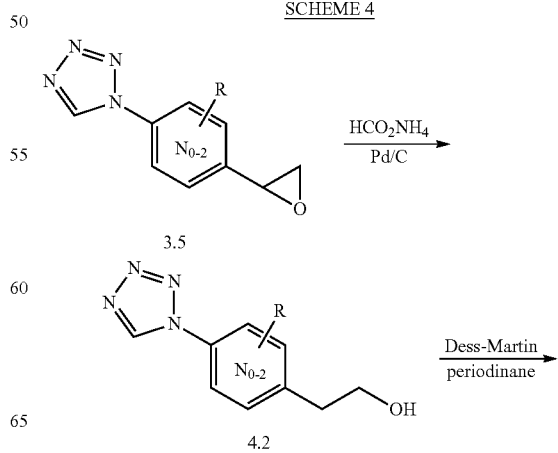

-continued

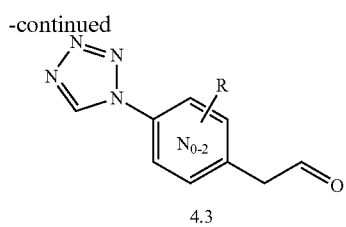
4.3

The epoxides 5.3 (and single enatiomers (R)-5.3 and (S)-5.3) can be prepared following the method detailed in Scheme 5. Treatment of 5.1 (where X is chloride, bromide, iodide, or trifluoromethane sulfonate) with commercially available potassium vinyl trifluoroborate (Molander, G.; Luciana, A. Journal of Organic Chemistry, 2005, 70(10), 3950-3956) under palladium catalyzed coupling conditions with an appropriate phosphine ligand gives rise to styrene 5.2 (Molander, G.; Brown, A. Journal of Organic Chemistry, 2006, 71(26), 9681-9686). Alternatively, other methods may be employed, for example, using vinylstannane reagents and palladium catalysis. The resulting styrenes 5 can be converted to the corresponding epoxides 5.3 under various epoxidation conditions, for example, with mCPBA. (Fringuelli, et al. Organic Preparations and Procedures International, 1989, 21(6), 757-761). The racemic epoxide 5.3 can be resolved under chiral HPLC chromatography conditions to afford its enantiomers (R)-5.3 and (S)-5.3, which can be used in place of 1.1 according to Scheme 1.

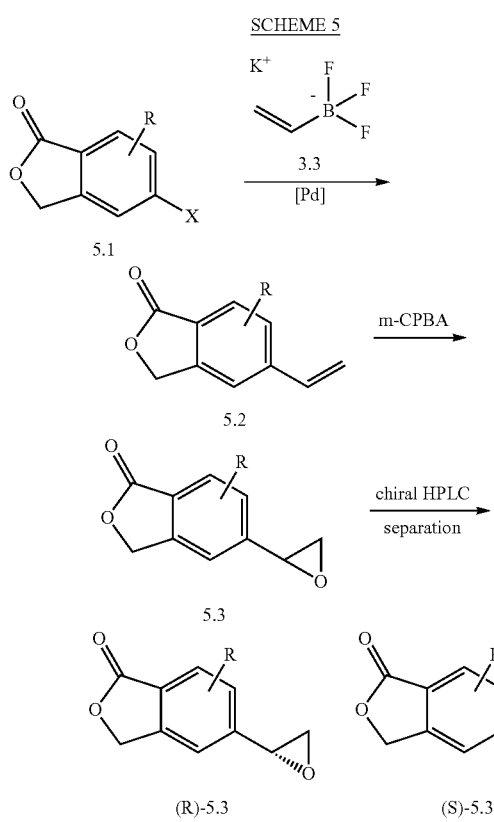

Alternatively, enantiopure epoxides (R)-5.3 or (S)-5.3 can be prepared as shown in Scheme 6. Treatment of 5.1 (where X is bromide, iodide, or trifluoromethane sulfonate) with commercially available vinyl butylether 6.1 under palladium catalyzed conditions with a suitable ligand (for example Pd(OAc)$_2$, DPPP) can provide the enol ethers 6.2. Enol ethers may be prepared using other methods known to the chemist. Treatment of the resulting enol ethers 6.2 with NBS or other similar reagents affords the corresponding bromomethyl ketones 6.3. These can be subjected to a variety of asymmetric ketone reduction conditions, for example with an enzyme that can affect such a transformation with high enantioselectivity. Subsequent treatment with a base such as triethylamine leads to cyclization, affording the enantioenriched epoxides (R)-5.3 or (S)-5.3 (depending upon the asymmetric reducing agent).

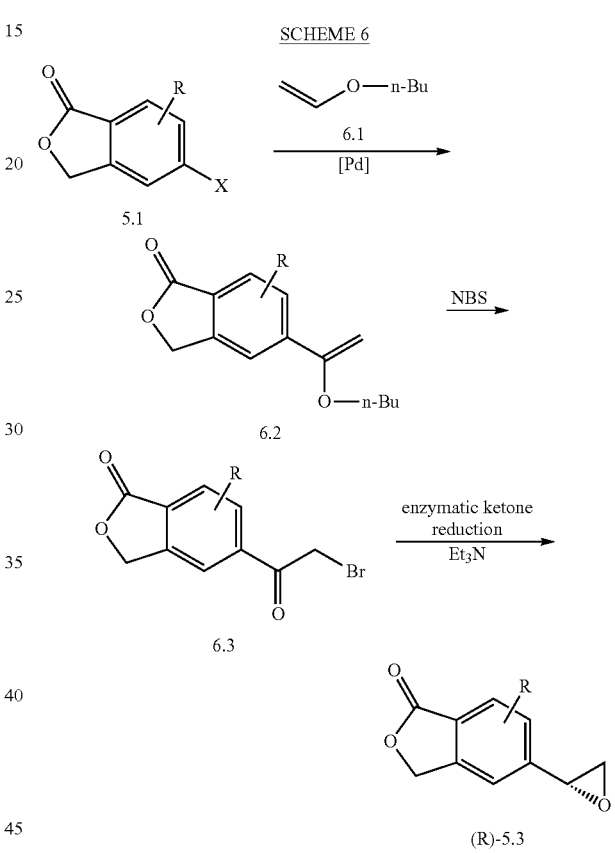

Aldehydes 7.2 may be prepared in numerous ways, with one approach described in Scheme 7. Treatment of 5.1 (where X is bromide, iodide, or trifluoromethane sulfonate) with allyltributylstannane in the presence of palladium catalyst affords the allyl product 7.1. Oxidation, for example with ozone, followed by reduction of the ozonide with dimethyl sulfide, provides aldehydes 7.2 which can be used in place of 2.1 to prepare ROMK inhibitors according to Scheme 2.

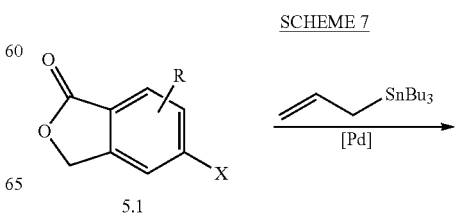

-continued

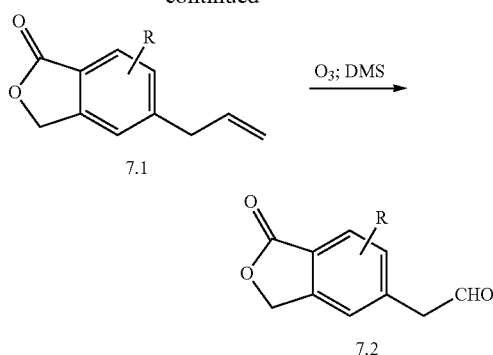

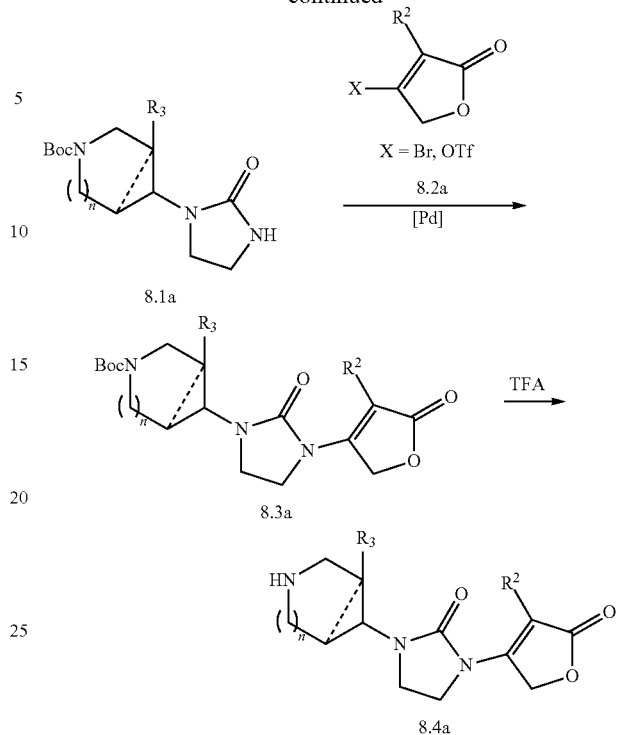

Heterocyclic furanones 8.4 can be prepared as described in Scheme 8. Heterocycles such as 8.1, where an amine is protected as appropriate (Greene, T.; Wuts, P. G. M. *protective Groups in organic Synthesis*, John Wiley and Sons, Inc., New York, N.Y. 1991), and where Z represents a heterocycle possessing an N—H group, can be coupled to furanone triflates or bromides 8.2 using a palladium catalyst and ligand, for example palladium acetate and 4,5-Bis (diphenylphosphino)-9,9-dimethylxanthene. Heterocycles such as 8.1, where an amine is protected as appropriate, and where Z represents a heterocycle possessing an N—H group are known or can prepared as described in the experimental section below. One example is represented by 8.1a, wherein Z is an imidazolinone heterocycle, which is shown to proceed through the steps of SCHEME 8. 4-Bromofuran-2 (5H)-one is commercially available; other furanones 8.2 can be prepared as described in the examples below. Intermediates 8.3 are converted to spirocyclic aminofuranones 8.4 by removal of the protective group, for example, tert-butoxycarbonyl can be removed with TFA or HCl. The heterocyclic furanones 8.4 can be used in place of Intermediate 1.2 in Schemes 1 and 2 above to afford ROMK inhibitors.

SCHEME 8

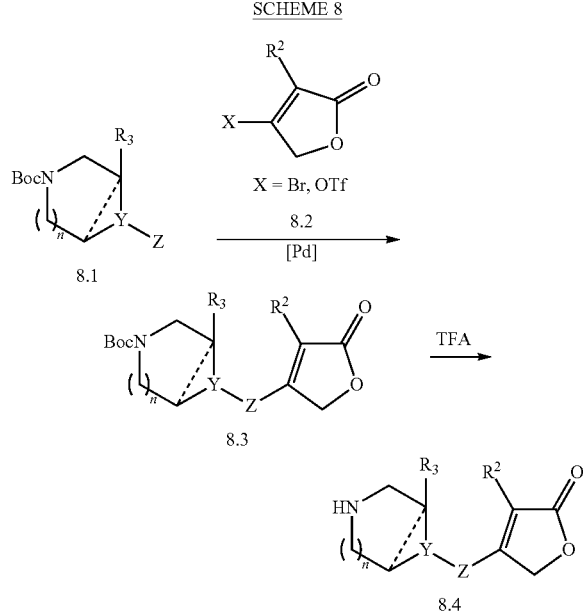

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated. The following examples are provided for the purpose of further illustration only and are not intended to be limitations on the disclosed invention.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage.

Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz).

Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of Chiralpak AS, Chiralpak AD, Chiralcel OD, Ciralcel IA, or Chiralcel OJ columns (20×250 mm) (Daicel Chemical industries, Ltd.) with desired isocratic solvent systems identified on chiral analytical chromatography or by supercritical fluid (SFC) conditions. Alternatively, chiral preparative chromatography was by supercritical fluid (SFC) conditions using one of Chiralpak AS, Chiralpak AD-H, Chiralcel OD-H, Chiralpak IC, or Chiralcel OJ-H columns (250×21.2 mm) (Daicel Chemical Industries, Ltd.). Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Flash chromatography was carried out on silica gel (230-400 mesh). NMR spectra were obtained in $CDCl_3$ solution unless otherwise noted. Coupling constants (J) are in hertz (Hz).

Abbreviations used herein include: —C(O)CH$_3$ (Ac); —OC(O)CH$_3$ (OAc); ethyl acetate (EtOAc), benzyloxycarbonyl (Cbz); dibenzylideneacetone (dba); 11-chloroethylchloroformate (ACE-Cl); phenyl (Ph); dichloromethane (DCM), starting material (SM), diethyl ether (ether or $Et_2O$), trifluoroacetic acid (TFA), triethylamine (TEA), 1,8-Diazabicyclo[5.4.0]undec-7-ene (DBU); Diethanolamine (DEA); N,N-diisopropylethylamine (DIEA, Hunig's base, DIPEA), dimethylsulfide (DMS); 1-ethyl-3-(3-dimethylaminopropyl), carbodiimide (EDC, EDAC, or EDCI); ethylene glycol tetraacetic acid (EGTA); 2-(7-Aza-1H-benzotriazole-1-yl)-1,1,3,3-tetramethyluronium hexafluorophosphate (HATU), (4-(2-hydroxyethyl)-1-piperazineethanesulfonic acid (HEPES); 1-Hydroxybenzotriazole hydrate (HOBt), hexane (Hex); methyl tert-butyl ether (MTBE), Cyclopentyl methyl ether (CPME), 1,3-Bis(diphenylphosphino)propane (DPPP), 2-Dicyclohexylphosphino-2',4',6'-triisopropylbiphenyl (X-Phos), 1,2-dichloroethane (DCE), methanol (MeOH); N-bromo succinimide (NBS), N-chlorosuccinimide (NCS); N-iodosuccinimide (NIS), lithium diisopropylamide (LDA), tetrahydrofuran (THF), Diethylaminosulfur trifluoride (DAST); dimethylsulfoxide (DMSO), isopropanol (IPA), t-butyloxycarbonyl (Boc or BOC), di-t-butyl dicarbonate ($BOC_2O$, $Boc_2O$), acetic acid (AcOH; HOAc), N;N-dimethylformamide (DMF), 4-dimethylaminopyridine (DMAP), dimethylacetamide (DMA; DMAC); Lithium bis(trimethylsilyl)amide (LiHMDS); 3-chloroperoxybenzoic acid (mCPBA); nicotinamide adenine dinucleotide phosphate (NADP), petroleum ether (PE), lithium aluminum hydride (LAH), di-isopropylamine (DIPA), Carbonyldiimidazole (CDI), p-toluenesulfonic acid (TsOH), p-toluene-$SO_2$— (tosyl or Ts), methane sulfonyl chloride or mesyl chloride (Ms-Cl), methanesulfonic acid (MsOH), $CH_3SO_2$- (mesyl or Ms), dimethoxyethane (DME), 1,1'-bis(diphenylphosphino)ferrocene (dppf, DPPF); Pd(dppf)$Cl_2$ or $PdCl_2$(dppt) is 1,1'-Bis(diphenylphosphino)ferrocene] dichloropalladium(II) which may be complexed with $CH_2Cl_2$, (Oxydi-2,1-phenylene)bis(diphenylphosphine) (DPEphos); hexamethylphosphoramide (HMPA); isopropyl acetate (IPAc); N-methylmorpholine-N-oxide (NMO); tetrakis(triphenylphosphine)palladium (Pd(PPh$_3$)$_4$); tris(dibenzylidineacetone)dipalladium (Pd$_2$(dba)$_3$); Diethylaminodifluorosulfinium tetrafluoroborate (XtalFluor-E); 4,5-Bis(diphenylphosphino)-9,9-dimethylxanthene Xantphos); N,N,N',N'-Tetramethylethylenediamine (TMEDA); Trimethylsilyl (TMS); [1,4-Bis(diphenylphosphino)butane](1,5-cyclooctadiene)rhodium(I) tetrafluoroborate (Rh(COD)BF$_4$); round-bottom flask (RB or RBF); aqueous (aq); saturated aqueous (sat'd), saturated aqueous sodium chloride solution (brine); medium pressure liquid chromatography (MPLC), high pressure liquid chromatography (HPLC), flash chromatography (FC); liquid chromatography (LC), supercritical fluid chromatography (SFC); thin layer chromatography (TLC), mass spectrum (ms or MS); liquid chromatography-mass spectrometry (LC-MS or LC/MS), microwave (MW), column volume (CV), room temperature (rt, r.t. or RT), hour(s) (h or hr), minute(s) (min), retention time ($R_t$); gram(s) (g); milligram(s) (mg); milliliter(s) (mL); microliter(s) (µL); millimole (mmol). Celite is a trademark name for diatomaceous earth, and Solka Floc is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

Intermediate 1

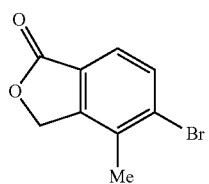 [SMILES: Cc1c(Br)ccc2c1COC2=O]

5-bromo-4-methyl-2-benzofuran-1(3H)-one

Step A: (3-bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol. $^1$H NMR (500 MHz, CDCl$_3$) δ7.76 (d, J=8.0 Hz, 1H), 7.63 (d, J=8.0 Hz, 1H), 5.30 (s, 2H), 2.42 (s, 3H).

Step B: 5-bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a celite pad, washed with EtOAc, adsorbed onto silica and purified by silica gel chromatography to afford title compound. $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

Intermediate 2

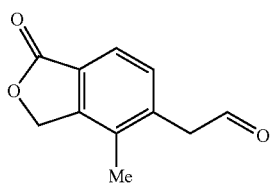 [SMILES: Cc1c(CC=O)ccc2c1COC2=O]

4-Methyl-1-oxo-1,3-dihydro-2-benzofuran-5-yl)acetaldehyde

Step A: 4-Methyl-5-prop-2-en-1-yl-2-benzofuran-1(3H)-one

To a flask charged with 5-bromo-4-methyl-2-benzofuran-1(3H)-one (320 mg, 1.409 mmol) and a stir bar was added allyl tri-n-butyltin (0.655 mL, 2.11 mmol), Pd(PPh$_3$)$_4$ (244 mg, 0.211 mmol), lithium chloride (179 mg, 4.23 mmol), and toluene (15 mL). The reaction was purged with nitrogen 2 times then was heated at reflux for 4 hours. The product was separated by silica gel chromatography to give 4-methyl-5-prop-2-en-1-yl-2-benzofuran-1(3H)-one.

Step B: (4-Methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford the title compound, $^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

Intermediate 3

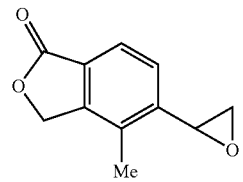 [SMILES: Cc1c(C2CO2)ccc2c1COC2=O]

4-methyl-5-oxiran-2-yl-2-benzofuran-1(3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmol), PdCl$_2$(dppf)-CH$_2$Cl$_2$Adduct (182 mg, 0.223 mmmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield 5-ethenyl-4-methyl-2-benzofuran-1(3H)-one. $^1$H-NMR (500 MHz, CDCl$_3$): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H); LC-MS: M+1=175;

Step B: 4-methyl-5-oxiran-2-yl-2-benzofuran-1(31H)-one 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous $Na_2S_2O_3$, $NaHCO_3$, and brine. The organic layer was dried over $Na_2SO_4$, filtered, and evaporated to dryness. The crude material was purified by MPLC chromatography through 120 g Redi-sep column eluting with 0-80% EtOAc/hexane solvent system to yield target 4-methyl-5-oxiran-2-yl-2-benzofuran-1(3H)-one. $^1$H-NMR (500 MHz, $CDCl_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H). LC-MS: M+1=101.

Intermediates 3A and 3B (Method 1)

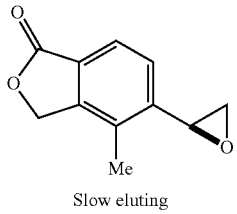

3A

Slow eluting

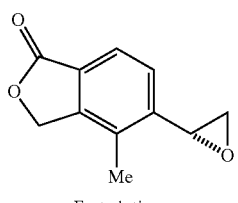

3B

Fast eluting

3A: 4-methyl-5-[(2S)-oxiran-2-yl]-2-benzofuran-1(3H)-one

3B: 4-methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/$CO_2$, flow rate 200 mL/min, 100 bar, 25° C. 500 ul Injections were spaced every 2.12 mins. The fast epoxide (4-methyl-5-[(2R)-oxiran-2-yl]-2-benzofuran-1(3H)-one, 3B) eluted first, and the slow epoxide (4-methyl-5-[(2S)-oxiran-2-yl]-2-benzofuran-1(3H)-one, 3A) eluted second.

Alternatively, the resolution could also be achieved using a mobile phase of 8% MeOH/98% $CO_2$ with a flow rate of 100 mL/min. In that case the sample was prepared by dissolving in methanol, 20 mg/mL, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 3B and by Mosher ester and Trost ester HNMR analysis of esters made starting from 3B. Both epoxide isomers find utility in the present invention.

Intermediate 3B (Method 2)

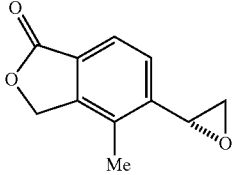 [SMILES: Cc1c([C@@H]2CO2)ccc2c1COC2=O]

4-methyl-5-[(2R)-oxiran-2-yl]-2-benzofuran-1(3H)-one

Step A: 3-hydroxymethyl-2-methyl phenol

To a 5 L 3 neck RB equipped with overhead stirrer was charged $NaBH_4$ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which $BF_3$-$OEt_2$ (321 mL, 2.53 mol) was added slowly over 1.5 hours. The slurry was aged at 10° C.-15° C. for 2 h then assayed for reaction completion. The slurry was cooled to <10° C. and quenched with 931 mL MeOH slowly over 1.5 h (gas evolution). The resulting slurry was aged overnight at RT. The batch was cooled to <10° C. then quenched with 1 NHCl (1.5 L) to get a homogeneous solution (pH solution~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol. $^1$H-NMR (400 MHz, DMSO-$d_6$): δ9.11 (s, 1H), 6.95 (t, J=7.8 Hz, 1H), 6.82 (d, J=7.4 Hz, 1H), 6.71 (d, J=7.8 Hz, 1H), 4.93 (t, J=5.5 Hz, 1H) 4.44 (d, J=5.5 Hz, 2H), 2.06 (s, 3H).

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane: MTBE (500 mL), followed by heptane (500 mL). The solid was dried under vacuum, providing 4-bromo-3-hydroxymethyl-2-methyl phenol. $^1$H NMR (400 MHz, DMSO-d$_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H)

Step C:
5-Hydroxy-4-methyl-3H-isobenzofuran-1-one

To a 2 L 3 neck flask equipped with overhead stirrer, N$_2$ inlet, and condenser were charged 4-bromo-3-hydroxymethyl-2-methyl phenol (100 g, 461 mmol), CuCN (83.0 g, 921 mmol), and DMF (500 mL). The solution was sparged with N$_2$ for 15 min then heated to 145° C. to obtain a homogeneous solution. The solution was aged at 145° C. for 2 h, then the reaction mixture was cooled to 95° C. 41.5 mL water was added (sparged with N$_2$), and the reaction aged for 20 h. The reaction was cooled to RT then the solids filtered through solka flok and the cake washed with 50 mL DMF. To a 3 L flask containing 1 L EtOAc was added the DMF filtrate. A precipitate coating formed in bottom of flask. The DMF/EtOAc suspension was filtered through solka flak and the cake was washed with 250 mL EtOAc. The resulting filtrate was washed with 5% brine solution 3×500 mL). The aqueous layers were extracted with 500 mL EtOAc and the combined organics were dried over MgSO4, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one. $^1$H NMR (400 MHz, DMSO-d$_6$): δ 10.52 (s, 1H), 7.51 (d, J=8.3 Hz, 1H), 6.99 (d, J=8.3 Hz, 1H), 5.28 (s, 2H), 2.07 (s, 3H).

Step D:
4-methyl-1-oxo-1,3-dihydroisobenzofuran-5-yl trifluoromethanesulfonate

5-Hydroxy-4-methyl-3-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), then stirred with DARCO® KB (activated carbon, 25 g) for 15 min. The biphasic mixture was filtered over Solka floc, washing with additional dichloromethane, and transferred to a separator)/funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, the solid washed with heptane and dried under vacuum and nitrogen, providing trifluoromethanesulfonic acid 4-methyl-1-oxo-1,3-dihydro-isobenzofuran-5-yl ester. $^1$H NMR (400 MHz, CDCl$_3$): δ 7.87 (d, J=8.4 Hz, 1H), 7.47 (d, J=8.4 Hz, 1H), 5.32 (s, 2H), 2.41 (s, 3H)

Step E: 5-(1-Butoxy-vinyl)-4-methyl-3H-isobenzofuran-1-one

To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol)) then Et$_3$N (35.6 mL, 255 mmol). The solution was sparged with N$_2$ for 20 min. To the solution was added Pd(OAc)$_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% NH$_4$Cl (2×315 mL), 10% brine (2×315 mL), dried over MgSO$_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one. $^1$H NMR (400 MHz, DMSO-d$_6$): δ 7.67 (d, J=7.7 Hz, 1H), 7.48 (d, J=7.7 Hz, 1H), 5.42 (s 2H), 4.54 (d, J=2.3 Hz, 1.14), 4.27 (d J=2.3 Hz, 1H), 3.85 (t, J=6.4 Hz, 2H), 2.27 (s, 3H), 1.71-1.64 (m 2H), 1.46-1.37 (m, 2H), 0.92 (t, J=7.4 Hz, 3H)

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portion-wise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2. THF:water (15° C.): 150 mL displacement wash followed by 100 mL slurry wash. The solids were dried under vacuum at RT to provide 5-(2-bromo-acetyl)-4-methyl-3H-isobenzofuran-1-one. $^1$H NMR (400 MHz, DMSO-d$_6$): δ 7.99 (d, J=7.8 Hz, 1H), 7.82 (d, J=7.8 Hz, 1H), 5.49 (s, 2H), 4.92. (s, 2H), 2.33 (s, 3H)

Step G: 4-methyl-5-[(2R)-oxiran-2-yl]-2-benzofuran-1(3H)-one 5-(2-Bromo-acetyl)-4-methyl-3H-isobenzofuran-1-one (48.8 g., 181 mmol) was charged to a 5 L 3 neck round bottom equipped with overhead stirrer, thermocouple, and heating mantle. 2-Propanol (1.22 L) was added, followed by 610 mL of pH 70.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 mL IPAc (thick slurry). Hexanes were added (400 mL) and the suspension aged at RT then filtered and washed w/5:1 Hexanes:IPAc solution (150 mL). The crystalline solids were dried under vacuum at RT to provide 4-methyl-5-[(2R)-oxiran-2-yl]-2-benzofuran-1(3H)-one. $^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H).

Intermediate 4

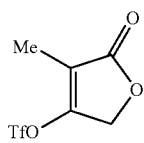

4-methyl-5-oxo-2,5-dihydrofuran-3-yl trifluoromethanesulfonate

Step A: ethyl 4-bromo-2-methyl-3-oxobutanoate

To the solution of ethyl 2-methyl-3-oxobutanoate (5.05 g, 35.0 mmol) in water (10 mL) at 0° C. was added bromine (1.805 mL, 35.0 mmol) dropwise over 2 h. The resulting solution was stirred at rt for 16 h. The reaction mixture was extracted with ethyl acetate, the organic phase was dried over sodium sulfate, and concentrated to give ethyl 4-bromo-2-methyl-3-oxobutanoate. $^1$H NMR (500 MHz, CDCl$_3$), δ 4.322-4.274 (m, 2H), 2.455 (s, 2H), 1.991 (s, 3H), 1.337-1.309 (t, 3H).

Step B: 4-hydroxy-3-methylfuran-2(5H)-one

Ethyl 4-bromo-2-methyl-3-oxobutanoate (7.81 g, 35 mmol) was treated with hydrogen bromide (0.040 mL, 48%, 0.35 mmol) and the mixture was heated at 100° C. for 6 h. The precipitate was collected by filtration followed by washing with ethyl acetate to give 4-hydroxy-3-methyl-furan-2(5H)-one. $^1$HNMR (500 MHz, CDCl$_3$), δ 4.595 (s, 2H), 3.314 (s, 1H), 1.668 (s, 3H).

Step C: 4-methyl-5-oxo-2,5-dihydrofuran-3-yl trifluoromethanesulfonate

To the solution of 4-hydroxy-3-methylfuran-2(5H)-one (400 mg, 3.51 mmol) in dichloromethane (10 mL) at −78° C. was added 2,6-lutidine (0.612 mL, 5.2.6 mmol) and triflic anhydride (0.711 mL, 4.21 mmol) dropwise. The reaction temperature was maintained at −78° C. for 0.5 h before being warmed to rt for 1 h. The mixture was diluted with DCM (100 mL) and washed with 1 N hydrogen chloride (3 times 100 mL), then with diluted sodium bicarbonate solution, then dried over sodium sulfate, and concentrated to give 4-methyl-5-oxo-2,5-dihydrofuran-3-yl trifluoromethanesulfonate. LC/MS: (M+1)$^+$: 247.0.

Intermediate 5

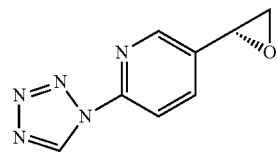

5A

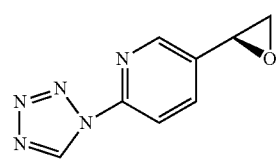

5B (R)-5-(Oxiran-2-yl)-2-(1H-tetrazol-1-yl)pyridine (5A) and (S)-5-(Oxiran-2-yl)-2-(1H-tetrazol-1-yl) pyridine (5B)

Step A: 5-Bromo-2-(1H-tetrazol-1-yl)pyridine

To a solution of 5-bromopyridin-2-amine (5.0 g, 28.9 mmol) in acetic acid (40 ml, 699 mmol) was added (diethoxymethoxy) ethane (7.70 ml, 46.2 mmol), followed by sodium azide (2.82 g, 43.3 mmol). The mixture was heated at 80° C. for 1 h, cooled to room temperature and diluted with water. Precipitate was collected by filtration and dried under high vacuum to provide the title compound.

Step B: 5-Ethenyl-2-(1H-tetrazol-1-yl)pyridine

To a stirring solution of 5-bromo-2-(1H-tetrazol-1-yl)pyridine (1.0 g, 4.42 mmol), in EtOH (70 mL) was added bis[(diphenylphosphino)ferrocene]dichloropalladium(II), complex with dichloromethane (0.361 g, 0.442 mmol), potassium vinyl trifluoroborate (1.18 g, 8.85 mmol, 2 equiv.), triethylamine (1.23 mL, 8.85 mmol, 2 equiv), and water (0.5 mL). The reaction mixture was heated at reflux (90° C., oil bath) under N$_2$. Upon completion (1-2 h) as determined by reverse phase HPLC-MS and TLC (eluent: 10% ethyl acetate in hexane), the mixture was cooled to room temperature, and then diluted with water. The organic layer was separated, and the aqueous layer was extracted with EtOAc. The combined organic layers were washed with brine, dried over MgSO$_4$, and concentrated. The crude material was chromatographed over a column of SiO$_2$ (0-20% EtOAc in hexane as eluent). Evaporation of the solvent yielded the title compound. LCMS [M+1]$^+$=174.0.

Step C: 5-(Oxiran-2-yl)-2-(1H-tetrazol-1-yl)pyridine (5)

To a solution of 5-ethenyl-2-(1H-tetrazol-1-yl)pyridine (0.664 g, 3.83 mmol) in a 2:1 ratio of H$_2$O:t-BuOH (30 mL) was added N-bromosuccinimide (0.751 g, 4.22 mmol) in portions over 5 min. The mixture was heated at 40° C. for 1 h, cooled to 5° C., made basic with sodium hydroxide aqueous solution (0.46 g in 5 mL of H$_2$O, 11.50 mmol), stirred for another 1 h at the same temperature, and poured into H$_2$O (10 mL). The product precipitated out. The solid was collected by filtration, washed with water, and dried in vacuo. $^1$H NMR (500 MHz, DMSO-d$_6$), δ 10.17 (s, 1H), 8.60 (d, J=1.4 Hz, 1H), 8.04-7.99 (m, 2H), 4.14 (dd J=2.7 Hz, J=2.8 Hz, 1H), 3.23 (t, J=4.6 Hz, 1H), 3.02 (dd, J=25 Hz, 1H); LCMS [M+1]⁺=190. Further chiral separation (AD-H 30×250 mm, 50% MeOH/CO₂, 70 mL/min, 100 bar, 46 mg in MeOH/DCM) afforded faster eluted 5A (R)-5-(oxiran-2-yl)-2-1H-tetrazol-1-yl)pyridine and slower eluted 5B (S)-5-(oxiran-2-yl)-2-(1H-tetrazol-1-yl)pyridine. Absolute chemistry was determined by using Vibrational Circular Dichroism (VCD) spectroscopy with high confidence. Analysis was done comparing experimental data to the calculated VCD and IR spectra of the (R) and (S) compounds.

Intermediates 6A and 6B

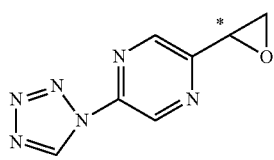

Faster eluting enantiomer

6A

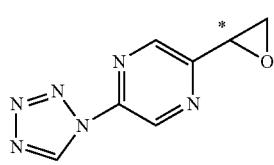

Slower eluting enantiomer

6B (R)-2-(Oxiran-2-yl)-5-(1H-tetrazol-1-yl)pyrazine and (S)-2-(Oxiran-2-yl)-5-(1H-tetrazol-1-yl)pyrazine Step A: 2-Bromo-5-(1H-tetrazol-1-yl) pyrazine: To a solution of 5-bromopyrazin-2-amine (10.75 g, 57.5 mmol) in ethyl acetate (150 ml) was added trimethylsilyl 2,2,2-trifluoroacetate (16.88 ml, 98 mmol). After the mixture was stirred for 5 min, triethoxymethane (17.21 ml, 103 mmol) was added. The resulting mixture was stirred for another five min, and this was followed by addition of azidotrimethylsilane (12.09 ml, 92 mmol). Stirring continued at rt for 2 days, and the mixture was concentrated under reduced pressure. Recrystallization of the residue from ethyl acetate afforded 2-bromo-5-(1H-tetrazol-1-yl)pyrazine. LCMS [M+2+1]⁺=228.9.

Step B: 2-(1H-Tetrazol-1-yl)-5-vinylpyrazine

A solution of 2-bromo-5-(1H-tetrazol-1-yl)pyrazine (11.2 g, 49.3 mmol), potassium vinyltrifluoroborate (13.22 g, 99.0 mmol), 1,1'-bis(diphenylphosphino)ferrocene-palladium(ii) dichloride dichloromethane complex (2.01 g, 2.47 mmol), and TEA (13.75 ml, 99.0 mmol) in ethanol (150 ml) was heated at reflux at 82° C. for 4 h. The reaction mixture was cooled to rt, and the precipitate was filtered off. The filtrate was concentrated, and the residue was purified by flash chromatography (Biotage, Si, ethyl acetate in hexane: 35 to 45%) affording 2-(1H-tetrazol-1-yl)-5-vinylpyrazine LCMS [M+1]⁺=175.10. The filter cake was stirred in DCM (50 mL), and the solid was filtered off. The filtrate was concentrated to afford more 2-(1H-tetrazol-1-yl)-5-vinylpyrazine.

Step C: 2-(Oxiran-2-yl)-5-(1H-tetrazol-1-yl)pyrazine

To a suspension of 2-(1H-tetrazol-1-yl)-5-vinylpyrazine (6.7 g, 38.5 mmol) in t-BuOH:water (96 ml: 190 ml) was added N-bromosuccinimide (7.53 g, 42.3 mmol) in portions at rt. The mixture was heated at 50° C. for 1 h, and cooled to 0° C. in an ice bath. NaOH (4.61 g in 30 mL water, 115 mmol) was added dropwise, and the resulting mixture was stirred at the same temperature for 20 min. The product was collected by filtration, washed with water, dried under vacuum to give 2-(1H-tetrazol-1-yl)-5-vinylpyrazine LCMS [M+1]⁺=191.07. Chiral separation (AD-H 30×250 min, 50% MeOH/CO₂, 70 mL/min, 100 bar, MeOH/DCM) afforded faster eluted isomer 6A and slower eluted isomer 6B. LCMS [M+1]⁺=191.1, Both isomers were useful for the preparation of potent ROMK inhibitors.

The following epoxide intermediates in Table 1 were prepared employing a similar synthetic method as that described for Intermediates 5, 5A, 5B or 6, 6A, 6B. Column 2 shows the structure of the starting material followed by the method used (either I-5 for the procedure described for Intermediate 5, or 1-6 for the procedure described for Intermediate 6). Note that the absolute stereochemistry was not determined unambiguously for these intermediates. Both isomers were useful for the preparation of potent ROMK inhibitors.

TABLE 1

Epoxides prepared using the method described for I-5 or I-6

| Intermediate No. | Column 2 | Structure and name | Structure and name | LC-MS [M + 1]⁺ |
|---|---|---|---|---|
| 7 | ![NH₂-pyridine-Br, Method: I-5] | Fast eluted 7A | Slow eluted 7B | 190.10 |

TABLE 1-continued

Epoxides prepared using the method described for I-5 or I-6

| Intermediate No. | Column 2 | Structure and name | Structure and name | LC-MS [M + 1]+ |
|---|---|---|---|---|
| 8 | Br-pyridine-NH2 (Method: I-5) | Fast eluted 8A | Slow eluted 8B | 188.10 ([M + 1-28]+) |
| 9 | Cl-pyridazine-NH2 (Method: I-6) | Fast eluted 9A | Slow eluted 9B | 191.16 |

Intermediate 10

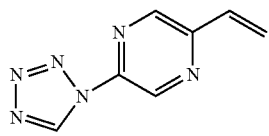

2-(1H-Tetrazol-1-yl)-5-vinylpyrazine

Step A: 2-Bromo-5-(1H-tetrazol-1-yl)pyrazine

To a solution of 5-bromopyrazin-2-amine (10.75 g, 57.5 mmol) in ethyl acetate (150 mL) was added trimethylsilyl 2,2,2-trifluoroacetate (17 mL, 98 mmol). The mixture was stirred for 5 min, and triethoxymethane (17.21 ml, 103 mmol) was added. After the resulting mixture was stirred for another five min, azidotrimethylsilane (12.09 ml, 92 mmol) was added. Stirring continued at rt for 2 days, and the mixture was concentrated under reduced pressure. Recrystallization of the residue from ethyl acetate afforded the title compound. LCMS [M+2+1]+=228.9.

Step B: 2-(1H-Tetrazol-1-yl)-5-vinylpyrazine

A solution of 2-bromo-5-(1H-tetrazol-1-yl)pyrazine (11.2 g, 49.3 mmol), potassium vinyltrifluoroborate (13.2 g, 99.0 mmol), 1,1'-bis(diphenylphosphino)ferrocene-palladium(ii) dichloride dichloromethane complex (2.01 g, 2.47 mmol), and TEA (13.8 mL, 99.0 mmol) in ethanol (150 mL) was heated at reflux at 82° C. for 4 h. The reaction mixture was allowed to cool to rt, and the precipitation was filtered off. The filtrate was concentrated, and the residue was purified by flash chromatography (Biotage, Si, ethyl acetate in hexane: 35 to 45%) affording the title compound. The filter cake was stirred in DCM (50 mL), and the solid was filtered off. The filtrate was concentrated to afford more of the title compound. LCMS [M+1]+=175.1.

The following arylvinyl intermediates in Table 2 were prepared employing a similar synthetic method as that described for Intermediate 10 using the noted starting material.

TABLE 2

Arylvinyls prepared according to the method described for INTERMEDIATE 10

| Intermediate No. | Starting material | Structure and name | LC-MS [M + 1]+ |
|---|---|---|---|
| 11 | Br-pyridazine-NH2 | 3-(1H-tetrazol-1-yl)-6-vinylpyridazine | 175 |
| 12 | Br-pyridine-NH2 | 2-(1H-tetrazol-1-yl)-5-vinylpyridine | 174 |

TABLE 2-continued

Arylvinyls prepared according to the method described for INTERMEDIATE 10

| Intermediate No. | Starting material | Structure and name | LC-MS [M + 1]+ |
|---|---|---|---|
| 13 | 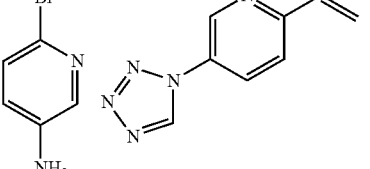 | | 174.2 |

5-(1H-tetrazol-1-yl)-2-vinylpyridine

Intermediate 14

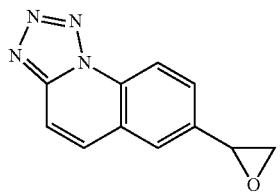 [SMILES: c1cc2c(ccc3nnnn32)cc1C1CO1]

7-(oxiran-2-yl)tetrazolo[1,5-α]quinoline

Step A: 7-bromotetrazolo[1,5-α]quinoline

A solution of 6-bromo-2-chloroquinoline (4.00 g, 16.6 mmol) and sodium azide (2.16 g, 3.32 mmol) in 20 mL DMF was stirred at 130° C. for 18 h. Then the solution was poured into cold water (200 mL) and stirred for 30 min, filtered and washed with cold water, dried to afford the title compound. LC/MS[M+1]+=248.9.

Step B: 7-vinyltetrazolo[1,5-α]quinoline

To a mixture of 7-bromotetrazolo[1,5-α]quinoline (3.35 g, 13.4 mmol), potassium vinyltrifluoroborate (3.62 g, 8.0 mmol), Pd(dppr)Cl₂ (335 mg, 0.44 mmol) in EtOH (100 mL) was added Et₃N (1.31 g, 13.2 mmol), the mixture was heated at 80° C. for 2 hours. The mixture was cooled and filtered, rinsed the cake with EtOH, and then concentrated, the residue was purified on silica gel column eluted with petroleum ether/EtOAc from 5/1 to 1/1 as eluting solvents to afford the title compound. LC/MS [M+1]+=197.1.

Step C: 7-(oxiran-2-yl)tetrazolo[1,5-α]quinoline

A mixture of 7-vinyltetrazolo[1,5-α]quinoline (1.64 g, 8.32 mmol) and NBS (1.62 g, 9.15 mmol) in a solution of t-butanol (27.3 mL) and water (54.6 mL) was heated to 40° C., stirred until the solid was mostly dissolved, then stirred for another 2 hours, a solution of NaOH (998 mg, 25.0 mmol) in water (11 mL) was added slowly, cooled to 0° C., then stirred for 1 hour, concentrated, purified on silica gel column eluted with petroleum ether/EtOAc=1/1 as eluting solvents to afford the title compound. LC/MS[M+1]+=213.1.

Intermediate 15

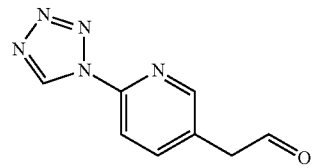 [SMILES: O=CCc1ccc(-n2cnnn2)nc1]

2-(6-(1H-Tetrazol-1-yl)pyridin-3-yl)acetaldehyde

Step A: 2-(6-(1H-Tetrazol-1-yl)pyridin-3-yl)ethanol

To a solution of 5-(oxiran-2-yl)-2-(1H-tetrazol-1-yl) pyridine (500 mg, 2.64 mmol) in ethanol (5.3 mL) were added 10% Pd/C (101 mg, 0.952 mmol) and HCOONH₄(500 mg, 7.93 mmol). The reaction mixture was vigorously stirred for 1.5 h, and filtered through a pad of silica gel. The filtrate was evaporated to give 2-(6-(1H-tetrazol-1-yl)pyridin-3-yl)ethanol. ¹H NMR (500 MHz, CDCl₃) δ 9.54 (s, 1H), 8.43 (d, J=2.0 Hz, 1H), 8.02 (d, J=8.3 Hz, 1H), 7.90 (dd, J=8.3, 2.0 Hz, 1H), 3.91 (t, J=6.3 Hz, 2H), 2.96 (t, J=6.3 Hz, 2H), Step B: 2-(6-(1H-Tetrazol-1-yl)pyridin-3-yl)acetaldehyde To a solution of 2-(6-(1H-tetrazol-1-yl)pyridin-3-yl)ethanol (100 mg, 0.523 mmol) in DCM (2.6 mL) was added Dess-Martin periodinane (333 mg, 0.785 mmol). The mixture was stirred for 1.5 h, diluted with 10% Na₂S₂O₂, NaHCO₃, and stirred for 20 min. The aqueous layer was extracted with DCM, and the combined organic layers were washed with brine, dried (MgSO₄), and concentrated to give title compound. LC/MS: [(M+1)]+=190

Intermediate 16

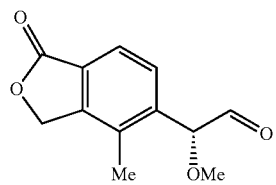 [SMILES: CO[C@@H](C=O)c1ccc2c(c1C)COC2=O]

(R)-2-methoxy-2-(4-methyl-1-oxo-1,3-dihydroisobenzofuran-5-yl)acetaldehyde

Step A: (R)-5-(2-hydroxy-1-methoxyethyl)-4-methylisobenzofuran-1(3H)-one

To a solution of (S)-4-methyl-5-(oxiran-2-yl)isobenzofuran-1(3H)-one (300 mg, 1.58 mol) in MeOH (10 mL) was added TsOH (30 mg, 0.16 mmol). The resulting mixture was stirred at 70° C. for 2 h. The mixture was concentrated and partitioned between EtOAc and water; the organic layer was separated and concentrated to afford the title compound.

Step B: (R)-2-methoxy-2-(4-methyl-1-oxo-1,3-dihydroisobenzofuran-5-yl)acetaldehyde DMP (405 mg, 0.96 mmol) was added to a solution of (R)-5-(2-hydroxy-1-methoxyethyl)-4-methylisobenzofuran- 1(3H)-one (212 mg, 0.96 mmol) in DCM (3 mL) in one portion. The resulting mixture was stirred at room temperature for 18 h. The mixture was diluted with EtOAc, washed with water; the organic layer was concentrated to afford the title compound.

Intermediate 17

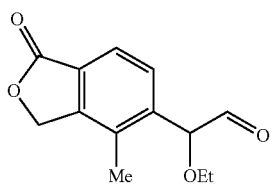 [SMILES: CCOC(C=O)c1ccc2c(c1C)COC2=O]

2-ethoxy-2-(4-methyl-1-oxo-1,3-dihydroisobenzofuran-5-yl)acetaldehyde

The title compound was prepared from (S)-4-methyl-5-(oxiran-2-yl)isobenzofuran-1(3H)-one in an analogous fashion as described for (R)-2-methoxy-2-(4-methyl-1-oxo-1,3-dihydroisobenzofuran-5-yl)acetaldehyde (Intermediate 16), but using ethanol in place of methanol.

Intermediate 18

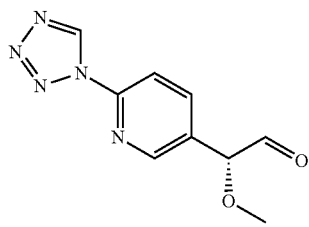 [SMILES: CO[C@@H](C=O)c1ccc(-n2cnnn2)nc1]

(R)-2-(6-(1H-tetrazol-1-yl)pyridin-3-yl)-2-methoxyacetaldehyde

The title compound was prepared from (S)-5-(oxiran-2-yl)-2-(1H-tetrazol-1-yl)pyridine (Intermediate 5B) in an analogous fashion as described for (R)-2-methoxy-2-(4-methyl-1-oxo-1,3-dihydroisobenzofuran-5-yl)acetaldehyde (Intermediate 16).

Intermediate 19

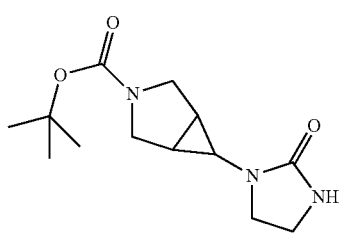 [SMILES: CC(C)(C)OC(=O)N1CC2C(C1)C2N1CCNC1=O]

tert-butyl 6-(2-oxoimidazolidin-1-yl)-3-azabicyclo[3.1.0]hexane-3-carboxylate

Step A: tert-butyl 6-(3-(2-chloroethyl)ureido)-3-azabicyclo[3.1.0]hexane-3-carboxylate To an ice-cooled DCM (10 ml) solution of tert-butyl 6-amino-3-azabicyclo[3.1.0]hexane-3-carboxylate (1.01 g, 5.09 mmol) was added triethylamine (1.775 mL, 12.74 mmol) and then 2-chloroethyl isocyanate (0.591 g, 5.60 mmol). After 1 hour, the reaction mixture was quenched with aqueous sodium bicarbonate and the aqueous layer was extracted with DCM (3×10 mL). The combined organic layers were then dried over sodium sulfate, filtered and concentrated in vacuo to afford tert-butyl 6-(3-(2-chloroethyl)ureido)-3-azabicyclo[3.1.0]hexane-3-carboxylate which was used without further purification.

Step B: tert-butyl 6-(2-oxoimidazolidin-1-yl)-3-azabicyclo[3.1.0]hexane-3-carboxylate To an ice-cooled THF (10 mL) solution of tert-butyl 6-(3-(2-chloroethyl)ureido)-3-azabicyclo[3.1.0]hexane-3-carboxylate (1.50 g, 4.94 mmol) was added LiHMDS (5.93 mL, 5.93 mmol) dropwise. The reaction was allowed to gradually warm to ambient temperature. Reaction is complete after 1.5 hours. The reaction mixture was quenched with aqueous sodium bicarbonate and the aqueous layer was extracted with ethyl acetate (3×10 mL). The combined organic layers were then dried over sodium sulfate, filtered, concentrated in vacuo and purified via MPLC (0-100% EtOAc/Hex then 10% methanol/DCM gradient) to afford tert-butyl 6-(2-oxoimidazolidin-1-yl)-3-azabicyclo[3.1.0]hexane-3-carboxylate. LC/MS: $[(M+1)]^+=268$.

Intermediate 20

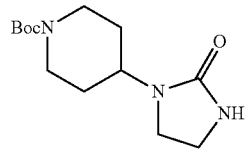 [SMILES: CC(C)(C)OC(=O)N1CCC(N2CCNC2=O)CC1]

tert-butyl 4-(2-oxoimidazolidin-1-yl)piperidine-1-carboxylate

Step A: tert-butyl 4-(3-(2-chloroethyl)ureido)piperidine-1-carboxylate

To an ice-cooled solution of tert-butyl 4-aminopiperidine-1-carboxylate (25.00 g, 125 mmol) in DCM (160 mL) was added TEA (31.00 g, 312 mmol) and 1-chloro-2-isocyanatoethane (14.50 g, 138 mmol). After 10 min, the mixture was stirred at room temperature for 1 h. The mixture was diluted with DCM (200 mL), washed with aqueous sodium bicarbonate (200 mL×2), then dried and concentrated to afford the title compound.

Step B: tert-butyl 4-(2-oxoimidazolidin-1-yl)piperidine-1-carboxylate

To a solution of tert-butyl 4-(3-(2-chloroethyl)ureido)piperidine-1-carboxylate (6.87 g, 22.5 mmol) in THF (50 mL) was added LiHMDS (1.0M, 27 mL, 27 mmol) dropwise at 0° C., then the mixture was allowed to warm to room temperature gradually and stirred for 2 h. The mixture was quenched with aqueous sodium bicarbonate, extracted with EtOAc (50 mL×3), the combined organic layers were dried and concentrated. The residue was purified via silica gel to afford the title compound. LC/MS: [(M+1)]$^+$=270.

Intermediate 21

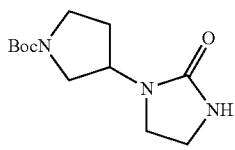

tert-butyl 3-(2-oxoimidazolidin-1-yl)pyrrolidine-1-carboxylate

The title compound was prepared in an analogous fashion to that described for tert-butyl 4-(2-oxoimidazolidin-1-yl)piperidine-1-carboxylate (intermediate 20) except starting from tert-butyl 3-aminopyrrolidine-1-carboxylate. LC/MS: [(M+1)]$^+$=256.

Intermediate 22

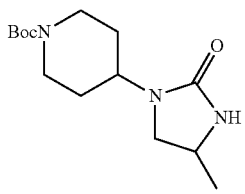 [SMILES: CC1CN(C2CCN(C(=O)OC(C)(C)C)CC2)C(=O)N1]

tert-butyl 4-(4-methyl-2-oxoimidazolidin-1-yl)piperidine-1-carboxylate

Step A: tert-butyl 4-((3-methoxy-2-methyl-3-oxopropyl)amino)piperidine-1-carboxylate To a solution of tert-butyl 4-aminopiperidine-1-carboxylate (8.00 g, 40 mmol) in MeOH (80 mL) was added methyl methacrylate (6.00 g, 60 mmol) the resulting mixture was heated to 65° C. and stirred for 5 days. The mixture was diluted with DCM, washed with water, brine, dried over Na$_2$SO$_4$, filtered and concentrated to afford the title compound.

Step B: 3-((1-(tert-butoxycarbonyl)piperidin-4-yl)amino)-2-methylpropanoic acid

To a solution of tert-butyl 4-(3-methoxy-2-methyl-3-oxopropyl)amino)piperidine-1-carboxylate (7.30 g, 24 mmol) in MeOH (40 mL) and water (20 mL) was added NaOH (1.40 g, 35 mmol) at room temperature for 16 hours. The mixture was washed by DCM; aqueous phase was acidified with 3 M HCl to pH 7, concentrated to afford the title compound.

Step C: tert-butyl 4-(4-methyl-2-oxoimidazolidin-1-yl)piperidine-1-carboxylate

To a solution of DPPA (14.0 g, 51 mmol), TEA (5.60 g, 55 mmol) in toluene (40 mL) was added 3-((1-(tert-butoxycarbonyl)piperidin-4-yl)amino)-2-methylpropanoic acid (6.60 g, crude), the resulting mixture was heated to reflux and stirred for 16 hours under N$_2$ protection. The mixture was diluted with DCM, washed with water, saturated sodium bicarbonate and concentrated; the residue was washed with a mixture of PE/EtOAc (10:1) to afford the title compound.

Intermediate 23

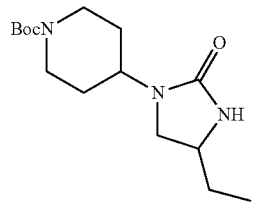 [SMILES: CCC1CN(C2CCN(C(=O)OC(C)(C)C)CC2)C(=O)N1]

tert-butyl 4-(4-ethyl-2-oxoimidazolidin-1-yl)piperidine-1-carboxylate

Step A: ethyl 2-formylbutanoate

Ethyl butyrate (10.00 g, 86.1 mmol) was added slowly to a cooled solution of LDA (130 mL, 2 Min THF, 260 mmol) in 200 mL of dry THF. The resulting mixture was stirred at −78° C. for 1 h, then ethyl formate (32.00 g, 432 mmol) was added dropwise and the resulting mixture was allowed to warm to room temperature and stirred for 3 h. The reaction mixture was quenched with 750 mL of water and extracted by PE (200 mL×3). The aqueous layer was acidified with conc. HCl to pH2 and then extracted by tert-butyl methyl ether (300 mL*3). The ether layer was washed with brine and dried over Na$_2$SO$_4$, filtered and concentrated to afford the title compound.

Step B: tert-butyl 4-((2-(ethoxycarbonyl)butyl)amino)piperidine-1-carboxylate

To a solution of ethyl 2-formylbutanoate (14.00 g, 97.2 mmol) and tert-butyl 4-aminopiperidine-1-carboxylate (20.00 g, 100 mmol) in DCM (200 mL) was added AcOH (11.50 g, 192 mmol), the mixture was stirred at room temperature for 4 h, then NaBH$_3$—CN (18.50 g, 294 mmol) was added, the mixture was stirred at same temperature for 16 h. The mixture was quenched by 100 mL of water, extracted by DCM, washed with water, brine, dried over Na$_2$SO$_4$ and concentrated to afford the title compound.

Step C: 2-(((1-(tert-Butoxycarbonyl)piperidin-4-yl)amino)methyl)butanoic acid

To a solution of tert-butyl 4-((2-(ethoxycarbonyl)butyl)amino)piperidine-1-carboxylate (28.00 g, 85.3 mmol) in MeOH (100 mL) and water (40 mL) was added NaOH (4.10 g, 103 mmol) at room temperature, the mixture was stirred at room temperature for 16 hours. The mixture was washed by DCM; aqueous phase was adjusted to ph7 by 3 M HCl, concentrated to afford the title compound. $^1$H-NMR (400

MHz, MeOD) δ ppm 3.86-3.83 (m, 2H), 3.16 (s, 2H), 2.82-2.65 (m, 4H), 2.14-2.10 (m, 1H), 1.82-1.75 (m, 3H), 1.58-1.54 (m, 1H), 1.37 (s, 9H), 1.27-1.13 (m, 2H), 0.86-0.79 (m, 3H).

Step D: tert-butyl 4-(4-ethyl-2-oxoimidazolidin-1-yl)piperidine-1-carboxylate

To a solution of 2-(((1-(tert-butoxycarbonyl)piperidin-4-yl)amino)methyl)butanoic acid (17.00 g, crude) and TEA (11.00 g, 109 mmol) in toluene (400 mL) was added DPPA (28.00 g, 102 mmol), the resulting mixture was heated to reflux and stirred for 16 hours under $N_2$ protection. The mixture was cooled and concentrated, the residue was diluted with DCM, washed with water, saturated sodium bicarbonate, dried and concentrated, the residue was purified on silica gel (25% to 50% EtOAc in PE) to give the title compound.

Intermediate 24

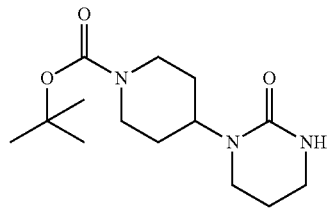 [SMILES: CC(C)(C)OC(=O)N1CCC(N2CCCNC2=O)CC1]

tert-butyl 4-(2-oxotetrahydropyrimidin-1(2H)-yl)piperidine-1-carboxylate

Step A: tert-butyl 4-(3-(3-chloropropyl)ureido)piperidine-1-carboxylate

4-Amino-1-BOC-piperidine (1.00 g, 4.99 mmol), was dissolved in DCM (20 mL). The resulting solution was cooled to 0° C. using an ice-water bath and sequentially treated with triethylamine (1.740 mL, 12.48 mmol) and 3-chloropropyl isocyanate (0.564 mL, 5.49 mmol). The reaction mixture was warmed to ambient temperature and followed by LC/MS. After ~1.5 h, LC/MS indicated formation of the desired product. The reaction mixture was partitioned between DCM and saturated aq. $NaHCO_3$. The organic layer was separated, dried ($Na_2SO_4$), filtered and concentrated to afford the title compound.

Step B: tert-butyl 4-(2-oxotetrahydropyrimidin-1(2H)piperidine-1-carboxylate tert-butyl 4-(3-(3-chloropropyl)ureido)piperidine-1-carboxylate (1.79 g, 5.60 mmol), was diluted in THF (20 mL) and cooled to 0° C. using an ice-water bath. A 1M/THF solution of LiHMDS (6.72 mL, 6.72 mmol) was added dropwise over ~10 min. The reaction mixture was allowed to gradually warm to ambient temperature. LC/MS analysis after ~15 h of stirring at ambient temperature indicated formation of the desired product. The reaction mixture was concentrated; the residue was quenched with saturated aq. $NaHCO_3$ and extracted with EtOAc. The combined organic layers were dried ($Na_2SO_4$), filtered and concentrated. The residue was purified by flash chromatography using a 40 g ISCO RediSep® Rf silica gel column with gradient elution 0-10% MeOH/DCM (30 min; 40 mL/min). The desired fractions (determined by $KENO_4$ stain) were combined, concentrated and dried in vacuo to afford the title compound. LC/MS: $[(M+1)]^+=284$.

Intermediate 25

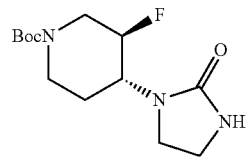 [SMILES: CC(C)(C)OC(=O)N1CC[C@@H](N2CCNC2=O)[C@H](F)C1]

tert-butyl trans-3-fluoro-4-(2-oxoimidazolidin-1-yl)piperidine-1-carboxylate

Step A: benzyl 4-oxopiperidine-1-carboxylate

Into a 20 L 4-necked round bottom flask was placed piperidin-4-one hydrochloride (1100 g, 8.11 mol, 1.00 equiv), THF (5500 mL) and water (5500 mL). To the mixture was added $K_2CO_3$ (2239 g, 16.20 mol, 2.00 equiv) while the flask was cooled to −5° C. To the above was added benzyl carbonochloridate (1453 g, 8.52 mol, 1.05 equiv) dropwise with stirring at −5° C. over 20 minutes. The resulting solution was allowed to react, with stirring, for 2 hours while the temperature was maintained at room temperature. The reaction progress was monitored by TLC (EtOAc/PE=1:2). A filtration was performed. The filtrate was extracted three times with 10 L of $CH_2Cl_2$. The organic layers were combined, washed 3 times with 8 L of brine, dried over $MgSO_4$ and concentrated under vacuum to afford the title compound.

Step B: benzyl 4-(trimethylsilyloxy)-5,6-dihydropyridine-1(2H)-carboxylate

Into a 10 L 3-necked round bottom flask was placed benzyl 4-oxopiperidine-1-carboxylate (1700 g, 7.29 mol, 1.00 equiv), DMF (8500 ml) and TEA (2590 g, 25.59 mol, 3.51 equiv). To the above was added TMSCI (1587 g, 14.61 mol, 2.01 equiv) dropwise with stirring. The resulting solution was allowed to react, with stirring, overnight while the temperature was maintained at 85° C. The reaction progress was monitored by TLC (EtOAc/PE=1:2). The reaction mixture was then quenched by the addition of ice water. The resulting solution was extracted with PE. The organic layers were combined, washed with brine, dried over MgSO, and concentrated under vacuum to afford the title compound.

Step C: 3-fluoro-4-oxopiperidine-1-carboxylate

Into a 10000 mL 3-necked round bottom flask was placed benzyl 4-(trimethylsilyloxy)-5,6-dihydropyridine-1(2H)-carboxylate (365 g, 1.19 mol, 1.00 equiv) and acetonitrile (5000 ml). To the above was added SelectFluor® (321.5 g, 952.03 mmol, 0.99 equiv) in several batches at 0° C. over 20 minutes. The resulting solution was allowed to react, with stirring, overnight while the temperature was maintained at room temperature. The reaction progress was monitored by TLC (EtOAc/PE=1:1). The mixture was concentrated under vacuum. The residual solution was diluted with 3 L of EtOAc. A filtration was performed. The filtrate was concentrated under vacuum. The residue was purified with a silica gel column eluting with a 1:400 MeOH:DCM solvent system to afford the title compound.

Step D: benzyl cis-3-fluoro-4-hydroxypiperidine-1-carboxylate

Into a 5 L 4-necked round bottom flask was placed a solution of benzyl 3-fluoro-4-oxopiperidine-1-carboxylate (687 g, 2.73 mol, 1.00 equiv) in methanol (3500 ml). To the mixture was added NaBH$_4$ (83.8 g, 2.22 mol, 0.66 equiv) in several batches at 0° C. The resulting solution was stirred for 4 hours at room temperature. The reaction progress was monitored by TLC (EtOAc/PE=1:1). The reaction mixture was then quenched by adding 2000 ml of water. The resulting solution was extracted three times with 2000 ml of EtOAc. The organic layers were combined, washed 3 times with 2000 ml of brine, dried over MgSO$_4$ and concentrated under vacuum. The residue was purified with a silica gel column eluted with a 1:8 EtOAc/PE solvent system to afford the title compound.

Step E: tert-butyl cis-3-fluoro-4-hydroxypiperidine-1-carboxylate

A mixture of benzyl cis-3-fluoro-4-hydroxypiperidine-1-carboxylate (290 g, 1.15 mol, 1.00 equiv), Boc$_2$O (261.3 g, 1.20 mol, 1.05 equiv) and Pd(OH)$_2$/C (29 g, 10%) in methanol (2300 ml) was hydrogenated (8 atm) for 3 hours at room temperature. A filtration was performed. The filtrate was concentrated under vacuum. The crude product was purified by recrystallization from DCM:PE in the ratio 1:10 to afford the title compound. $^1$H-NMR –(300 MHz, CDCl$_3$, ppm): δ 1.46 (9H, m), 2.0 (2H, m), 3.4 (1H, s), 3.7 (1H, s), 3.8 (2H, m), 4.5 (2H, d)

Step F: tert-butyl cis-3-fluoro-4-(methylsulfonyloxy)piperidine-1-carboxylate Into a 5000 ml 4-necked round bottom flask was placed a solution of tert-butyl cis-3-fluoro-4-hydroxypiperidine-1-carboxylate (203 g, 925.88 mmol, 1.00 equiv) in DCM (2000 ml) and TEA (121.4 g, 1.20 mol, 1.30 equiv). To the above was added MsCl (138.3 g, 1.21 mol, 1.49 equiv) dropwise with stirring, at 0° C. The resulting solution was stirred for 2 hours at room temperature. The reaction progress was monitored by TLC (DCM/EtOAc=2:1). The resulting solution was diluted with 200 ml of aq. NH$_4$Cl (10%), then extracted three times with 3000 ml of DCM. The organic layers were combined, washed two times with 2000 ml of brine, dried over Na$_2$SO$_4$ and concentrated under vacuum to afford the title compound.

Step G: tert-butyl trans-4-azido-3-fluoropiperidine-1-carboxylate

Into a 5000 ml 4-necked round bottom flask was placed a solution of tert-butyl cis-3-fluoro-4-(methylsulfonyloxy)piperidine-1-carboxylate (275 g, 924.87 mmol, 1.00 equiv) in DMF (2100 ml). To the mixture was added NaN$_3$ (180.9 g, 2.78 mol, 3.02 equiv). The resulting solution was stirred overnight at 90~100° C. in an oil bath. The reaction progress was monitored by TLC (EtOAc/PE=1:2). The resulting solution was cooled and diluted with 3000 ml of aq. NaOH (10%), then extracted three times with 3000 ml of DCM. The organic layers were combined, washed two times with 3000 ml of water and two times with 3000 mL of brine, dried over Na$_2$SO$_4$ and concentrated under vacuum. The residue was purified by eluting through a column with a 1:20 EtOAc/PE solvent system to afford the title compound.

Step H: tert-butyl trans-4-amino-3-fluoropiperidine-1-carboxylate

A mixture of tert-butyl trans-4-azido-3-fluoropiperidine-1-carboxylate (180 g, 736.89 mmol, 1.00 equiv) and Pd(OH)$_2$/C (18 g, 10%) in CH$_3$OH (2000 ml) was hydrogenated (3 atm) overnight at room temperature. The reaction progress was monitored by TLC (MeOH/DCM=1:10). A filtration was performed. The filtrate was concentrated under vacuum. The residue was purified by eluting through a silica gel column with a 1:100 MeOH:DCM solvent system. The collected fraction was concentrated under vacuum. The residue was washed 2 times with 400 ml of hexane to afford the title compound. LC-MS (ES, m/z): 204 [M−C$_4$H$_8$+CH$_3$CN+H]$^+$

Step I and J: tert-butyl trans-3-fluoro-4-(2-oxoimidazolidin-1-yl)piperidine-1-carboxylate The title compound was prepared in two steps starting from tert-butyl trans-4-amino-3-fluoropiperidine-1-carboxylate and 1-chloro-2-isocyanatoethane in an analogous fashion as described for tert-butyl 4-(2-oxoimidazolidin-1-yl)piperidine-1-carboxylate above (Intermediate 20). LC-MS (ES, m/z): 288 [M+H]$^+$

Intermediate 26

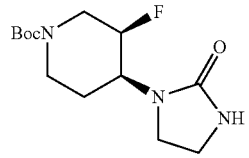 [SMILES: CC(C)(C)OC(=O)N1CC[C@H](N2CCNC2=O)[C@H](F)C1]

cis-tert-butyl 3-fluoro-4-(2-oxoimidazolidin-1-yl)piperidine-1-carboxylate

Step A: cis-tert-butyl 4-(benzylamino)-3-fluoropiperidine-1-carboxylate

Into a 5000 ml 4-necked round bottom flask purged and maintained with an inert atmosphere of nitrogen was placed tert-butyl 3-fluoro-4-oxopiperidine-1-carboxylate (prepared as described above, 257 g, 1.18 mol, 1.00 equiv) and THF (1850 ml). To the above was added BnNH$_2$ (143.9 g, 1.34 mol, 1.13 equiv) dropwise with stirring at 0° C. To the mixture was added NaB(AcO)$_3$H (675 g, 3.19 mol, 2.69 equiv). The resulting solution was stirred overnight at room temperature. The reaction progress was monitored by TLC (EtOAc:PE=1:2). The resulting mixture was diluted with 2000 ml of aq. K$_2$CO$_3$, then extracted 2 times with 2000 mL of EtOAc. The organic layers were combined, dried over MgSO$_4$ and concentrated under vacuum. The residue was purified by eluting through a silica gel column with a 1:20 EtOAc:PE solvent system to afford the title compound.

Step B: cis-tert-butyl 4-amino-3-fluoropiperidine-1-carboxylate

A mixture of cis-tert-butyl 4-(benzylamino)-3-fluoropiperidine-1-carboxylate (128 g, 415.58 mmol, 1.00 equiv) and Pd(OH)₂/C (13 g) in MeOH (2000 ml) was hydrogenated overnight at room temperature. The reaction progress was monitored by TLC (MeOH/DCM=1:20). A filtration was performed. The filtrate was concentrated under vacuum. The residue was purified by eluting through a silica gel column with a 1:100 MeOH:DCM solvent system to afford the title compound. LC-MS (ES, m/z): 204 [M−C₄H₈+CH₃CN+H]⁺; H-NMR (300 MHz, CDCl₃, ppm): δ 1.46 (9H, s), 1.50 (2H, s), 1.67 (2H, t), 2.92 (3H, m), 4.05 (1H, s), 4.30 (1H, s), 4.54 (1H, d).

Step C and D: tert-butyl trans-3-fluoro-4-(2-oxoimidazolidin-1-yl)piperidine-1-carboxylate The title compound was prepared in two steps starting from tert-butyl trans-4-amino-3-fluoropiperidine-1-carboxylate and 1-chloro-2-isocyanatoethane in an analogous fashion as described for tert-butyl 4-(2-oxoimidazolidin-1-yl)piperidine-1-carboxylate above (intermediate 20). LC-MS (ES, m/z): 288 [M+H]⁺

Intermediate 27

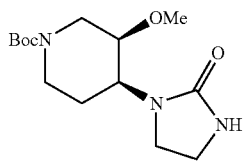 [SMILES: CO[C@@H]1CN(C(=O)OC(C)(C)C)CC[C@@H]1N1CCNC1=O]

cis-tert-butyl 3-methoxy-4-(2-oxoimidazolidin-1-yl)piperidine-1-carboxylate

The title compound was prepared in an analogous fashion as described for tert-butyl 4-(2-oxoimidazolidin-1-yl)piperidine-1-carboxylate (Intermediate 20), except starting from commercially available cis-tert-butyl 4-amino-3-methoxypiperidine-1-carboxylate (available from several sources including Oakwood Chemical, catalog #040789). LC-MS (ES, m/z): 300 [M+H]⁺

Intermediate 28

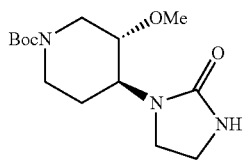 [SMILES: CO[C@H]1CN(C(=O)OC(C)(C)C)CC[C@@H]1N1CCNC1=O]

trans-tert-butyl 3-methoxy-4-(2-oxoimidazolidin-1-yl)piperidine-1-carboxylate

The title compound was prepared in an analogous fashion as described for tert-butyl 4-(2-oxoimidazolidin-1-yl)piperidine-1-carboxylate (Intermediate 20), except starting from commercially available trans-tert-butyl 4-amino-3-methoxypiperidine-1-carboxylate (available from several sources including Indofine Chemical Company, Inc., catalog #08-6346). LC-MS (ES, m/z): 300 [M+H]⁺

Intermediate 29

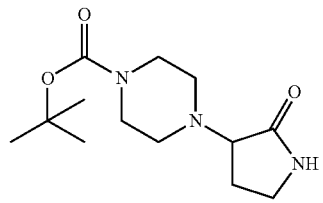 [SMILES: CC(C)(C)OC(=O)N1CCN(C2CCNC2=O)CC1]

tert-butyl 4-(2-oxopyrrolidin-3-yl)piperazine-1-carboxylate

Step A: tert-butyl 3-bromo-2-oxopyrrolidine-1-carboxylate

To a −78° C. cooled THF (14 mL) solution of 1-(tert-butoxycarbonyl)-2-pyrrolidinone (2.00 g, 10.8 mmol) was add LiHMDS (3.97 g, 23.76 mmol) dropwise. The mixture was stirred for 10 minutes at which time a THF (14 mL) solution of N-bromosuccinimide (1.922 g, 10.80 mmol) was added. The reaction was allowed to stir for another 10 minutes and then quenched by the addition of aqueous ammonium chloride. The aqueous layer was extracted 3 times with DCM (10 mL). The combined organic layers were then dried over sodium sulfate, filtered, concentrated in vacuo and purified via MPLC (0-100% EtOAc/Hex) to afford tert-butyl 3-bromo-2-oxopyrrolidine-1-carboxylate.

Step B: tert-butyl 4-(1-(tert-butoxycarbonyl)-2-oxopyrrolidin-3-yl piperazine-1-carboxylate To an acetonitrile (10 ml) solution of tert-butyl 3-bromo-2-oxopyrrolidine-1-carboxylate (1 g, 3.79 mmol) was added potassium carbonate (1.570 g, 11.36 mmol) and 1-BOC-piperazine (0,705 g, 3.79 mmol). The reaction mixture was heated to 40° C. for 2 hours, cooled to ambient temperature and solids filtered. The organic layer was concentrated in vacuo and purified via MPLC (0-100% EtOAc/Hex) to afford tert-butyl 4-(1-(tert-butoxycarbonyl)-2-oxopyrrolidin-3-yl)piperazine-1-carboxylate.

Step C: 3-(piperazin-1-yl)pyrrolidin-2-one

To a DCM (10 ml) solution of tert-butyl 4-(1-(tert-butoxycarbonyl)-2-oxopyrrolidin-3-yl)piperazine-1-carboxylate (1.15 g, 3.11 mmol) was added TFA (1.199 mL, 15.56 mmol). The mixture was allowed to stir at ambient temperature for 2 hours after which the solution was concentrated in vacuo. The crude residue was then diluted in methanol and passed through a 10 G ion exchange resin. The free base was released using 4 M ammonia in methanol to afford 3-(piperazin-1-yl)pyrrolidin-2-one.

Step D: tert-butyl 4-(2-oxopyrrolidin-3-yl)piperazine-1-carboxylate

To a THF (20 mL) solution of 3-(piperazin-1-yl)pyrrolidin-2-one (530 mg, 3.13 mmol) was added Hunig's Base (0.547 mL, 3.13 mmol) and BOC-Anhydride (0.800 mL, 3.45 mmol). The mixture was heated to 40° C. for 15 hours. After this time, the reaction mixture was cooled to ambient temperature, quenched with aqueous sodium bicarbonate and the aqueous layer was extracted with ethyl acetate (3×10 mL). The combined organic layers were then dried over sodium sulfate, filtered, concentrated in vacuo and purified via MPLC (0-100% EtOAc/Hex then 10% methanol/DCM gradient) to afford tert-butyl 4-(2-oxopyrrolidin-3-yl)piperazine-1-carboxylate.

Intermediate 30

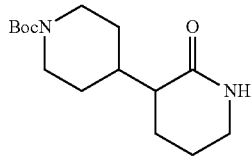 [SMILES: CC(C)(C)OC(=O)N1CCC(C2CCCNC2=O)CC1]

tert-butyl 2-oxo-[3,4'-bipiperidine]-1'-carboxylate

Step A: methyl 4-cyano-2-(pyridin-4-yl)butanoate

To a solution of methyl 2-(pyridin-4-yl)acetate (10.0 g, 66 mmol) in 20 mL of tert-butanol was added Triton B (0.4 mL) and acrylonitrile (7.00 g, 132 mmol) at 0° C. The resultant mixture was stirred at room temperature for 48 h. The mixture was concentrated and diluted with water (150 mL), then extracted with ethyl acetate, the organic layer was washed with brine, dried over anhydrous $Na_2SO_4$, filtered and concentrated, the residue was purified by column chromatography (EtOAc:MeOH=10:1) to give the title compound. $^1$H-NMR (400 MHz, $CDCl_3$) δ ppm 8.59-8.56 (m, 2H), 7.26-7.20 (m, 2H), 3.78-3.73 (m, 1H), 3.69-3.61 (m, 3H), 2.48-2.31 (m, 2H), 2.28-2.21 (m, 1H), 2.18-2.06 (m, 1H).

Step B: 3-(pyridin-4-yl)piperidin-2-one

A mixture of methyl 4-cyano-2-(pyridin-4-yl)butanoate (7.80 g, 34.3 mmol), Raney Ni (0.80 g), $NH_4OH$ (10 mL) in 200 mL of MeOH was stirred at 65° C. for 5 h under 55 Psi of hydrogen. The mixture was then filtered and concentrated. The residue was purified by flash chromatography to afford the title compound. $^1$H-NMR (400 MHz, $CDCl_3$) δ ppm 8.96-8.77 (m, 2H), 7.52-7.21 (m, 2H), 6.33 (s, 1H), 3.68-3.60 (m, 1H), 3.48-3.39 (m, 3H), 2.20-2.18 (m, 2H), 1.98-1.84 (m, 4H).

Step C: [3,4'-bipiperidin]-2-one 3-(Pyridin-4-yl)piperidin-2-one (3.80 g, 21.5 mmol) and $PtO_2$ (0.38 g) in acetic acid (40 mL) was hydrogenated at 80° C. for 37 h under 800 Psi of hydrogen, and then cooled to room temperature, filtered and concentrated to afford the title compound.

Step D: tert-butyl 2-oxo-[3,4'-bipiperidine]-1'-carboxylate

To a solution of [3,4'-bipiperidin]-2-one (400 mg, 2.1 mmol) in 2 mL of THF was added $Boc_2O$ (432 mg, 2 mmol) and 2 mL of TEA, the resulting mixture was stirred at room temperature overnight, the mixture was concentrated, and the residue was purified by chromatography (PE:EtOAc=4:1) to give the title compound. $^1$H-NMR (400 MHz, MeOD) δ ppm 4.19-4.05 (m, 2H), 3.28-3.17 (m, 2H), 2.83-2.59 (r n, 2H), 2.33-2.13 (m, 2H), 1.95-1.81 (m, 2H), 1.75-1.61 (m, 1H), 1.60-1.50 (m, 2H), 1.49-1.39 (m, 9H), 137-1.28 (m, 2H).

Intermediate 31

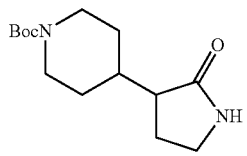 [SMILES: CC(C)(C)OC(=O)N1CCC(C2CCNC2=O)CC1]

tert-butyl 4-(2-oxopyrrolidin-3-yl)piperidine-1-carboxylate

Step A: tert-butyl 4-(2-methoxy-2-oxoethylidene)piperidine-1-carboxylate

A mixture of 60% sodium hydride (1.30 g, 33 mmol) in 145 mL of DMF was cooled to 0° C., methyl 2-(dimethoxyphosphoryl)acetate (4.8 mL, 31 mmol) was then added dropwise. After 20 minutes at 0° C., a solution of tert-butyl 4-oxopiperidine-1-carboxylate (5.00 g, 25 mmol) in 13 mL of DMF was added dropwise. The reaction mixture was stirred at r.t. for 3 hours, and then diluted with EtOAc, washed with water; the organic layer was separated and washed with brine, dried over $Na_2SO_4$, filtered and concentrated to afford the title compound. $^1$H-NMR (400 MHz, $CDCl_3$) δppm 5.70 (s, 1H), 3.67 (s, 3H), 3.40-3.53 (m, 4H), 2.85-2.95 (t, J=6.0 Hz, 2H), 2.20-2.30 (t, J=5.2 Hz, 2H), 1.45 (s, 9H).

Step B: tert-butyl 4-(2-methoxy-2-oxoethyl)piperidine-1-carboxylate

Crude tert-butyl 4-(2-methoxy-2-oxoethylidene)piperidine-1-carboxylate above was hydrogenated with 0.7 g of 10% Pd/C in EtOAc/MeOH (1:1, 50 mL) under 55 Psi overnight, filtered and concentrated. The residue was purified by flash chromatography (PE:EtOAc from 15:1 to 8:1) to afford the title compound. $^1$H-NMR (400 MHz, $CDCl_3$) δ ppm 4.10 (s, 2H), 3.65 (s, 3H), 2.60-2.75 (t, J=12 Hz, 2H), 2.19-2.26 (t, J=7.2 Hz, 2H), 1.81-1.95 (m, 1H), 1.60-1.70 (d, =13 Hz, 2H). 1.40-1.45 (m, 9H), 1.05-1.18 (m, 2H).

Step C: tert-butyl 4-(3-cyano-1-methoxy-1-oxopropan-2-yl)piperidine-1-carboxylate To a mixture of diisopropylamine (0.78 g, 7.8 mmol) in THF (10 mL) was added dropwise with n-BuLi (2.7 mL, 6.8 mmol) at −60° C. After being stirred at −60° C. for 0.5 hours, tert-butyl 4-(2-methoxy-2-oxoethyl)piperidine-1-carboxylate (1.00 g, 3.9 mmol) in THF (5 mL) was added dropwise at −60° C. After 1 hour, bromoacetonitrile (0.93 g, 7.8 mmol) was added dropwise at −60° C., the mixture was then stirred at r.t. overnight. The reaction mixture was quenched by water, extracted with EtOAc. The combined organic layers were dried over $Na_2SO_4$, filtered and concentrated. The residue was purified by column chromatography (PE:EtOAc=20/1 to 3/1) to afford the title compound. $^1$H-NMR (400 MHz, $CDCl_3$) δ ppm 5.28 (s, 2H), 3.65 (s, 3H), 2.60-2.70 (m, 4H), 2.50-2.60 (m, 1H), 1.81-1.90 (m, 1H), 1.62 (t, J=2.0 Hz, 2H), 1.40-1.45 (m, 9H), 1.15-1.23 (m, 2H).

Step D: tert-butyl 4-(2-oxopyrrolidin-3-yl)piperidine-1-carboxylate

A mixture of Raney Ni (0.70 g), tert-butyl 4-(3-cyano-1-methoxy-1-oxopropan-2-yl)piperidine-1-carboxylate (0.71 g, 2.3 mmol), 1.0 mL of ammonia in 40 mL of methanol was hydrogenated at 50 Psi and 80° C. overnight. The mixture was filtered and concentrated. The residue was purified by chromatography (PE:EtOAc=8:1 to 1/1) to afford the title compound. $^1$H-NMR (400 MHz, CDCl$_3$) δ ppm 5.70 (s, 1H), 4.10 (s, 2H), 3.40-3.45 (m, 4H), 3.25 (t, J=8.0 Hz, 2H), 2.65 (s, 2H), 1.65-1.78 (t, J=14 Hz, 2H), 1.45 (d, J=8.0 Hz, 1H), 1.36 (s, 10H).

Intermediate 32

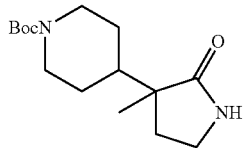 [SMILES: CC(C)(C)OC(=O)N1CCC(C2(C)CCNC2=O)CC1]

tert-butyl 4-(3-methyl-2-oxopyrrolidin-3-yl)piperidine-1-carboxylate

Step A: tert-butyl 4-(1-(tert-Butoxycarbonyl)-2-oxopyrrolidin-3-yl)piperidine-1-carboxylate To a solution of tert-butyl 4-(2-oxopyrrolidin-3-yl)piperidine-1-carboxylate (1.00 g, 3.73 mmol) in 10 mL of CH$_3$CN was added Boc$_2$O (1.20 g, 5.58 mmol), followed by DMAP (42 mg, 0.37 mmol), the resulting mixture was stirred at room temperature overnight and then concentrated, the residue was partitioned between H$_2$O and ethyl acetate, the organic layer was washed with 1 M HCl solution and brine, dried over anhydrous Na$_2$SO$_4$, filtered and concentrated, the residue was purified by flash chromatography eluted with 0 to 30% of ethyl acetate in PE to afford the title compound. $^1$H-NMR (400 MHz, CDCl$_3$) δ ppm 4.23-4.02 (br, 2H), 3.76-3.70 (m, 1H), 3.60-3.51 (m, 1H), 2.75-2.63 (m, 2H), 2.55-2.46 (m, 1H), 2.08-1.96 (m, 2H), 1.88-1.73 (m, 2H), 1.52 (s, 10H), 1.44 (s, 9H), 1.32-1.20 (m, 2H).

Step B: tert-butyl 4-(1-(tert-butoxycarbonyl)-3-methyl-2-oxopyrrolidin-3-yl)piperidine-1-carboxylate To a stirred solution of dry diisopropylamine (684 mg, 6.80 mmol) in 10 mL of dry THF was added n-BuLi (2.5 M in hexanes, 2.0 mL, 5.1 mmol) under N$_2$ atmosphere at −78° C., the reaction mixture was stirred at −78° C. for 5 min and then warmed to 0° C. After 30 min, the reaction was cooled to −78° C. A solution of (R)-tert-butyl 4-(tert-butoxycarbonyl)-2-oxopyrrolidin-3-yl)piperidine-1-carboxylate (1.00 g, 2.72 mmol) in 8 mL of dry THF was added dropwise at −78° C. After stirring for 30 min at the same temperature, a solution of MeI (1.90 g, 13.6 mmol) in 1 mL of THF was added dropwise, the mixture was then stirred overnight while the temperature rose to room temperature. The mixture was quenched with saturated NH$_4$Cl solution, extracted with ethyl acetate, the aqueous layer was extracted with ethyl acetate, the combine organic layer was dried over anhydrous Na$_2$SO$_4$, filtered and concentrated, the residue was purified by flash chromatography eluted with 0 to 25% of ethyl acetate in PE to afford the title compound. $^1$H-NMR (400 MHz, CDCl$_3$) δ ppm 4.25-4.05 (br, 2H), 3.72-3.55 (m, 2H), 2.65 (t, J=11 Hz, 2H), 2.04-1.94 (m, 1H), 1.81-1.75 (m, 2H), 1.62-1.54 (m, 4H), 1.53 (s, 9H), 1.45 (s, 9H), 1.26-1.10 (m, 2H).

Step C: 3-methyl-3-(piperidin-4-yl)pyrrolidin-2-one

To a solution of tert-butyl 4-(1-(tert-butoxycarbonyl)-3-methyl-2-oxopyrrolidin-3-yl)piperidine-1-carboxylate (2.75 g, 7.20 mmol) in EtOAc (25 mL) was added HCl/EtOAc (4 M 28 mL) at room temperature, the resulting mixture was stirred at room temperature for 3 h. The mixture was concentrated to afford the title compound as hydrochloride.

Step D: tert-butyl 4-(3-methyl-2-oxopyrrolidin-3-yl)piperidine-1-carboxylate To a solution of 3-methyl-3-(piperidin-4-yl)pyrrolidin-2-one (2.10 g, 11.5 mmol) and TEA (3.50 g, 34.6 mmol) in MeCN (25 mL) was added (Boc)$_2$O (3.80 g, 17.4 mmol) at room temperature, the resulting mixture was heated to 80° C. and stirred for 6 hours. The reaction mixture was diluted with DCM, washed with water, brine, dried over Na$_2$SO$_4$, filtered and concentrated; the residue was purified on silica gel eluted with 25% to 50% of EtOAc in PE to afford the title compound. $^1$H-NMR (400 MHz, CDCl$_3$) δ ppm 5.89 (s, 1H), 4.12-4.11 (m, 2H), 3.32-3.24 (m, 2H), 2.66 (s, 2H), 2.14-2.09 (m, 1H), 1.78-1.55 (m, 5H), 1.45 (s, 9H), 1.27-1.22 (m, 1H), 1.16 (s, 3H).

Intermediate 33

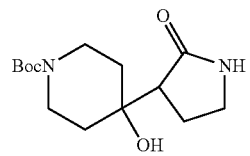 [SMILES: CC(C)(C)OC(=O)N1CCC(O)(C2CCNC2=O)CC1]

tert-butyl 4-hydroxy-4-(2-oxopyrrolidin-3-yl)piperidine-1-carboxylate

To a stirred solution of anhydrous diisopropylamine (4.50 g, 44 mmol) in 50 mL of dry THF was added a 2.5 M solution of n-BuLi in hexane (13.6 mL, 34 mmol) under N$_2$ atmosphere at −78° C. The solution was stirred for 15 min, and then a solution of 1-(trimethylsilyl)pyrrolidin-2-one (5.50 g, 35 mmol) in 20 mL of dry THF was added dropwise at −78° C. After stirring for 50 min at the same temperature, a solution of tert-butyl 4-oxopiperidine-1-carboxylate (4.40 g, 22 mmol) in 20 mL of dry THF was added dropwise, the mixture was warmed slowly to room temperature and stirred overnight under N$_2$ atmosphere. The mixture was acidified with 5% HCl solution under ice cooling, extracted with ethyl acetate, the organic layer was washed with 5% HCl solution, water, brine, dried over anhydrous Na$_2$SO$_4$, filtered and concentrated to afford the title compound. $^1$H-NMR (400 MHz, CDCl$_3$) δ ppm 6.08 (s, 1H), 4.53 (br, 1H), 3.94 (br, 2H), 3.33 (q, J=4.8 Hz, 2H), 3.15 (br, 2H), 2.55 (t, J=10 Hz, 1H), 2.20-2.15 (m, 1H), 1.95-1.80 (m, 1H), 1.65-1.58 (m, 2H), 1.48 (s, 10H).

Intermediate 34

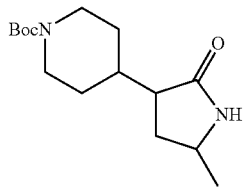

tert-butyl 4-(5-methyl-2-oxopyrrolidin-3-yl)piperidine-1-carboxylate

Step A: tert-butyl 4-(1-methoxy-4-methyl-1-oxopent-4-en-2-yl)piperidine-1-carboxylate LiHMDS (1.2M in THF, 25 mL, 30 mL) was added dropwise to a solution of tert-butyl 4-(2-methoxy-2-oxoethyl)piperidine-1-carboxylate (5.00 g, 1.9 mmol) in THF (50 mL) at −78° C. After being stirred at same temperature for 1 h, 3-bromo-2-methylprop-1-ene (2.60 g, 1.9 mmol) was added; the reaction mixture was stirred at this temperature for 0.5 h, and then stirred at room temperature overnight. The reaction was quenched with saturated aqueous NH₄Cl and extracted with EtOAc; the combined organic extracts were dried over Na₂SO₄, filtered and concentrated to give the title compound.

Step B: tert-butyl 4-(1-methoxy-1,4-dioxopentan-2-yl)piperidine-1-carboxylate

To a solution of tert-butyl 4-(1-methoxy-4-methyl-1-oxopent-4-en-2-yl)piperidine-1-carboxylate (300 mg, 0.96 mmol) in MeOH (3 mL) was added OsO₄ (2 mg, 0.01 mmol), followed by NaIO₄ (800 mg, 4.0 mmol) in H₂O (3 mL), the resulting mixture was stirred at room temperature for 12 h. After removing the solvent and partitioned between with H₂O and EtOAc, the organic layer was separated and concentrated to get the title compound.

Step C: tert-butyl 4-(5-methyl-2-oxopyrrolidin-3-yl)piperidine-1-carboxylate

To a solution of tert-butyl 4-(1-methoxy-1,4-dioxopentan-2-yl)piperidine-1-carboxylate (100 mg, 0.32 mmol) in MeOH (3 mL) was added NH₄OAc (100 mg, 6.4 mmol), NaBH₃CN (77 mg, 6.4 mmol) and MgSO₄(160 mg, 6.4 mmol), and then the reaction mixture was heated under reflux overnight. The reaction mixture was cooled and partitioned between water and EtOAc, the organic layer was separated and concentrated, the residue was purified by column chromatography on silica eluted with EtOAc/PE and MeOH/DCM to get the title compound. ¹H-MR (400 Hz, CDCl₃) δ ppm 4.13-4.08 (m, 2H), 3.71-3.63 (m, 1H), 2.68 (d, J=4.0 Hz, 2H), 2.44 (t, J=5.2 Hz, 2H), 2.11-1.62 (m, 2H), 1.73-1.66 (m, 2H), 1.43 (s, 9H), 1.28-1.21 (m, 4H).

Intermediate 35

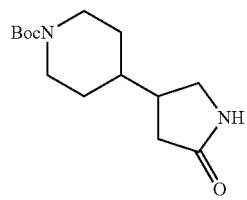 [SMILES: CC(C)(C)OC(=O)N1CCC(C2CNC(=O)C2)CC1]

tert-butyl 4-(5-oxopyrrolidin-3-yl)piperidine-1-carboxylate

Step A: (E)-ten-butyl 4-(3-methoxy-3-oxoprop-1-en-1-yl)piperidine-1-carboxylate

To a mixture of methyl 2-(diethoxyphosphoryl)acetate (5.90 g, 28 mmol) in THF (100 mL) was added DBU (4.30 g, 28 mmol) and LiCl (1.20 g, 28 mmol), the mixture was stirred at room temperature for 30 min, then tert-butyl 4-formylpiperidine-1-carboxylate (5.00 g, 23 mmol) was added. The reaction mixture was stirred at room temperature for 16 hours. The mixture was quenched by saturated NH₄Cl (aq.), then extracted with ethyl acetate, the organic layers were washed by brine, dried over anhydrous Na₂SO₄, filtered and concentrated, the crude product was purified by column chromatography (PE:EtOAc=20:1~3:1) to afford the title compound.

Step B: tert-butyl 4-(4-methoxy-1-nitro-4-oxobutan-2-yl)piperidine-1-carboxylate To a mixture of (E)-tert-butyl 4-(3-methoxy-3-oxoprop-1-en-1-yl)piperidine-1-carboxylate (2.00 g, 7.4 mmol), in CH₃NO₂ (20 mL) was added DBU (1.10 g, 7.4 mmol). The mixture was heated to reflux and stirred for 16 hours. The mixture was cooled, diluted with ethyl acetate, washed by brine, dried over anhydrous Na₂SO₄, filtered and concentrated, the residue was purified by column chromatography (PE:EtOAc=20:1~3:1) to afford the title compound.

Step C: tert-butyl 4-(5-oxopyrrolidin-3-yl)piperidine-1-carboxylate

To a mixture of tert-butyl. 4-(4-methoxy-1-nitro-4-oxobutan-2-yl)piperidine-1-carboxylate (1.50 g, 4.5 mmol) in MeOH (20 mL) was added Raney Ni (200 mg). The mixture was stirred under H₂ atmosphere (balloon) at room temperature for 24 hours, then filtered and concentrated to afford the title compound.

Intermediate 36

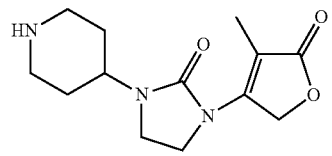 [SMILES: CC1=C(N2CCN(C3CCNCC3)C2=O)COC1=O]

1-(4-methyl-5-oxo-2,5-dihydrofuran-3-yl)-3-(piperidin-4-yl)imidazolidin-2-one

Step A: tert-butyl 4-(3-(4-methyl-5-oxo-2,5-dihydrofuran-3-yl)-2-oxoimidazolidin-1-yl)piperidine-1-carboxylate A mixture of tert-butyl 4-(2-oxoimidazolidin-1-yl)piperidine-1-carboxylate (5.38 g, 20 mmol), 4-methyl-5-oxo-2,5-dihydrofuran-3-yl trifluoromethanesulfonate (4.92 g, 20 mmol), Pd(OAc)$_2$ (0.22 g, 1.0 mmol), Cs$_2$CO$_3$ (13.04 g, 40 mmol) and Xantphos (1.16 g, 2.0 mmol) in toluene (100 mL) and H$_2$O (1.08 g, 60 mmol) was stirred at 60° C. for 12 h under N$_2$. After cooling, the mixture was diluted with EtOAc (150 mL) and washed with water (100 mL). The organic layer was separated and concentrated. The residue was purified via silica gel to afford the title compound.

$^1$H-NMR (400 MHz, CDCl$_3$) δ ppm 5.20 (s, 2H), 4.22 (s, 1H), 4.16 (t, J=7.8 Hz, 2H), 3.83-3.95 (m, 1H), 3.55 (t, J=7.8 Hz, 2H), 2.72-2.82 (m, 2H), 2.00 (s, 3H), 1.50-1.78 (m, 4H), 1.42 (s, 9H).

Step B: 1-(4-methyl-5-oxo-2,5-dihydrofuran-3-yl)-3-(piperidin-4-yl)imidazolidin-2-one tert-Butyl 4-(3-(4-methyl-5-oxo-2,5-dihydrofuran-3-yl)-2-oxoimidazolidin-1-yl)piperidine-1-carboxylate (1.3 g, 3.6 mmol) was dissolved in HCl/EtOAc (4 M, 20 mL), then the mixture was stirred at room temperature for 30 min. After removing the solvent, the residue was purified via SCX (Ion exchange column) to afford the title compound. LC/MS: [(M+1)]$^+$=266.

Intermediate 37

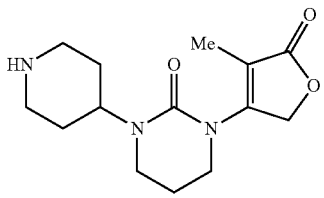 [SMILES: CC1=C(N2CCCN(C3CCNCC3)C2=O)COC1=O]

1(4-methyl-5-oxo-2,5-dihydrofuran-3-yl)-3-(piperidin-4-yl)tetrahydropyrimidin-2(1H)-one The title compound was prepared in an analogous fashion as described for 1-(4-methyl-5-oxo-2,5-dihydrofuran-3-yl)-3-(piperidin-4-yl)imidazolidin-2-one above (Intermediate 36) starting from tert-butyl 4-(2-oxotetrahydropyrimidin-1(2H)-yl)piperidine-1-carboxylate and 4-methyl-5-oxo-2,5-dihydrofuran-3-yl trifluoromethanesulfonate. LC/MS: [(M+1)]$^+$=280.

Intermediate 38

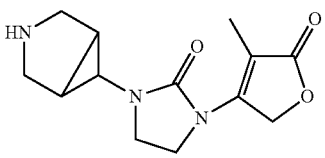 [SMILES: CC1=C(N2CCN(C3C4CNCC43)C2=O)COC1=O]

1-(3-azabicyclo[3.1.0]hexan-6-yl)-3-(4-methyl-5-oxo-2,5-dihydrofuran-3-yl)imidazolidin-2-one The title compound was prepared in an analogous fashion as described for 1-(4-methyl-5-oxo-2,5-dihydrofuran-3-yl)-3-(piperidin-4-yl)imidazolidin-2-one above (Intermediate 36) starting from tert-butyl 6-(2-oxoimidazolidin-1-yl)-3-azabicyclo[3.1.0]hexane-3-carboxylate and 4-methyl-5-oxo-2,5-dihydrofuran-3-yl trifluoromethanesulfonate. LC/MS: [(M+1)]$^+$=264.

Intermediate 39

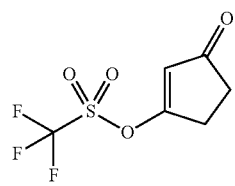

3-Oxocyclopent-1-enyl trifluoromethanesulfonate

To a solution of 1,3 cyclopentadione (2.5 g, 25.5 mmol) in DCM (50 mL) at −78° C. was added 2,6-lutidine (4.45 ml, 38 mmol), followed by triflic anhydride (5.14 mL, 30.6 mmol) dropwise. The reaction temperature was maintained at −78° C. for 0.5 h before warming to RT for 1 h. The mixture was washed with 1 N HCl (10 mL), and NaHCO$_3$ (5 mL—diluted solution), dried over Na$_2$SO$_4$, concentrated to give the title compound. LC-MS (IE, m/z): 231 [M+1]$^+$ Intermediate 40

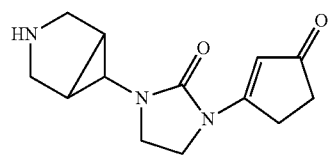 [SMILES: O=C1C=C(N2CCN(C3C4CNCC43)C2=O)CC1]

1-(3-azabicyclo[13.1.01]hexan-6-yl)-3-(3-oxocyclopent-1-en-1-yl)imidazolidin-2-one The title compound was prepared in an analogous fashion as described for 1-(4-methyl-5-oxo-2,5-dihydrofuran-3-yl)-3-(piperidin-4-yl)imidazolidin-2-one above (Intermediate 36) starting from tert-butyl 6-(2-oxoimidazolidin-1-yl)-3-azabicyclo[3.1.0]hexane-3-carboxylate and 3-oxocyclopent-1-en-1-yl methanesulfonate. LC/MS: [(M+1)]$^+$=248.

Intermediate 41

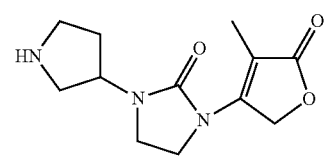

1-(4-methyl-5-oxo-2,5-dihydrofuran-3-yl)-3-(pyrrolidin-3-yl)imidazolidin-2-one

The title compound was prepared in an analogous fashion as described for 1-(4-methyl-5-oxo-2,5-dihydrofuran-3-yl)-3-(piperidin-4-yl)imidazolidin-2-one (Intermediate 36) starting from tert-butyl 3-(2-oxoimidazolidin-1-yl)pyrrolidine-1-carboxylate and 4-methyl-5-oxo-2,5-dihydrofuran-3-yl trifluoromethanesulfonate. LC/MS: [(M+1)]$^+$=252.

Intermediates 42A and 42B (Two Single Enantiomers)

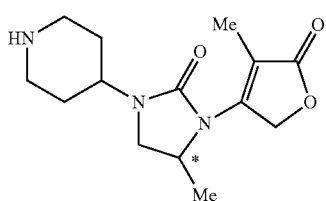 [SMILES: CC1=C(N2C(=O)N(C3CCNCC3)CC2C)COC1=O]

(R)-4-methyl-3-(4-methyl-5-oxo-2,5-dihydrofuran-3-yl-1-(piperidin-4-yl)imidazolidin-2-one and (S)-4-methyl-3-(4-methyl-5-oxo-2,5-dihydrofuran-3-yl)-1-(piperidin-4-yl)imidazolidin-2-one Step A: tert-butyl 4-(4-methyl-3(4-methyl-5-oxo-2,5-dihydrofuran-3-yl)-2-oxoimidazolidin-1-yl)piperidine-1-carboxylate A mixture of tert-butyl 4-(4-methyl-2-oxoimidazolidin-1-yl)piperidine-1-carboxylate (2.50 g, 8.8 mmol), 4-methyl-5-oxo-2,5-dihydrofuran-3-yl trifluoromethanesulfonate (2.80 g, 11 mmol), Pd$_2$(dba)$_3$ (0.50 g, 0.55 mmol) and Xantphos (1.00 g, 1.7 mmol) in toluene (30 mL) was added Cs$_2$CO$_3$ (8.60 g, 26 mmol), the mixture was heated to reflux, and stirred for 16 hours under N$_2$ protection. The mixture was concentrated, purified on silica gel (PE/EtOAc from 10/1 to 2/1), then separated by SFC chiral chromatography (Column: Chiralcel OD-3 150×4.6 min I.D., 3 um; Mobile phase: iso-propanol (0.05% DEA) in CO$_2$ from 5% to 40%; Flow rate: 2.5 mL/min; Wavelength: 220 nm) to afford the title compounds (faster eluting and slower eluting enantiomers).

Faster eluting peak: $^1$H-NMR (400 MHz, CDCl$_3$) δ ppm 5.38-5.30 (m, 1H), 5.11-5.06 (m, 1H), 4.53-4.50 (m, 1H), 4.23-4.21 (m, 2H), 3.94-3.91 (m, 1H), 3.67-3.63 (m, 1H), 3.07 (d, J=8.0 Hz, 1H), 2.09-2.76 (m, 2H), 1.96 (s, 3H), 1.83-1.54 (m, 2H), 1.60-1.58 (m, 2H), 1.46 (s, 9H), 1.34 (d, J=6.4 Hz, 3H).

Slower eluting peak: $^1$H NMR (400 MHz, CDCl$_3$) δ ppm 5.38-5.30 (m, 1H), 5.10-5.06 (m, 1H), 4.53-4.50 (m, 1H), 4.22 (s, 2H), 3.93-3.89 (m, 1H), 3.67-3.63 (m, 1H), 3.07 (d, J=8.8 Hz, 1H), 2.78 (s, 2H), 1.96 (s, 3H), 1.83-1.54 (m, 2H), 1.59-1.55 (m, 2H), 1.46 (s, 9H), 1.35-1.33 (d, J=6.4 Hz, 3H).

Step E: 4-methyl-3-(4-methyl-5-oxo-2,5-dihydrofuran-3-yl)-1-(piperidin-4-yl)imidazolidin-2-one To a solution of tert-butyl 4-(4-methyl-3-(4-methyl-5-oxo-2,5-dihydrofuran-3-yl)-2-oxoimidazolidin-1-yl)piperidine-1-carboxylate (faster eluting peak from Step A, 470 mg, 1.24 mmol) in 4 mL of EtOAc was added 5 mL of HCl/EtOAc, the mixture was stirred at room temperature for 3 h and then concentrated to afford the title compound as a single enantiomer (42A). Similarly, the slower eluting product from Step A could be converted to the enantiomeric title compound (42B) using HCl. The absolute stereochemistry of each product was not established; however, both enantiomers were useful for preparing ROMK inhibitors.

Intermediates 43A and 43B (Two Single Enantiomers)

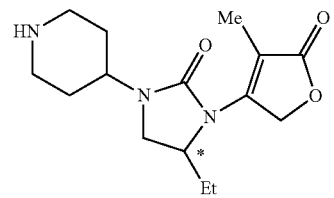 [SMILES: CCC1CN(C2CCNCC2)C(=O)N1C1=C(C)C(=O)OC1]

(R)-4-ethyl-3-(4-methyl-5-oxo-2,5-dihydrofuran-3-yl)-1-(piperidin-4-yl)imidazolidin-2-one AND (S)-4-ethyl-3-(4-methyl-5-oxo-2,5-dihydrofuran-3-yl)-1-(piperidin-4-yl)imidazolidin-2-one Step E: tert-butyl 4-(4-ethyl-3-(4-methyl-5-oxo-2,5-dihydrofuran-3-yl)-2-oxoimidazolidin-1-yl)piperidine-1-carboxylate To a mixture of tert-butyl 4-(4-ethyl-2-oxoimidazolidin-1-yl)piperidine-1-carboxylate (2.50 g, 8.41 mmol), 4-methyl-5-oxo-2,5-dihydrofuran-3-yl trifluoromethanesulfonate (2.70 g, 11.0 mmol), Pd$_2$(dba)$_3$ (0.425 g, 0.436 mmol) and Xantphos (1.00 g, 1.73 mmol) in a toluene (100 mL) was added Cs$_2$CO$_3$ (8.30 g, 25.5 mmol), then heated to reflux, stirred for 16 hours under N$_2$ protection. The mixture was cooled and filtered, concentrated in vacuum, purified on silica gel eluted with PE/EtOAc from 10/1 to 1/1, then separated by SFC chiral chromatography (Column: Chiralcel OD-3 150×4.6 mm I.D., 3 um; Mobile phase: iso-propanol (0.05% DEA) in CO$_2$ from 5% to 40%; Flow rate: 2.5 mL/min; Wavelength: 254 nm) to afford the title compounds as single enantiomers. $^1$H-NMR (400 MHz, CDCl$_3$) δ ppm 5.42-5.37 (m, 1H), 5.09-5.05 (m, 1H), 4.34-4.06 (m, 4H), 3.62-3.57 (m, 1H), 3.20-3.18 (m, 1H), 2.78 (s, 2H), 2.04 (s, 1H), 1.93 (s, 3H), 1.71-1.64 (m, 3H), 1.62 (s, 1H), 1.46 (s, 9H), 1.27-1.24 (m, 1H), 0.96-0.91 (m, 3H).

Step F: 4-ethyl-3(4-methyl-5-oxo-2,5-dihydrofuran-3-yl)-1-(piperidin-4-yl)imidazolidin-2-one tert-butyl 4-(4-ethyl-3-(4-methyl-5-oxo-2,5-dihydrofuran-3-yl)-2-oxoimidazolidin-1-yl)piperidine-1-carboxylate (faster eluting isomer from Step A, 1.30 g, 3.3 mmol) in EtOAc (15 mL) was treated with HCl/EtOAc (4 M, 10 mL) and the resulting mixture was stirred at 25° C. for 18 h. The mixture was concentrated to afford the title compound as a single enantiomer 43A. Similarly, the slower eluting product from Step A could be converted to the enantiomeric title compound (43B) using HCl. The absolute stereochemistry of each product was not established; however, both enantiomers were useful for preparing ROMK inhibitors.

Intermediates 44A and 44B (Two Single Enantiomers)

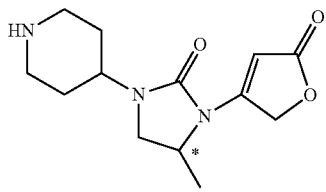 [SMILES: CC1CN(C2CCNCC2)C(=O)N1C1=CC(=O)OC1]

(R)-4-methyl-3-(5-oxo-2,5-dihydrofuran-3-yl)-1-(piperidin-4-yl)imidazolidin-2-one AND (S)-4-methyl-3-(5-oxo-2,5-dihydrofuran-3-yl)-1-(piperidin-4-yl)imidazolidin-2-one

Step A: tert-butyl 4-(1-methyl-2-oxo-3-(5-oxo-2,5-dihydrofuran-3-yl)imidazolidin-1-yl)piperidine-1-carboxylate To a mixture of tert-butyl 4-(4-methyl-2-oxoimidazolidin-1-yl)piperidine-1-carboxylate (2.80 g, 9.88 mmol), 5-oxo-2,5-dihydrofuran-3-yl trifluoromethanesulfonate (2.90 g, 12.5 mmol), $Pd_2(dba)_3$ (453 mg, 0.495 mmol) and Xantphos (1.15 g, 1.98 mmol) in a toluene (30 mL) was added $Cs_2CO_3$ (9.66 g, 29.6 mmol), the resulting mixture was heated under reflux for 16 hours under $N_2$ protection. The mixture was concentrated, the residue was purified by flash chromatography (PE/EtOAc from 5/1 to 1/1), and then separated by SFC chiral chromatography (Column: Chiralcel OD-3 150×4.6 mm I.D., 3 um; Mobile phase: isopropanol (0.05% DEA) in $CO_2$ from 5% to 40%; Flow rate: 2.5 mL/min, Wavelength: 220 nm to get two single enantiomers (faster eluting A and slower eluting B).

Step B: 4-methyl-3-(5-oxo-2,5-dihydrofuran-3-yl)-1-(piperidin-4-yl)imidazolidin-2-one To a solution of tert-butyl 4-(4-methyl-2-oxo-3-(5-oxo-2,5-dihydrofuran-3-yl)imidazolidin-1-yl)piperidine-1-carboxylate (first eluting in Step A under SFC chromatography, 220 mg, 0.60 mmol) in EtOAc (2.5 mL) was added HCl/EtOAc (4.5 mL), the mixture was then stirred at room temperature for 24 hours, and then concentrated to afford the title compound as a single enantiomer 44A. Similarly, the slower eluting product from Step A can be converted to the enantiomeric title compound (44B) using HCl. The absolute stereochemistry of each product was not established; however, both enantiomers were useful for preparing ROMK inhibitors.

Intermediate 45

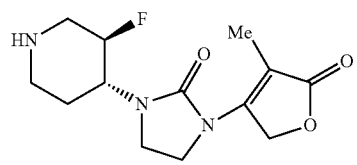 [SMILES: CC1=C(N2CCN([C@@H]3CCNC[C@H]3F)C2=O)COC1=O]

trans-1-(3-fluoropiperidin-4-yl)-3-(4-methyl-5-oxo-2,5-dihydrofuran-3-yl)imidazolidin-2-one The title compound was prepared in two steps in an analogous fasion as described for 1-(4-methyl-5-oxo-2,5-dihydrofuran-3-yl)-3-(piperidin-4-yl)imidazolidin-2-one (Intermediate 36) above starting from 4-methyl-5-oxo-2,5-dihydrofuran-3-yl trifluoromethanesulfonate and tert-butyl trans-3-fluoro-4-(2-oxoimidazolidin-1-yl)piperidine-1-carboxylate. LC/MS: $[(M+1)]^+=284$.

Intermediate 46

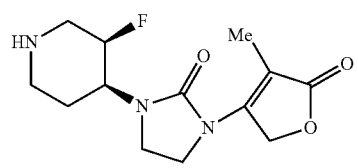 [SMILES: CC1=C(N2CCN([C@H]3CCNC[C@H]3F)C2=O)COC1=O]

cis-1-(3-fluoropiperidin-4-yl)-3-(4-methyl-5-oxo-2,5-dihydrofuran-3-yl)imidazolidin-2-one The title compound was prepared in two steps in an analogous fasion as described for 1-(4-methyl-5-oxo-2,5-dihydrofuran-3-yl)-3-(piperidin-4-yl)imidazolidin-2-one (Intermediate 36) above starting from 4-methyl-5-oxo-2,5-dihydrofuran-3-yl trifluoromethanesulfonate and cis-tert-butyl 3-fluoro-4-(2-oxoimidazolidin-1-yl)piperidine-1-carboxylate. LC/MS: $[(M+1)]^+=284$.

Intermediate 47

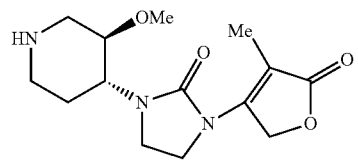 [SMILES: CO[C@@H]1CNCC[C@H]1N1CCN(C2=C(C)C(=O)OC2)C1=O]

trans-1-((3-methoxypiperidin-4-yl)-3-(4-methyl-5-oxo-2,5-dihydrofuran-3-yl)imidazolidin-2-one The title compound was prepared in two steps in an analogous fasion as described for 1-(4-methyl-5-oxo-2,5-dihydrofuran-3-yl)-3-(piperidin-4-yl)imidazolidin-2-one (Intermediate 36) above starting from 4-methyl-5-oxo-2,5-dihydrofuran-3-yl trifluoromethanesulfonate and trans-tert-butyl 3-methoxy-4-(2-oxoimidazolidin-1-yl)piperidine-1-carboxylate. LC/MS: $[(M+1)]^+=796$.

Intermediate 48

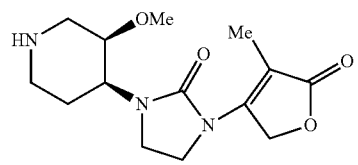 [SMILES: CO[C@@H]1CNCC[C@@H]1N1CCN(C2=C(C)C(=O)OC2)C1=O]

cis-1-((3-methoxypiperidin-4-yl)-3-(4-methyl-5-oxo-2,5-dihydrofuran-3-yl)imidazolidin-2-one The title compound was prepared in two steps in an analogous fasion as described for 1-(4-methyl-5-oxo-2,5-dihydrofuran-3-yl)-3-(piperidin-4-yl)imidazolidin-2-one (Intermediate 36) above starting from 4-methyl-5-oxo-2,5-dihydrofuran-3-yl trifluoromethanesulfonate and cis-tert-butyl 3-methoxy-4-(2-oxoimidazolidin-1-yl)piperidine-1-carboxylate. LC/MS: [(M+1)]$^+$=296.

Intermediate 49A and 49B (Separated Single Isomers)

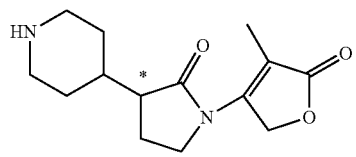 [SMILES: CC1=C(N2CCC(C3CCNCC3)C2=O)COC1=O]

(R)-1-(4-methyl-5-oxo-2,5-dihydrofuran-3-yl)-3-(piperidin-4-yl)pyrrolidin-2-one AND (S)-1-(4-methyl-5-oxo-2,5-dihydrofuran-3-yl)-3-(piperidin-4-yl)pyrrolidin-2-one Step E: tert-butyl 4-(1-(4-methyl-5-oxo-2,5-dihydrofuran-3-yl)-2-oxopyrrolidin-3-yl)piperidine-1-carboxylate A mixture of tert-butyl 4-(2-oxopyrrolidin-3-yl)piperidine-1-carboxylate (100 mg, 0.94 mmol), 4-methyl-5-oxo-2,5-dihydrofuran-3-yl trifluoromethanesulfonate (106 mg, 0.43 mmol), Pd$_2$(dba)$_3$ (9 mg, 0.01 mmol), Xantphos (17 mg, 0.03 mmol), Cs$_2$CO$_3$ (192 mg, 0.59 mmol) in 6 mL of toluene was heated at 90° C. overnight. The mixture was filtered through Celite, evaporated, the residue was purified by flash chromatography (PE:EtOAc=8:1 to 2:1) to give a mixture of two enantiomers which were separated by SFC: Column: Chiralcel OJ-H 250×4.6 mm I.D., 5 um; Mobile phase: methanol (0.05% DEA) in CO$_2$ from 5% to 40%; Flow rate: 2.35 mL/min; Wavelength: 220 nm; $^1$H-NMR (400 MHz, CDCl$_3$) δ ppm 5.30 (d, J=1.6 Hz, 1H), 5.20 (d, J=1.2 Hz, 1H), 4.10-4.20 (m, 2H), 3.95-4.05 (m, 1H), 3.92 (s, 1H), 2.67 (s, 2H), 2.50 (s, 1H), 2.15-2.25 (m, 1H), 1.90-2.05 (m, 5H), 1.80 (t, J=3.2 Hz, 1H), 1.53 (s, 3H), 1.40-1.45 (s, 9H).

Step F: 1-(4-methyl-5-oxo-2,5-dihydrofuran-3-yl)-3-(piperidin-4-yl)pyrrolidin-2-one 4-(1-(4-Methyl-5-oxo-2,5-dihydrofuran-3-yl)-2-oxopyrrolidin-3-yl)piperidine-1-carboxylate (first peak in SFC, 100 mg, 0.28 mmol) was dissolved in 4 mL of EtOAc and treated with 6 mL of 4 M HCl/EtOAc. The mixture was then stirred at r.t. overnight, and then concentrated to afford the title compound (49A) as a single enantiomer. Similarly, the opposite enantiomer (49B) was obtained from the second peak coming from SFC separation of the precursor using 4 M HCl/EtOAc. The absolute stereochemistry of each product was not established; however, both enantiomers were useful for preparing ROMK inhibitors.

Intermediates 50A and 50B (Two Single Enantiomers)

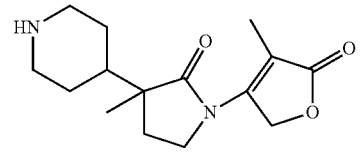 [SMILES: CC1=C(N2CCC(C)(C3CCNCC3)C2=O)COC1=O]

(R)-3-methyl-1-(4-methyl-5-oxo-2,5-dihydrofuran-3-yl)-3-(piperidin-4-yl)pyrrolidin-2-one and (S)-3-methyl-1-(4-methyl-5-oxo-2,5-dihydrofuran-3-yl)-3-(piperidin-4-yl)pyrrolidin-2-one Step E: tert-butyl 4-(3-methyl-1-(4-methyl-5-oxo-2,5-dihydrofuran-3-yl)-2-oxopyrrolidin-3-yl)piperidine-1-carboxylate A mixture of tert-butyl 4-(3-methyl-2-oxopyrrolidin-3-yl)piperidine-1-carboxylate (920 mg, 3.26 mmol), 4-methyl-5-oxo-2,5-dihydrofuran-3-yl trifluoromethanesulfonate (1.04 g, 4.22 mmol), Pd$_2$(dba)$_3$ (159 mg, 0.163 mmol) and Xantphos (377 mg, 0.652 mmol) in toluene (30 mL) was added Cs$_2$CO$_3$(3.19 g, 9.79 mmol), the resulting mixture was heated to reflux and stirred for 16 hours under N$_2$ protection. The mixture was cooled, filtered and concentrated; the residue was purified on silica gel, eluted with PE/EtOAc from 8/1 to 2/1 to get the target products which were separated by SFC chiral chromatography: Column: Chiralpak AD-H 250×4.6 mm I.D., 5 um; Mobile phase: methanol (0.05% DEA) in CO$_2$ from 5% to 40%; Flow rate: 2.35 mL/min; Wavelength: 220 nm. $^1$H-NMR (400 MHz, CDCl$_3$) δ ppm 5.32-5.18 (m, 2H), 4.15-4.09 (m, 2H), 3.98-3.94 (m, 2H), 2.67 (s, 2H), 2.21-2.20 (m, 1H), 2.04 (s, 3H), 1.84-1.71 (m, 4H), 1.59 (s, 9H), 1.50 (s, 1H), 1.27-1.13 (m, 4H).

Step F: 3-methyl-1-(4-methyl-5-oxo-2,5-dihydrofuran-3-yl)-3-(piperidin-4-yl)pyrrolidin-2-one To a suspension of tert-butyl 4-(3-methyl-1-(4-methyl-5-oxo-2,5-dihydrofuran-3-yl)-2-oxopyrrolidin-3-yl)piperidine-1-carboxylate (second eluting in SFC chiral chromatography from Step A, 190 mg, 0.50 mmol) in EtOAc (2 mL) was added HCl/EtOAc (4 M, 2.5 mL), the resulting mixture was stirred at room temperature for 1 h. The mixture was concentrated to afford the title compound 50B. Similarly, the opposite enantiomer (50A) was obtained from the second peak coming from SFC separation of the precursor using 4 M HCl/EtOAc. The absolute stereochemistry of each product was not established; however, both enantiomers were useful for preparing ROMK inhibitors.

Intermediates 51A and 51B (Two Single Enantiomers)

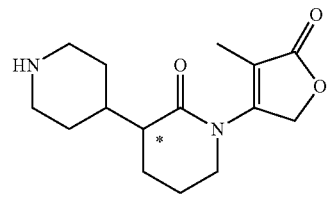 [SMILES: CC1=C(N2CCCC(C3CCNCC3)C2=O)COC1=O]

(R)-1-(4-methyl-5-oxo-2,5-dihydrofuran-3-yl)-[3,4'-bipiperidin]-2-one AND (S)-1-(4-methyl-5-oxo-2,5-dihydrofuran-3-yl)-[3,4'-bipiperidin]-2-one Step A: tert-butyl 1-(4-methyl-5-oxo-2,5-dihydrofuran-3-yl)-2-oxo-[3,4'-bipiperidine]-1'-carboxylate To a solution of tert-butyl 2-oxo-[3,4'-bipiperidine]-1'-carboxylate (270 mg, 0.96 mmol), 4-methyl-5-oxo-2,5-dihydrofuran-3-yl trifluoromethanesulfonate (351 mg, 1.43 mmol) in 18 mL of toluene was added $Pd_2(dba)_3$ (46 mg, 0.05 mmol) and Xantphos (56 mg, 0.10 mmol) under $N_2$ atmosphere, followed by $Cs_2CO_3$ (624 mg, 1.92 mmol), the resulting mixture was heated at 100° C. overnight, then cooled to room temperature, filtered and concentrated, the residue was purified by flash chromatography (60% ethyl acetate in PE) to afford the title compound. The two enantiomers were separated by SFC chiral chromatography (faster eluting and slower eluting enantiomers were obtained): Column: Chiralpak AD-3 150×4.6 mm I.D., 3 um; Mobile phase: methanol (0.05% DEA) in $CO_2$ from 5% to 40%; Flow rate: 2.5 mL/min; Wavelength: 254 nm. $^1$H-NMR (400 MHz, $CDCl_3$) δ ppm 5.20 (d, J=17 Hz, 1H), 5.00 (d, J=17 Hz, 1H), 4.25-4.05 (br, 2H), 3.80-3.65 (m, 2H), 2.77-2.62 (m, 2H), 2.50-2.42 (m, 1H), 2.35-2.22 (m, 1H), 2.08-2.03 (m, 1H), 1.95 (s, 3H), 1.94-1.80 (m, 2H), 1.68-1.52 (m, 3H), 1.41-1.22 (m, 2H).

Step F: 1-(4-methyl-5-oxo-2,5-dihydrofuran-3-yl)-[3,4'-bipiperidin]-2-one

To a solution of tert-butyl 1-(4-methyl-5-oxo-2,5-dihydrofuran-3-yl)-2-oxo-[3,4'-bipiperidine]-1'-carboxylate (first eluting in SFC chromatography in Step A, 150 mg, 0.4 mmol) in 2 mL of EtOAc was added 2 mL of HCl/EtOAc, the mixture was stirred at room temperature for 3 h, and then concentrated to afford the title compound as a single enantiomer 51A. Similarly, the slower eluting product from Step A could be converted to the enantiomeric title compound (51B) using HCl. The absolute stereochemistry of each product was not established; however, both enantiomers were useful for preparing ROMK inhibitors.

Intermediates 52A and 52B (Two Single Enantiomers)

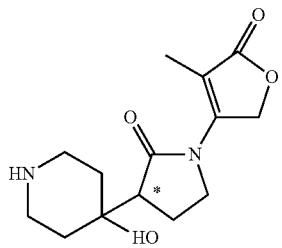 [SMILES: CC1=C(N2CCC(C3(O)CCNCC3)C2=O)COC1=O]

(R)-3-(4-hydroxypiperidin-4-yl)-1-(4-methyl-5-oxo-2,5-dihydrofuran-3-yl)pyrrolidin-2-one and (R)-3-(4-hydroxypiperidin-4-yl)-1-(4-methyl-5-oxo-2,5-dihydrofuran-3-yl)pyrrolidin-2-one Step A: tert-butyl 4-hydroxy-4-(1-(4-methyl-5-oxo-2,5-dihydrofuran-3-yl)-2-oxopyrrolidin-3-yl)piperidine-1-carboxylate To a solution of tert-butyl 4-hydroxy-4-(2-oxopyrrolidin-3-yl)piperidine-1-carboxylate (2.00 g, 7.0 mmol), 4-methyl-5-oxo-2,5-dihydrofuran-3-yl trifluoromethanesulfonate (2.25 g, 9.2 mmol) in 40 mL, of toluene was added $Pd_2(dba)_3$ (322 mg, 0.35 mmol) and Xantphos (404 mg, 0.7 mmol) under $N_2$ atmosphere, followed by $Cs_2CO_3$ (4.58 g, 14 mmol), the resulting mixture was heated at 100° C. overnight, then cooled to room temperature, filtered and concentrated, the residue was purified by flash chromatography (PE:EtOAc from 1:1 to 1:4) to afford the product which was separated to provide two single enantiomers (faster and slower eluting) by SFC chiral chromatiography: Column: Chiralpak AD-3 150×4.6 mm I.D., 3 um; Mobile phase: iso-propanol (0.05% DEA) in $CO_2$ from 5% to 40%; Flow rate: 2.5 mL/min; Wavelength: 254 nm. $^1$H-NMR (400 MHz, $CDCl_3$) δ ppm 5.32-5.12 (m, 2H), 4.05-3.88 (m, 3H), 3.50 (s, 1H), 3.16 (br, 2H), 2.72-2.51 (m, 1H), 2.32-2.22 (m, 1H), 2.04 (s, 4H), 1.78-1.45 (m, 13H).

Step B: 3-(4-hydroxypiperidin-4-yl)-1-(4-methyl-5-oxo-2,5-dihydrofuran-3-yl)pyrrolidin-2-one To a solution of tert-butyl 4-hydroxy-4-(1-(4-methyl-5-oxo-2,5-dihydrofuran-3-yl)-2-oxopyrrolidin-3-yl)piperidine-1-carboxylate (single enantiomer faster eluting from Step A, 100 mg, 0.26 mmol) in 1 mL of EtOAc was added 1 mL of HCl/EtOAc, the mixture was stirred at room temperature for 3 h, and then concentrated to afford the title compound as a single enantiomer 52A. Similarly, the slower eluting product from Step A could be converted to the enantiomeric title compound (52B) using HCl. The absolute stereochemistry of each product was not established; however, both enantiomers were useful for preparing ROMK inhibitors.

Intermediate 53

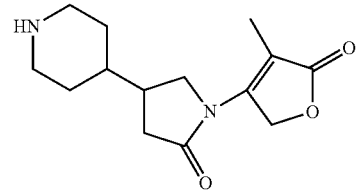 [SMILES: CC1=C(N2CC(C3CCNCC3)CC2=O)COC1=O]

1-(4-methyl-5-oxo-2,5-dihydrofuran-3-yl)-4-(piperidin-4-yl)pyrrolidin-2-one

Step A: tert-butyl 4-(1-(4-methyl-5-oxo-2,5-dihydrofuran-3-yl)-5-oxopyrrolidin-3-yl)piperidine-1-carboxylate The mixture of tert-butyl 4-(5-oxopyrrolidin-3-yl)piperidine-1-carboxylate (500 mg, 1.87 mmol), 4-methyl-5-oxo-2,5-dihydrofuran-3-yl trifluoromethanesulfonate (504 mg, 2.04 mmol), Xantphos (108 mg, 0.187 mmol), $Pd_2(dba)_3$ (86 mg, 0.094 mmol) and $Cs_2CO_3$ (909.5 mg, 2.8 mmol) in toluene (5 mL) was stirred at 110° C. overnight under $N_2$. The mixture was filtered through celite, concentrated and purified on silica gel eluted with PE/EA=1/3 to afford the title compound.

Step B: 1-(4-methyl-5-oxo-2,5-dihydrofuran-3-yl)-4-(piperidin-4-yl)pyrrolidin-2-one The mixture of tert-butyl 4-(1-(4-methyl-5-oxo-2,5-dihydrofuran-3-yl)-5-oxopyrrolidin-3-yl)piperidine-1-carboxylate (160 mg, 0.44 mmol) in DCM: TFA (1:1, 4 mL) was stirred at ambient temperature for 1 hour. The mixture was concentrated to give the title compound.

Intermediate 54

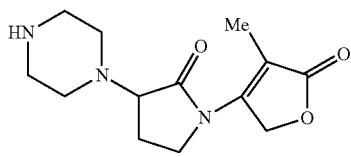 [SMILES: CC1=C(N2CCC(N3CCNCC3)C2=O)COC1=O]

1-(4-methyl-5-oxo-2,5-dihydrofuran-3-yl)-3-(piperazin-1-yl)pyrrolidin-2-one

The title compound, as a mixture of two enantiomers, was prepared in two steps in an analogous fashion to that described for 1-(4-methyl-5-oxo-2,5-dihydrofuran-3-yl)-4-(piperidin-4-yl)pyrrolidin-2-one Intermediate 54, immediately above) starting from tert-butyl 4-(2-oxopyrrolidin-3-yl)piperazine-1-carboxylate and 4-methyl-5-oxo-2,5-dihydrofuran-3-yl trifluoromethanesulfonate. LC/MS: [(M+1)]$^+$=266.

Intermediate 55

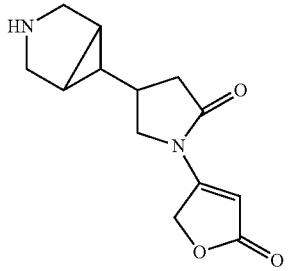 [SMILES: O=C1C=C(N2CC(C3C4CNCC43)CC2=O)CO1]

4-(3-azabicyclo[3.1.0]hexan-6-yl)-1-(5-oxo-2,5-dihydrofuran-3-yl)pyrrolidin-2-one Step A: benzyl 6-formyl-3-azabicyclo[3.1.0]hexane-3-carboxylate To an ice-cooled DCM (10 ml) solution of benzyl 6-(hydroxymethyl)-3-azabicyclo[3.1.0]hexane-3-carboxylate (890 mg, 3.60 mmol) was added Dess-Martin Periodinane (1679 mg, 3.96 mmol) portionwise over a period of 20 minutes. After addition was completed, the reaction mixture was allowed to warm to ambient temperature. At the 2 hour point, another 0.5 equivalents of Dess-Martin was added. After 30 minutes, the reaction was complete. The mixture was quenched by addition of 1:1 solution of aqueous sodium bicarbonate and aqueous sodium thiosulfate (allow biphasic mixture to sit for ~30 minutes). The aqueous layer was extracted with DCM (3×10 mL). The combined organic layers were then dried over sodium sulfate, filtered, concentrated in vacuo and purified via MPLC (0-100% EtOAc/Hex) to afford benzyl 6-formyl-3-azabicyclo[3.1.0]hexane-3-carboxylate.

Step B: (E)-benzyl 6-(3-methoxy-3-oxoprop-1-en-1-yl)-3-azabicyclo[3.1.0]hexane-3-carboxylate In a microwave vial a toluene (10 mL) solution of benzyl 6-formyl-3-azabicyclo[3.1.0]hexane-3-carboxylate (690 mg, 2.81 mmol) and methyl (triphenylphosphoranylidene)acetate (1223 mg, 3.66 mmol) was heated to 1.00° C. for 1.5 hours. The reaction mixture was cooled to ambient temperature, concentrated in vacuo and purified via MPLC (0-100% EtOAc/Hex) to afford the title compound.

Step C: benzyl 6-(4-methoxy-1-nitro-4-oxobutan-2-yl)-3-azabicyclo[3.1.01]hexane-3-carboxylate To a THF (6 mL) solution of (E)-benzyl 6-(3-methoxy-3-oxoprop-1-en-1-yl)-3-azabicyclo[3.1.0]hexane-3-carboxylate (773 mg, 2.57 mmol) was added nitromethane (0.207 mL, 3.85 mmol) and then TBAF (2.77 mL, 2.77 mmol). The reaction was heated to 70° C. for 2 hours after which the mixture was cooled to ambient temperature, concentrated in vacuo and purified via MPLC (0-100% EtOAc/Hex) to afford the title compound.

Step D: benzyl 6-(1-amino-4-methoxy-4-oxobutan-2-yl)-3-azabicyclo[3.1.01]hexane-3-carboxylate To an ice-cooled acetic acid (7.50 mL) water (7.50 mL) mixture of benzyl 6-(4-methoxy-1-nitro-4-oxobutan-2-yl)-3-azabicyclo[3.1.0]hexane-3-carboxylate (670 mg, 1.85 mmol) was added zinc (3020 mg, 46.2 mmol) in 500 mg portions every 30 minutes. At about ~15 equivalents, the reaction mixture was warmed to ambient temperature and stirred for an additional 30 minutes. The reaction was complete. The reaction mixture was filtered over a pad of celite and washed with ~20 mL of ethyl acetate. The organics were then rotovapped off and the aqueous layer was made basic by addition of solid sodium bicarbonate. The basic aqueous layer was then extracted with 30% IPA/chloroform (3×10 mL). The combined organic layers were then dried over sodium sulfate, filtered, concentrated in vacuo to afford the title compound which was used without further purification.

Step E: benzyl 6-(5-oxopyrrolidin-3-yl)-3-azabicyclo[3.1.0]hexane-3-carboxylate

To methanol (10 mL) solution of benzyl 6-(1-amino-4-methoxy-4-oxobutan-2-yl)-3-azabicyclo[3.1.0]hexane-3-carboxylate (570 mg, 1.72 mmol) was added potassium carbonate (237 mg, 1.72 mmol). The reaction mixture was allowed to stir at ambient temperature for 3 hours after which the mixture was concentrated in vacuo. Reverse phase Gilson purfication afforded the title compound.

Step F: benzyl 6-(5-oxo-1-(5-oxo-2,5-dihydrofuran-3-yl)pyrrolidin-3-yl)-3-azabicyclo[3.1.0]hexane-3-carboxylate 4-Bromofuran-2(5H)-one (195 mg, 1.20 mmol), bis(dibenzylideneacetone)palladium (28.7 mg, 0.050 mmol), 4,5-Bis(diphenylphosphino)-9,9-dimethylxanthene (87 mg, 0.150 mmol), and cesium carbonate (488 mg, 1.50 mmol) were combined in a microwave vial and benzyl 6-(5-oxopyrrolidin-3-yl)-3-azabicyclo[3.1.0]hexane-3-carboxylate (300 mg, 1.00 mmol) was added as a solution in toluene (8 mL). The vessel was purged with nitrogen and degassed for 10 minutes. Then the mixture was heated at 90° C., monitoring by LC/MS. When the reaction was judged to be complete by LC/MS, the mixture was filtered through celite, washing with ethyl acetate. The filtrate was concentrated and the crude product was purified by MPLC using a gradient of ethyl acetate/hexanes (40 g silica column). The title compound was obtained.

Step G: 4(3-azabicyclo[3.1.0]hexan-6-yl)-1-(5-oxo-2,5-dihydrofuran-3-yl)pyrrolidin-2-one To a palladium on carbon (29.0 mg, 0.027 mmol) slurry in DCM (10 ml) was added benzyl 6-(5-oxo-1-(5-oxo-2,5-dihydrofuran-3-yl)pyrrolidin-3-yl)-3-azabicyclo[3.1.0]hexane-3-carboxylate (327 mg, 1.089 mmol) as a methanol (5.00 mL) solution. The reaction was placed under balloon pressure hydrogen (vac purge 3 times) for 15 hours at ambient temperature. After 15 hours, the reaction mixture was filtered over a pad of celite, washed ~20 mL of DCM, concentrated in vacuo and purified via MPLC (0-100% EtOAc/Hex, 10% methanol/DCM then 100% methanol) to afford the title compound. LC/MS: [(M+1)]$^+$=249.

Intermediate 56

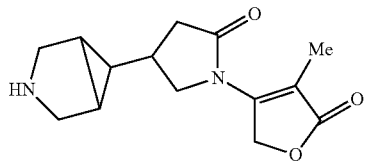 [SMILES: CC1=C(N2CC(C3C4CNCC43)CC2=O)COC1=O]

4-(3-azabicyclo[3.1.0]hexan-6-yl)-1-(4-methyl-5-oxo-2,5-dihydrofuran-3-yl)pyrrolidin-2-one The title compound was prepared in an analogous fashion to that described for 4-(3-azabicyclo[3.1.0]hexan-6-yl)-1-(5-oxo-2,5-dihydrofuran-3-yl)pyrrolidin-2-one (Intermediate 56, immediately above) except 4-methyl-5-oxo-2,5-dihydrofuran-3-yl trifluoromethanesulfonate was used in place of 4-bromofuran-2(5H)-one in Step F. LC/MS: [(M+1)]$^+$=263.

Intermediate 57

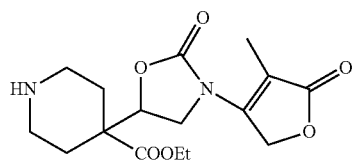 [SMILES: CCOC(=O)C1(C2CN(C3=C(C)C(=O)OC3)C(=O)O2)CCNCC1]

ethyl 4-(3-(4-methyl-5-oxo-2,5-dihydrofuran-3-yl)-2-oxooxazolidin-5-yl)piperidine-4-carboxylate Step A: 1-tert-Butyl 4-ethyl 4-(2-((tert-butoxycarbonyl)amino)-1-hydroxyethyl)piperidine-1,4-dicarboxylate To a solution of LDA (prepared by adding n-butyllithium (20 mL, 49.3 mmol) to diisopropylamine (5.16 mg, 51.0 mmol) in THF (40 mL) at 0° C., stir for 30 min) was added 1-tert-butyl 4-ethyl piperidine-1,4-dicarboxylate (4.00 g, 16.4 mmol) in TMEDA (15 mL, 99 mmol) dropwise via syringe pump at ~78° C. for 10 min. The mixture was stirred at the same temperature for 30 min, tert-butyl (2-oxoethyl)carbamate (8.11 g, 51.0 mmol) in THF (20 mL) was added slowly by syringe pump for 15 min. The mixture was stirred at −78° C. for 30 min, quenched with saturated NH$_4$Cl at −78° C., warmed up to rt and diluted with EtOAc (200 mL). The organic layer was separated, the aqueous layer was extracted with EtOAc (100 mL). The combined organic layers were washed with brine, dried (MgSO$_4$), and concentrated. The residue was purified by column chromatography (80 g, silical gel, MeOH/DCM, gradien 0-10%, monitor at 210 nM) to afford the title compound.

Step B: 1-tert-Butyl 4-ethyl 4-(2-oxooxazolidin-5-yl)piperidine-1,4-dicarboxylate To a solution of 1-tert-butyl 4-ethyl 4-(2-((tert-butoxycarbonyl)amino)-1-hydroxyethyl)piperidine-1,4-dicarboxylate (450 mg, 1.08 mmol) in DCM (10 mL) at ~78° C. was added triethylamine trihydrofluoride (0.35 mL, 2.16 mmol), triethylamine (0.15 mL, 1.08 mmol), and (diethylamino)difluorosulfonium tetrafluoroborate (371 mg, 1.62 mmol). The mixture was stirred overnight while warming up to rt, and quenched with aqueous NaHCO$_3$. The organic layer was separated and the aqeous layer was extracted with DCM (30 mL). The combined organic layers were dried (MgSO$_4$) and purified by preparative TLC (5% MeOH/DCM as eluent) to give the title compound. LC/MS: [(M+23)]$^+$=365.

Step C: 1-tert-Butyl 4-ethyl 4-(3-(4-methyl-5-oxo-2,5-dihydrofuran-3-yl)-2-oxooxazolidin-5-yl)piperidine-1,4-dicarboxylate To a round bottom flask was charged 1-tert-butyl 4-ethyl 4-(2-oxooxazolidin-5-yl)piperidine-1,4-dicarboxylate (180 mg, 0.526 mmol), 4-methyl-5-oxo-2,5-dihydrofuran-3-yl trifluoromethanesulfonate (155 mg, 0.631 mmol), Pd$_2$(dba)$_3$ (12.0 mg, 0.013 mmol), XantPhos (22.8 mg, 0,039 mmol), and cesium carbonate (343 mg, 1.05 mmol). The flask was equipped with condenser, vacuumed and back filled with N$_2$ and filled with Dioxane (2.1 mL). The reaction mixture was heated at 90° C. overnight, and filtered through celite. The filtrate was evaporated to give the crude product, which was purified by column chromatography (0-10% MeOH/DCM as eluent) to give the title compound. LC/MS: [(M+1-56)]$^+$=383.

Step D: ethyl 4-(3-(4-methyl-5-oxo-2,5-dihydrofuran-3-yl)-2-oxooxazolidin-5-yl)piperidine-4-carboxylate 1-tert-Butyl 4-ethyl 4-(3-(4-methyl-5-oxo-2,5-dihydrofuran-3-yl)-2-oxooxazolidin-5-yl)piperidine-1,4-dicarboxylate (230 mg, 0.525 mmol) in DCM (2.6 mL) was treated with TFA (1.2 mL, 15.7 mmol) at 0° C. to free Boc and give TFA salt. Then a 2 g Bond Elut SCX (ion exchange) column was first rinsed with MeOH, load sample with MeOH, washed with MeOH dropwise to remove TFA, finally rinsed with 2N NH$_3$/MeOH to get the title compound as a free amine. LC/MS: [(M+1)]$^+$=339

Intermediate 58

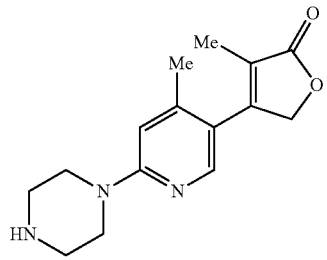 [SMILES: CC1=C(c2cnc(N3CCNCC3)cc2C)COC1=O]

3-methyl-4-(4-methyl-6-(piperazin-1-yl)pyridin-3-yl)furan-2(5H)-one

Step A: tert-butyl 4-(5-bromo-4-methylpyridin-2-yl)piperazine-1-carboxylate 2,5-dibromo-3-methylpyridine (998 mg, 3.98 mmol), 1-boc-piperazine (570 mg, 3.06 mmol) were combined in a microwave vial, dry toluene (10 ml) was added to that followed by sodium tert-butoxide (441 mg, 4.59 mmol), 4,5-bis(diphenylphosphino)-9,9-dimethylxanthene (106 mg, 0.184 mmol) and tris(dibenzylideneacetone)dipalladium(0) (56.0 mg, 0.061 mmol). The resulting mixture was purged with nitrogen and then heated at 100° C. for 3 hours. After cooling to room temperature, the reaction mixture was diluted with EtOAc and washed with water. Organic layer was dried over anhydrous $Na_2SO_4$, filtered, concentrated and purified by silica gel column chromatography using (0-30)% EtOAc/Hexanes as mobile phase and the product, tert-butyl 4-(5-bromo-4-methylpyridin-2-yl)piperazine-1-carboxylate, was isolated.

Step B: tert-butyl 4-(4-methyl-5-(4,4,5,5-tetramethyl-1,3,2-dioxaborolan-2-yl)pyridin-2-yl)piperazine-1-carboxylate tert-butyl 4-(5-bromo-4-methylpyridin-2-yl)piperazine-1-carboxylate (0.80 g, 2.331 mmol) was mixed with bis(pinacolato)diboron (0.710 g, 2.80 mmol) and potassium acetate (0.686 g, 6.99 mmol) in 1,4-dioxane (18 mL). After degassing with $N_2$ for 10 minutes, [1,1'-bis(diphenylphosphino)ferrocene]dichloropalladium(II) (0.085 g, 0.117 mmol) was added and the resulting reaction mixture was heated overnight at 80° C. The reaction mixture was then cooled to room temperature, filtered over celite and concentrated to get the crude product, tert-butyl 4-(4-methyl-5-(4,4,5,5-tetramethyl-1,3,2-dioxaborolan-2-yl)pyridin-2-yl)piperazine-1-carboxylate, which was taken to the next step without purification.

Step C: tert-butyl 4-(4-methyl-5-(4-methyl-5-oxo-2,5-dihydrofuran-3-yl)pyridin-2-yl)piperazine-1-carboxylate In a microwave vial, tert-butyl 4-(4-methyl-5-(4,4,5,5-tetramethyl-1,3,2-dioxaborolan-2-yl)pyridin-2-yl)piperazine-1-carboxylate (0.9 g, 2.231 mmol) was mixed with 4-methyl-5-oxo-2,5-dihydrofuran-3-yl trifluoromethanesulfonate (0.824 g, 3.35 mmol) in tetrahydrofuran (8 ml) and sodium bicarbonate and water (8 ml). [1,1'-bis(diphenylphosphino)ferrocene]dichloropalladium(II) (0.082 g, 0.112 mmol) was added to the mixture and the resulting reaction mixture was heated for 10 minutes at 120° C. under microwave condition at high absorption. After cooling down to rt, reaction was diluted by adding EtOAc and water. After separation, aqueous layer was extracted with EtOAc (2×). Combined organic layers were dried over $MgSO_4$ filtered, concentrated to get the crude product that was purified by silica gel column chromatography using (20-80)% EtOAc/Hexanes as mobile phase and the product, tert-butyl 4-(4-methyl-5-(4-methyl-5-oxo-2,5-dihydrofuran-3-yl)pyridin-2-yl)piperazine-1-carboxylate, was isolated.

Step D: 3-methyl-4-(4-methyl-6-(piperazin-1-yl)pyridin-3-yl)furan-2(5H)-one tert-butyl 4-(4-methyl-5-(4-methyl-5-oxo-2,5-dihydrofuran-3-yl)pyridin-2-yl)piperazine-1-carboxylate was dissolved in DCM and treated with TFA. The reaction was monitored by LC-MS until completion whereupon the volatiles were removed under vacuum to afford the title compound.

Intermediate 59

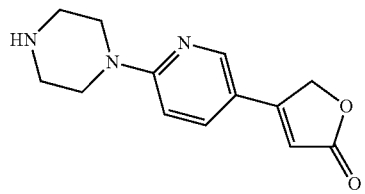 [SMILES: O=C1C=C(c2ccc(N3CCNCC3)nc2)CO1]

4-(6-(piperazin-1-yl)pyridin-3-yl)furan-2(5H)-one

Step A: tert-butyl 4-(5-bromopyridin-2-yl)piperazine-1-carboxylate

To a solution of tert-butyl piperazine-1-carboxylate (1.00 g, 5.37 mmol) in DMF (2 ml) and THF (10 ml) in a 20 mL microwave vial was added DIEA (1.125 mL, 6.44 mmol) and the mixture was heated at 160° C. for 100 minutes. The solvent was removed after cooling to room temperature, the residue was dissolved in EtOAc (50 ml) and was washed with water (30 ml) followed by Brine (20 ml). The organic layer was dried over anhydrous $Na_2SO_4$, filtered and concentrated in vacuo. The residue was purified by silica gel column chromatography (125 g pre-packed column) using (0-100)% EtOAc/Hexanes as mobile phase and the title compound was isolated

Steps B through D: 4-(6-(piperazin-1-yl)pyridin-3-yl)furan-2(5H)-one

The title compound was prepared in an analogous fashion as described for Intermediate 58 (Steps B-D), immediately above, starting from tert-butyl 4-(5-bromopyridin-2-yl)piperazine-1-carboxylate. LC-MS [M+1]$^+$246.1

The Intermediates in Table 3 were prepared in an analogous fashion to the methods described for 3-methyl-4-(4-methyl-6-(piperazin-1-yl)pyridin-3-yl)furan-2(5H)-one (INTERMEDIATE 58) and 4-(6-(piperazin-1-yl)pyridin-3-yl)furan-2(5H)-one (INTERMEDIATE 59) using either 4-methyl-5-oxo-2,5-dihydrofuran-3-yl trifluoromethanesulfonate or commercially available 4-bromofuran-2(5H)-one and the commercially available starting materials shown.

TABLE 3

| Intermediate No. | Starting material | Product Intermediate | LC-MS [M + 1]+ |
|---|---|---|---|
| 60 | | | 260 |
| 61 | | | 261 |
| 62 | | | 291 |
| 63 | | | 290 |

Intermediate 64

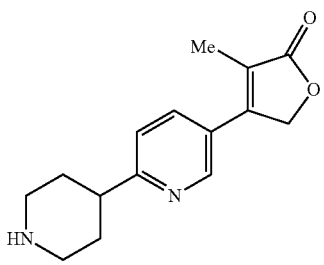 [SMILES: CC1=C(c2ccc(C3CCNCC3)nc2)COC1=O]

3-methyl-4-(6-(piperidin-4-yl)pyridin-3-yl)furan-2 (5H)-one

Step A: tert-butyl 5-chloro-5'6'-dihydro-[2,4'-bipyridine]-1'(2'H)-carboxylate

In a microwave vial, 2-bromo-5-chloropyridine (0.934 g, 4.85 mmol) was mixed with tert-butyl 4-(4,4,5,5-tetramethyl-1,3,2-dioxaborolan-2-yl)-5,6-dihydropyridine-1(2H)-carboxylate (1.0 g, 3.23 mmol) in tetrahydrofuran (8 ml) and sodium bicarbonate (0,543 g, 6.47 mmol) and water (8 mL). [1,1'-bis(diphenylphosphino)ferrocene]dichloropalladium (II) (0.118 g, 0.162 mmol) was added. The reaction was heated for 10 minutes at 120° C. in a microwave at high absorption. After cooling down to rt, reaction was diluted by adding EtOAc and water. After separation, aqueous layer was extracted with EtOAc (2×). Combined organic layers were dried over MgSO₄, filtered, concentrated to get the crude product that was purified by silica gel column chromatography using (20-80)% EtOAc— Hexanes as mobile phase and the title compound was isolated.

Step B: tert-butyl 5-(4,4,5,5-tetramethyl-1,3,2-dioxaborolan-2-yl)-5',6'-dihydro-[2,4'-bipyridine]-1' (2'H)-carboxylate tert-butyl 5-chloro-5'6'-dihydro-[2,4'-bipyridine]-1'(2'H)-carboxylate (410 mg, 1.391 mmol), bis(pinacolato)diboron (1060 mg, 4.17 mmol), 2-dicyclohexylphosphino-2',4',6'-triisopropylbiphenyl (13.26 mg, 0.028 mmol), potassium acetate (410 mg, 4.17 mmol) and tris(dibenzylideneacetone) dipalladium(0) (12.74 mg, 0.014 mmol) were taken up in 1,4-dioxane (8 mL) in a microwave vial and the resulting mixture was degassed in for 10 minutes and then heated at 110° C. for 4 hours. The reaction mixture was then cooled to room temperature, filtered over celite, concentrated and the crude material was taken to the next step.

Step C: tert-butyl 5-(4-methyl-5-oxo-2,5-dihydrofuran-3-yl)-5',6'-dihydro-[2,4'-bipyridine]-1'(2'H)-carboxylate The title compound was prepared from tert-butyl 5-(4,4,5,5-tetramethyl-1,3,2-dioxaborolan-2-yl)-5',6'-dihydro-[2, 4'-bipyridine]-1'(2'H)-carboxylate and 4-methyl-5-oxo-2,5-dihydrofuran-3-yl trifluoromethanesulfonate in an analogous fashion as described for tert-butyl 4-(4-methyl- 5-(4-methyl-5-oxo-2,5-dihydrofuran-3-yl)pyridin-2-yl)piperazine-1-carboxylate INTERMEDIATE 58 (Step C).

Step D: tert-butyl 4-(5-(4-methyl-5-oxo-2,5-dihydrofuran-3-yl)pyridin-2-yl)piperidine-1-carboxylate tert-butyl 5-(4-methyl-5-oxo-2,5-dihydrofuran-3-yl)-5',6'-dihydro-[2,4'-bipyridine]-1'(2'E)-carboxylate (190 mg, 0.533 mmol) was dissolved in methanol (7 mL) and hydrogenated at room temperature at 1 atm. pressure. The reaction mixture was filtered through celite, washed with methanol, concentrated to get the title product.

Step E: 3-methyl-4-(6-(piperidin-4-yl)pyridin-3-yl) furan-2(5H)-one

The title compound was prepared from tert-butyl 4-(5-(4-methyl-5-oxo-2,5-dihydrofuran-3-yl)pyridin-2-yl)piperidine-1-carboxylate in an analogous fashion to that described for 3-methyl-4-(4-methyl-6-(piperazin-1-yl)pyridin-3-yl) furan-2(5H)-one INTERMEDIATE 59 (Step D) using TFA.

Intermediate 65

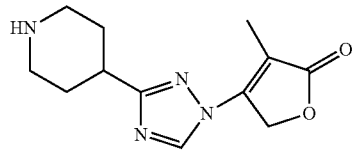 [SMILES: CC1=C(n2cnc(C3CCNCC3)n2)COC1=O]

3-methyl-4-(3-(piperidin-4-yl)-1H-1,2,4-triazol-1-yl) furan-2(5H)-one

Step A: tert-butyl 4-(1H-1,2,4-triazol-3-yl)piperidine-1-carboxylate

To a solution of tert-butyl 4-cyanopiperidine-1-carboxylate (32.75 g, 156 mmol) in MeOH (280 mL) was added a solution of NaOMe (2.50 g, 47 mmol) in 5 mL of MeOH. The resulting mixture was stirred at room temperature for 30 min, and then formohydrazide (9.40 g, 156 mmol) was added. The reaction mixture was heated under reflux for 16 hrs, another batch of NaOMe (2.50 g, 47 mmol) in 5 mL of MeOH and formohydrazide (9.40 g, 156 mmol) were added to the above reaction. The reaction mixture was heated under reflux for 48 hrs. The mixture was cooled and adjusted to pH 6 with AcOH, added water and EtOAc, the organic layer was separated and dried over anhydrous $Na_2SO_4$, filtered and concentrated, the crude product was purified by flash chromatography (DCM:MeOH=60:1 to 10:1) to afford the title compound.

Step B: tert-butyl 4-(1-(4-methyl-5-oxo-2,5-dihydrofuran-3-yl)-1H-1,2,4-triazol-3-yl)piperidine-1-carboxylate To a solution of tert-butyl 4-(1H-1,2,4-triazol-3-yl)piperidine-1-carboxylate (1.00 g, 4.0 mmol), 4-methyl-5-oxo-2,5-dihydrofuran-3-yl) trifluoromethanesulfonate (1.30 g, 5.2 mmol) in 20 mL of toluene was added Pd-118 (200 mg) under $N_2$ atmosphere, followed by $Cs_2CO_3$ (2.60 g, 8.0 mmol), the resulting mixture was heated at 90° C. overnight under $N_2$ atmosphere, then cooled to room temperature, filtered and the solvent was removed under vacuum, the residue was purified by flash chromatography (PE:EtOAc from 2:1 to 1:2) to afford the title compound.

Step C: 3-methyl-4-(3-(piperidin-4-yl)-1H-1,2,4-triazol-1-yl)furan-2(5H)-one

To a solution of tert-butyl 4-(1-(4-methyl-5-oxo-2,5-dihydrofuran-3-yl)-1H-1,2,4-triazol-3-yl)piperidine-1-carboxylate (230 mg, 0.66 mmol) in 3 mL of EtOAc was added 3 mL of HCl/EtOAc, the mixture was stirred at room temperature for 3 h, then concentrated to afford the title compound.

Example 1A

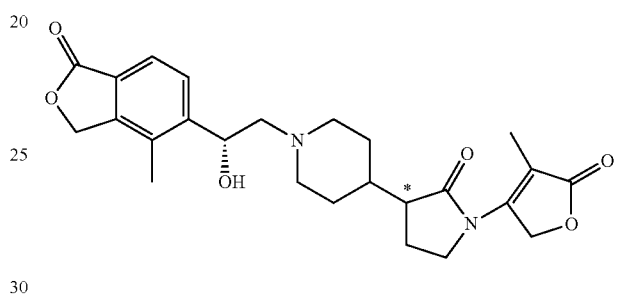

3-(1-((R)-2-hydroxy-2-(4-methyl-1-oxo-1,3-dihydroisobenzofuran-5-yl)ethyl)piperidin-4-yl)-1-(4-methyl-5-oxo-2,5-dihydrofuran-3-yl)pyrrolidin-2-one A mixture of (R)-4-methyl-5-(oxiran-2-yl)isobenzofuran-1(3H)-one (190 mg, 1.0 mmol), 1-(4-methyl-5-oxo-2,5-dihydrofuran-3-yl)-3-(piperidin-4-yl)pyrrolidin-2-one (49A single enantiomer from faster eluting Boc precursor SFC separation) (220 mg, 0.83 mmol) and TEA (0.25 mL, 1.8 mmol) in 10 mL of EtOH was heated at 80° C. for 6 h. The reaction mixture was concentrated and purified by preparative TLC (EtOAc/MeOH=3:1) to afford the title compound as a single enantiomer. $^1$H-NMR (400 MHz, MeOD) δ ppm 7.80 (d J=8.0 Hz, 1H), 7.73 (d, J=8.0 Hz, 1H), 5.47 (m, 3H), 5.27 (d, J=16 Hz, 1H), 5.19 (d, J=16 Hz, 1H), 4.15 (m, 1H), 4.01 (m, 1H), 3.57 (m, 1H), 3.46 (m, 1H), 2.94 (m, 2H), 2.75 (m, 2H), 2.62 (m, 1H), 2.35 (s, 3H), 2.28 (m, 1H), 2.15 (s, 3H), 1.98 (m, 4H), 1.82 (m, 2H).

Example 2A AND 2B

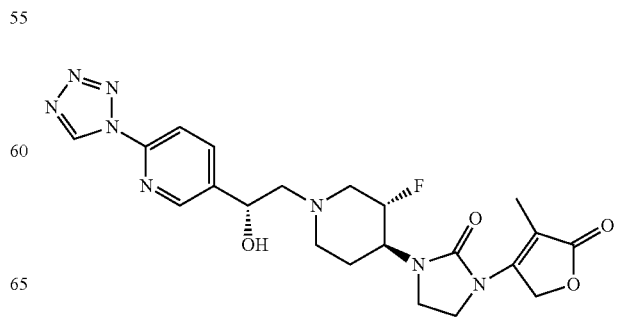

-continued

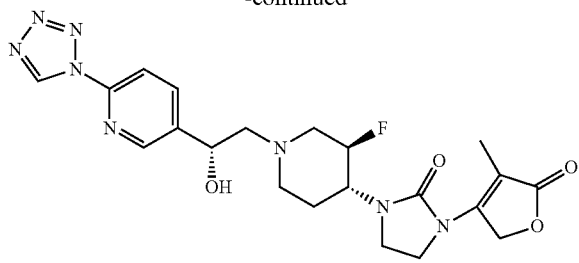

1-((3S,4S)-1-((R)-2-(6-(1H-tetrazol-1-yl)pyridin-3-yl)-2-hydroxyethyl)-3-fluoropiperidin-4-yl)-3-(4-methyl-5-oxo-2,5-dihydrofuran-3-yl)imidazolidin-2-one AND 1-((3R,4R)-1-((R)-2-(6-(1H-tetrazol-1-yl)pyridin-3-yl)-2-hydroxyethyl)-3-fluoropiperidin-4-yl)-3-(4-methyl-5-oxo-2,5-dihydrofuran-3-yl)imidazolidin-2-one To trans-1-(3-fluoropiperidin-4-yl)-3-(4-methyl-5-oxo-2,5-dihydrofuran-3-yl)imidazolidin-2-one (70 mg, 0.247 mmol) in Ethanol (1235 μl) was added (R)-5-(oxiran-2-yl)-2-(1H-tetrazol-1-yl)pyridine (70.1 mg, 0.371 mmol). The reaction mixture was heated at 90° C. overnight. The reaction mixture was evaporated for purification by ISCO (0-10% MeOH/DCM) to provide the product as a free base which was separated to two single diastereomers by SFC chiral chromatography: Column AS-H (2×25 cm), eluent 40% methanol (0.1% DEA)/CO2, 100 bar, flow rate 65 mL/min, detection wavelength 254 nm, injection volume: 1 mL, 13 mg/mL 1:1 DCM:methanol.

Faster eluting isomer 2A: LC-MS (ESI, m/z): [M+1]$^+$473.
Slower eluting isomer 2B: LC-MS (ESI, m/z): [M+1]$^+$ 473.

The Examples in the table below were prepared in an analogous fashion as that described for 3-(1-((R)-2-hydroxy-2-(4-methyl-1-oxo-1,3-di hydroisobenzofuran-5-yl)ethyl)piperidin-4-yl)-1-(4-methyl-5-oxo-2,5-dihydrofuran-3-yl)pyrrolidin-2-one (EXAMPLE 1) and 1-((3S,4S)-1-((R)-2-(6-(1H-tetrazol-1-yl)pyridin-3-yl)-2-hydroxyethyl)-3-fluoropiperidin-4-yl)-3-(4-methyl-5-oxo-2,5-dihydrofuran-3-yl)imidazolidin-2-one AND 1-((3R,4R)-1-((R)-2-(6-(1H-tetrazol-1-yl)pyridin-3-yl)-2-hydroxyethyl)-3-fluoropiperidin-4-yl)-3-(4-methyl-5-oxo-2,5-dihydrofuran-3-yl)imidazolidin-2-one (EXAMPLES 2A and 2B) from the amine and epoxide Intermediates indicated, which were all prepared as described above. In some cases (as in EXAMPLES 2A and 2B) a chiral SFC separation of diastereomers was performed to provide single isomer products.

| # | Intermediates | Structure | LC-MS (ESI, m/z): [M + 1]$^+$ or NMR IUPAC name |
|---|---|---|---|
| 1B | 3B, 49B | 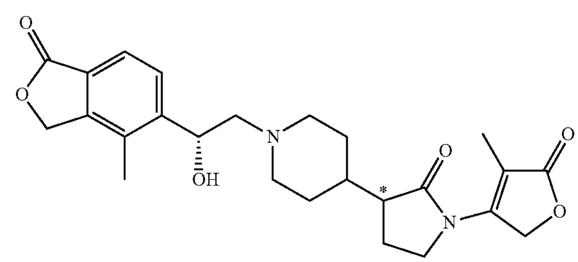 [SMILES: CC1=C(N2CCC(C3CCN(C[C@H](O)c4ccc5c(c4C)COC5=O)CC3)C2=O)COC1=O] | 455 — 3-(1-((R)-2-hydroxy-2-(4-methyl-1-oxo-1,3-dihydroisobenzofuran-5-yl)ethyl)piperidin-4-yl)-1-(4-methyl-5-oxo-2,5-dihydrofuran-3-yl)pyrrolidin-2-one, single diastereomer, absolute stereochemistry on lactam not determined but opposite to Example 1A. |
| 3A | 5A, 49B | 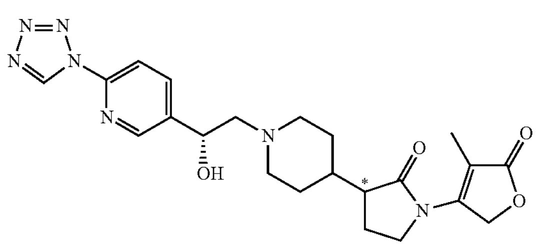 [SMILES: CC1=C(N2CCC(C3CCN(C[C@H](O)c4ccc(-n5cnnn5)nc4)CC3)C2=O)COC1=O] | 454 — 3-(1-((R)-2-(6-(1H-tetrazol-1-yl)pyridin-3-yl)-2-hydroxyethyl)piperidin-4-yl)-1-(4-methyl-5-oxo-2,5-dihydrofuran-3-yl)pyrrolidin-2-one (single diastereomer, stereochemistry on lactam not established) |
| 3B | 5B, 49B | 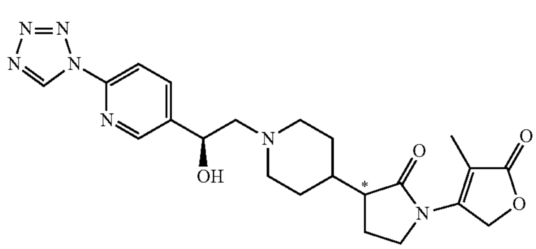 [SMILES: CC1=C(N2CCC(C3CCN(C[C@@H](O)c4ccc(-n5cnnn5)nc4)CC3)C2=O)COC1=O] | 454 — 3-(1-((S)-2-(6-(1H-tetrazol-1-yl)pyridin-3-yl)-2-hydroxyethyl)piperidin-4-yl)-1-(4-methyl-5-oxo-2,5-dihydrofuran-3-yl)pyrrolidin-2-one (single diastereomer, stereochemistry on lactam not established) |

-continued

| # | Intermediates | Structure | LC-MS (ESI, m/z): [M + 1]+ or NMR IUPAC name |
|---|---|---|---|
| 3C | 5A, 49A | 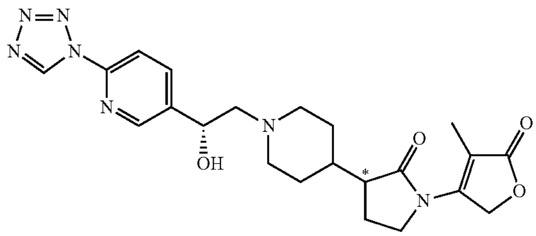 [SMILES: CC1=C(N2CCC(C3CCN(C[C@H](O)c4ccc(-n5cnnn5)nc4)CC3)C2=O)COC1=O] | 454 3-(1-((R)-2-(6-(1H-tetrazol-1-yl)pyridin-3-yl)-2-hydroxyethyl)piperidin-4-yl)-1-(4-methyl-5-oxo-2,5-dihydrofuran-3-yl)pyrrolidin-2-one (single diastereomer, stereochemistry on lactam not established, but opposite to 3A) |
| 3D | 5B, 49A | 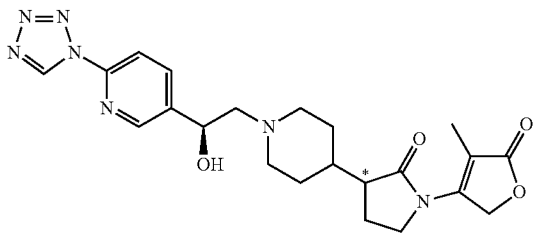 [SMILES: CC1=C(N2CCC(C3CCN(C[C@@H](O)c4ccc(-n5cnnn5)nc4)CC3)C2=O)COC1=O] | 454 3-(1-((S)-2-(6-(1H-tetrazol-1-yl)pyridin-3-yl)-2-hydroxyethyl)piperidin-4-yl)-1-(4-methyl-5-oxo-2,5-dihydrofuran-3-yl)pyrrolidin-2-one (single diastereomer, stereochemistry on lactam not established, but opposite to 3B) |
| 4A | 5A, 36 | 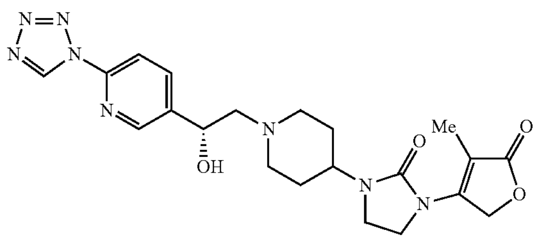 [SMILES: CC1=C(N2CCN(C3CCN(C[C@H](O)c4ccc(-n5cnnn5)nc4)CC3)C2=O)COC1=O] | 455 (R)-1-(1-(2-(6-(1H-tetrazol-1-yl)pyridin-3-yl)-2-hydroxyethyl)piperidin-4-yl)-3-(4-methyl-5-oxo-2,5-dihydrofuran-3-yl)imidazolidin-2-one |
| 4B | 5B, 36 | 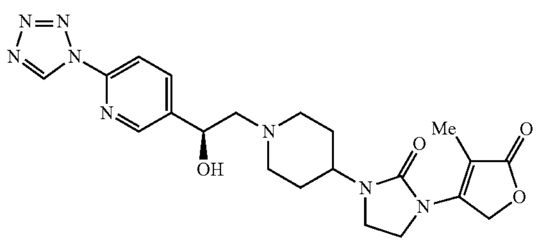 [SMILES: CC1=C(N2CCN(C3CCN(C[C@@H](O)c4ccc(-n5cnnn5)nc4)CC3)C2=O)COC1=O] | 455 (S)-1-(1-(2-(6-(1H-tetrazol-1-yl)pyridin-3-yl)-2-hydroxyethyl)piperidin-4-yl)-3-(4-methyl-5-oxo-2,5-dihydrofuran-3-yl)imidazolidin-2-one |
| 5A | 3B, 55 | Faster eluting isomer from SFC | 439 4-(3-((R)-2-hydroxy-2-(4-methyl-1-oxo-1,3-dihydroisobenzofuran-5-yl)ethyl)-3-azabicyclo[3.1.0]hexan-6-yl)-1-(5-oxo-2,5-dihydrofuran-3-yl)pyrrolidin-2-one; (single diastereomer, trans cyclopropane; stereochemistry on lactam not established) |

-continued

| # | Intermediates | Structure | LC-MS (ESI, m/z): [M + 1]+ or NMR IUPAC name |
|---|---|---|---|
| 5B | 3B, 55 | Slower eluting isomer from SFC | 439 | 4-(3-((R)-2-hydroxy-2-(4-methyl-1-oxo-1,3-dihydroisobenzofuran-5-yl)ethyl)-3-azabicyclo[3.1.0]hexan-6-yl)-1-(5-oxo-2,5-dihydrofuran-3-yl)pyrrolidin-2-one; (single diastereomer, trans cyclopropane; stereochemistry on lactam not established, but opposite to 5A) |
| 6A | 3B, 56 | Faster eluting isomer from SFC | 453 | 4-(3-((R)-2-hydroxy-2-(4-methyl-1-oxo-1,3-dihydroisobenzofuran-5-yl)ethyl)-3-azabicyclo[3.1.0]hexan-6-yl)-1-(4-methyl-5-oxo-2,5-dihydrofuran-3-yl)pyrrolidin-2-one; (single diastereomer, trans cyclopropane; stereochemistry on lactam not established) |
| 6B | 3B, 56 | Slower eluting isomer from SFC | 453 | 4-(3-((R)-2-hydroxy-2-(4-methyl-1-oxo-1,3-dihydroisobenzofuran-5-yl)ethyl)-3-azabicyclo[3.1.0]hexan-6-yl)-1-(4-methyl-5-oxo-2,5-dihydrofuran-3-yl)pyrrolidin-2-one; (single diastereomer, trans cyclopropane; stereochemistry on lactam not established, but opposite to 6A) |
| 7A | 5A, 56 | Faster eluting isomer from SFC | 452 | 4-(3-((R)-2-(6-(1H-tetrazol-1-yl)pyridin-3-yl)-2-hydroxyethyl)-3-azabicyclo[3.1.0]hexan-6-yl)-1-(4-methyl-5-oxo-2,5-dihydrofuran-3-yl)pyrrolidin-2-one; (single diastereomer, trans cyclopropane; stereochemistry on lactam not established) |

| # | Intermediates | Structure | LC-MS (ESI, m/z): [M + 1]+ or NMR IUPAC name |
|---|---|---|---|
| 7B | 5A, 56 | Faster eluting isomer from SFC | 452  4-(3-((R)-2-(6-(1H-tetrazol-1-yl)pyridin-3-yl)-2-hydroxyethyl)-3-azabicyclo[3.1.0]hexan-6-yl)-1-(4-methyl-5-oxo-2,5-dihydrofuran-3-yl)pyrrolidin-2-one; (single diastereomer, trans cyclopropane; stereochemistry on lactam not established, but opposite to 7A)) |
| 8 | 3B, 38 | 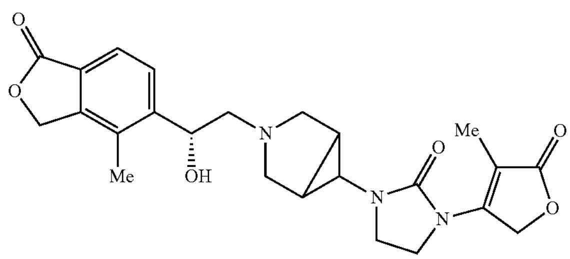 [SMILES: CC1=C(N2CCN(C3C4CN(C[C@H](O)c5ccc6c(c5C)COC6=O)CC43)C2=O)COC1=O] | 454  1-(3-((R)-2-hydroxy-2-(4-methyl-1-oxo-1,3-dihydroisobenzofuran-5-yl)ethyl)-3-azabicyclo[3.1.0]hexan-6-yl)-3-(4-methyl-5-oxo-2,5-dihydrofuran-3-yl)imidazolidin-2-one |
| 9A | 5A, 38 | 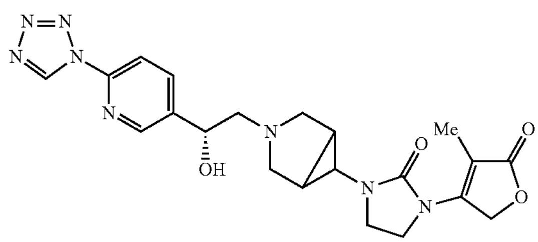 [SMILES: CC1=C(N2CCN(C3C4CN(C[C@H](O)c5ccc(-n6cnnn6)nc5)CC43)C2=O)COC1=O] | 453  1-(3-((R)-2-(6-(1H-tetrazol-1-yl)pyridin-3-yl)-2-hydroxyethyl)-3-azabicyclo[3.1.0]hexan-6-yl)-3-(4-methyl-5-oxo-2,5-dihydrofuran-3-yl)imidazolidin-2-one |
| 9B | 5B, 38 | 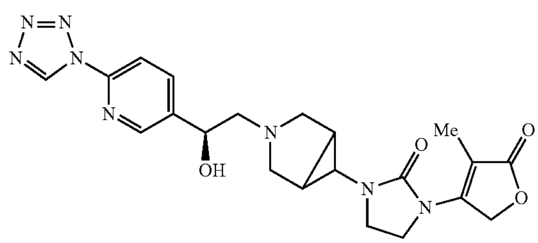 [SMILES: CC1=C(N2CCN(C3C4CN(C[C@@H](O)c5ccc(-n6cnnn6)nc5)CC43)C2=O)COC1=O] | 453  1-(3-((S)-2-(6-(1H-tetrazol-1-yl)pyridin-3-yl)-2-hydroxyethyl)-3-azabicyclo[3.1.0]hexan-6-yl)-3-(4-methyl-5-oxo-2,5-dihydrofuran-3-yl)imidazolidin-2-one |
| 10A | 8A, 38 | 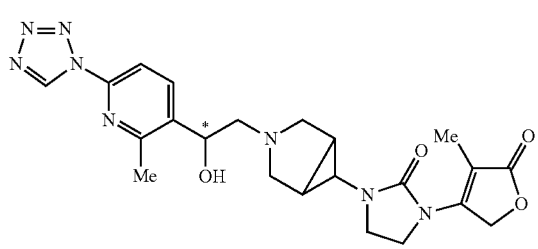 [SMILES: CC1=C(N2CCN(C3C4CN(CC(O)c5ccc(-n6cnnn6)nc5C)CC43)C2=O)COC1=O] | 467  1-(3-(2-hydroxy-2-(2-methyl-6-(1H-tetrazol-1-yl)pyridin-3-yl)ethyl)-3-azabicyclo[3.1.0]hexan-6-yl)-3-(4-methyl-5-oxo-2,5-dihydrofuran-3-yl)imidazolidin-2-one; (single diastereomer; stereochemistry on at hydroxyl substituted carbon not established) |

| # | Intermediates | Structure | LC-MS (ESI, m/z): [M + 1]+ or NMR IUPAC name |
|---|---|---|---|
| 10B | 8B, 38 | 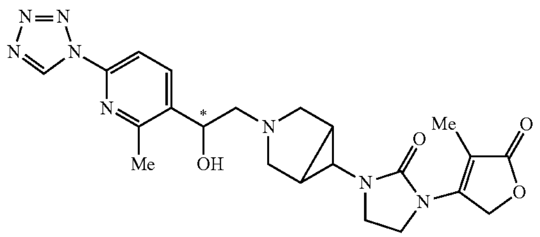 [SMILES: CC1=C(N2CCN(C3C4CN(CC(O)c5ccc(-n6cnnn6)nc5C)CC43)C2=O)COC1=O] | 467 1-(3-(2-hydroxy-2-(2-methyl-6-(1H-tetrazol-1-yl)pyridin-3-yl)ethyl)-3-azabicyclo[3.1.0]hexan-6-yl)-3-(4-methyl-5-oxo-2,5-dihydrofuran-3-yl)imidazolidin-2-one; (single diastereomer; stereochemistry on at hydroxyl substituted carbon not established but opposite to 10A) |
| 11 | 3B, 40 | 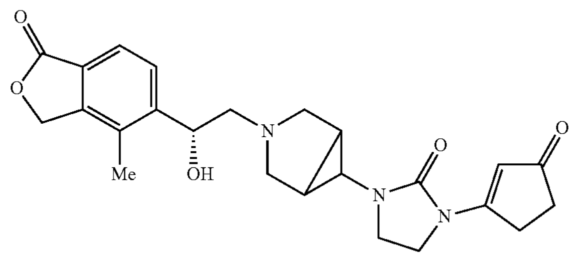 [SMILES: Cc1c([C@@H](O)CN2CC3C(C2)C3N2CCN(C3=CC(=O)CC3)C2=O)ccc2c1COC2=O] | 438 1-(3-((R)-2-hydroxy-2-(4-methyl-1-oxo-1,3-dihydroisobenzofuran-5-yl)ethyl)-3-azabicyclo[3.1.0]hexan-6-yl)-3-(3-oxocyclopent-1-en-1-yl)imidazolidin-2-one |
| 12 | 3B, 36 | 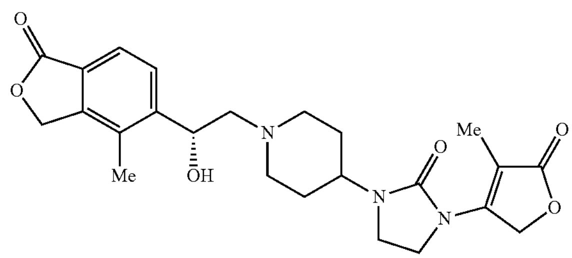 [SMILES: CC1=C(N2CCN(C3CCN(C[C@H](O)c4ccc5c(c4C)COC5=O)CC3)C2=O)COC1=O] | 456 (R)-1-(1-(2-hydroxy-2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one |
| 13A | 8B, 41 | Faster eluting isomer from SFC (chiralpak AS) | 455 1-(1-(2-hydroxy-2-(2-methyl-6-(1H-tetrazol-1-yl)pyridin-3-yl)ethyl)pyrrolidin-3-yl)-3-(4-methyl-5-oxo-2,5-dihydrofuran-3-yl)imidazolidin-2-one; single diastereomer, absolute stereochemistry not established |
| 13B | 8A, 41 | 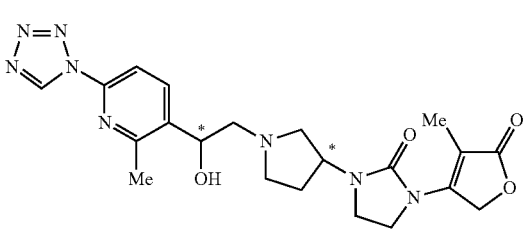 [SMILES: CC1=C(N2CCN(C3CCN(CC(O)c4ccc(-n5cnnn5)nc4C)C3)C2=O)COC1=O] Faster eluting isomer from SFC (chiralcel OJ) | 455 1-(1-(2-hydroxy-2-(2-methyl-6-(1H-tetrazol-1-yl)pyridin-3-yl)ethyl)pyrrolidin-3-yl)-3-(4-methyl-5-oxo-2,5-dihydrofuran-3-yl)imidazolidin-2-one; single diastereomer, absolute stereochemistry not established, but opposite stereochemistry at hydroxyl substituted carbon compared to 13A |

-continued

| # | Intermediates | Structure | LC-MS (ESI, m/z): [M + 1]+ or NMR IUPAC name |
|---|---|---|---|
| 14 | 3B, 41 | | 442 | 1-(1-((R)-2-hydroxy-2-(4-methyl-1-oxo-1,3-dihydroisobenzofuran-5-yl)ethyl)pyrrolidin-3-yl)-3-(4-methyl-5-oxo-2,5-dihydrofuran-3-yl)imidazolidin-2-one (mixture of two diastereomer) |
| 15 | 3B, 37 | | 470 | (R)-1-(1-(2-hydroxy-2-(4-methyl-1-oxo-1,3-dihydroisobenzofuran-5-yl)ethyl)piperidin-4-yl)-3-(4-methyl-5-oxo-2,5-dihydrofuran-3-yl)tetrahydropyrimidin-2(1H)-one |
| 16 | 8A, 37 | | 483 | 1-(1-(2-hydroxy-2-(2-methyl-6-(1H-tetrazol-1-yl)pyridin-3-yl)ethyl)piperidin-4-yl)-3-(4-methyl-5-oxo-2,5-dihydrofuran-3-yl)tetrahydropyrimidin-2(1H)-one; single enantiomer |
| 17 | 8A, 25 (trans) | | 487 | 1-(3-fluoro-1-(2-hydroxy-2-(2-methyl-6-(1H-tetrazol-1-yl)pyridin-3-yl)ethyl)piperidin-4-yl)-3-(4-methyl-5-oxo-2,5-dihydrofuran-3-yl)imidazolidin-2-one; mixture of two trans piperidine diastereomers, absolute stereochemistry at the hydroxy substituted carbon was not established |
| 18A | 3B, 45 (trans) | | 474 | 1-(3-fluoro-1-((R)-2-hydroxy-2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one; single trans diastereomer |

Faster eluting isomer from SFC (chiralcel OD column)

| # | Intermediates | Structure | LC-MS (ESI, m/z): [M + 1]+ or NMR | IUPAC name |
|---|---|---|---|---|
| 18B | 3B, 46 (trans) | 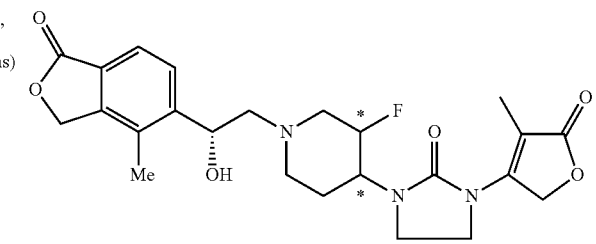 Slower eluting isomer from SFC (chiralcel OD column) | 474 | 1-(3-fluoro-1-((R)-2-hydroxy-2-(4-methyl-1-oxo-1,3-dihydrobenzofuran-5-yl)ethyl)piperidin-4-yl)-3-(4-methyl-5-oxo-2,5-dihydrofuran-3-yl)imidazolidin-2-one; single trans diastereomer with opposite absolute stereochemistry at piperidine compared to 18A |
| 18C | 3B, 46 (cis) | 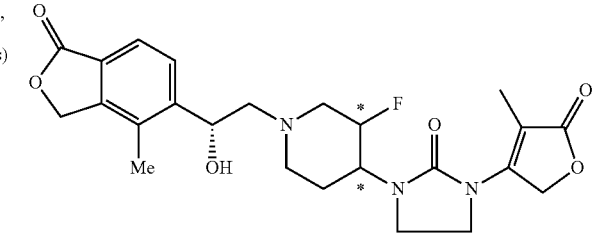 Faster eluting isomer from SFC (chiralcel OJ column) | 474 | 1-(3-fluoro-1-((R)-2-hydroxy-2-(4-methyl-1-oxo-1,3-dihydrobenzofuran-5-yl)ethyl)piperidin-4-yl)-3-(4-methyl-5-oxo-2,5-dihydrofuran-3-yl)imidazolidin-2-one; single cis diastereomer |
| 18D | 3B, 46 (cis) | 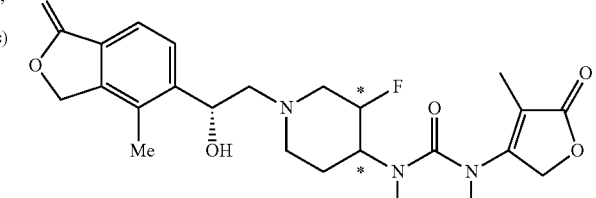 Slower eluting isomer from SFC (chiralcel OJ column) | 474 | 1-(3-fluoro-1-((R)-2-hydroxy-2-(4-methyl-1-oxo-1,3-dihydrobenzofuran-5-yl)ethyl)piperidin-4-yl)-3-(4-methyl-5-oxo-2,5-dihydrofuran-3-yl)imidazolidin-2-one; single cis diastereomer with opposite absolute stereochemistry at piperidine compared to 18C |
| 19A | 3B, 48 (cis) | 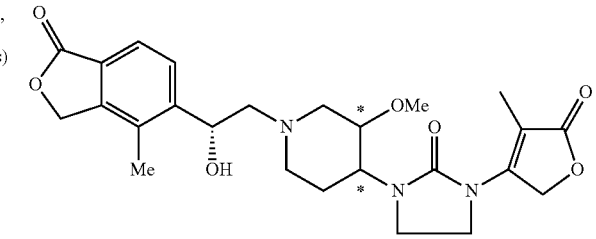 Faster eluting isomer from SFC (AS column) | 486 | 1-(1-((R)-2-hydroxy-2-(4-methyl-1-oxo-1,3-dihydroisobenzofuran-5-yl)ethyl)-3-methoxypiperidin-4-yl)-3-(4-methyl-5-oxo-2,5-dihydrofuran-3-yl)imidazolidin-2-one; single cis diastereomer |
| 19B | 3B, 48 (cis) | 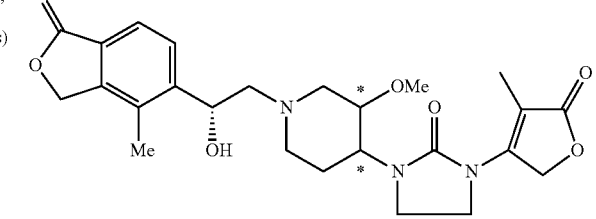 Slower eluting isomer from SFC (AS column) | 486 | 1-(1-((R)-2-hydroxy-2-(4-methyl-1-oxo-1,3-dihydroisobenzofuran-5-yl)ethyl)-3-methoxypiperidin-4-yl)-3-(4-methyl-5-oxo-2,5-dihydrofuran-3-yl)imidazolidin-2-one; single cis diastereomer with opposite absolute stereochemistry at piperidine compared to 19A |

| # | Intermediates | Structure | LC-MS (ESI, m/z): [M + 1]+ or NMR | IUPAC name |
|---|---|---|---|---|
| 20A | 6A, 48 (cis) | Faster eluting isomer from SFC (chiralpak AS column) | 486 | 1-(1-(2-(5-(1H-tetrazol-1-yl)pyrazin-2-yl)-2-hydroxyethyl)-3-methoxypiperidin-4-yl)-3-(4-methyl-5-oxo-2,5-dihydrofuran-3-yl)imidazolidin-2-one; single cis diastereomer |
| 20B | 6A, 48 (cis) | Slower eluting isomer from SFC (chiralpak AS column) | 486 | 1-(1-(2-(5-(1H-tetrazol-1-yl)pyrazin-2-yl)-2-hydroxyethyl)-3-methoxypiperidin-4-yl)-3-(4-methyl-5-oxo-2,5-dihydrofuran-3-yl)imidazolidin-2-one; single cis diastereomer with opposite absolute stereochemistry at piperidine compared to 20A |
| 21A | 6A, 46 (cis) | Faster eluting isomer from SFC (chiralpak AS column) | 474 | 1-(1-(2-(5-(1H-tetrazol-1-yl)pyrazin-2-yl)-2-hydroxyethyl)-3-fluoropiperidin-4-yl)-3-(4-methyl-5-oxo-2,5-dihydrofuran-3-yl)imidazolidin-2-one; single cis diastereomer |
| 21B | 6A, 46 (cis) | Slower eluting isomer from SFC (chiralpak AS column) | 474 | 1-(1-(2-(5-(1H-tetrazol-1-yl)pyrazin-2-yl)-2-hydroxyethyl)-3-methoxypiperidin-4-yl)-3-(4-methyl-5-oxo-2,5-dihydrofuran-3-yl)imidazolidin-2-one; single cis diastereomer with opposite absolute stereochemistry at piperidine compared to 21A |
| 22A | 6B, 37 | 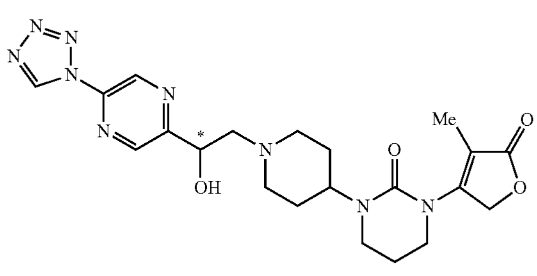 [SMILES: CC1=C(N2CCCN(C3CCN(CC(O)c4cnc(-n5cnnn5)cn4)CC3)C2=O)COC1=O] | 470 | 1-(1-(2-(5-(1H-tetrazol-1-yl)pyrazin-2-yl)-2-hydroxyethyl)piperidin-4-yl)-3-(4-methyl-5-oxo-2,5-dihydrofuran-3-yl)tetrahydropyrimidin-2(1H)-one; single enantiomer |

| # | Intermediates | Structure | LC-MS (ESI, m/z): [M + 1]+ or NMR IUPAC name |
|---|---|---|---|
| 22B | 6A, 37 | 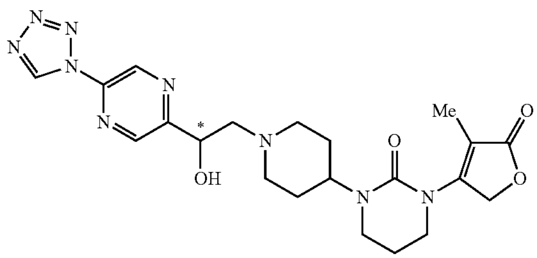 [SMILES: CC1=C(N2CCCN(C3CCN(CC(O)c4cnc(-n5cnnn5)cn4)CC3)C2=O)COC1=O] | 470 1-(1-(2-(5-(1H-tetrazol-1-yl)pyrazin-2-yl)-2-hydroxyethyl)piperidin-4-yl)-3-(4-methyl-5-oxo-2,5-dihydrofuran-3-yl)tetrahydropyrimidin-2(1H)-one; single enantiomer with opposite stereochemistry to 22A |
| 23A | 9A, 36 | 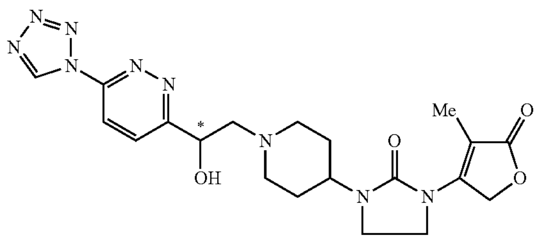 [SMILES: CC1=C(N2CCN(C3CCN(CC(O)c4ccc(-n5cnnn5)nn4)CC3)C2=O)COC1=O] | 456 1-(1-(2-(6-(1H-tetrazol-1-yl)pyridazin-3-yl)-2-hydroxyethyl)piperidin-4-yl)-3-(4-methyl-5-oxo-2,5-dihydrofuran-3-yl)imidazolidin-2-one, single enantiomer (absolute stereochemistry not established) |
| 23B | 9B, 36 | 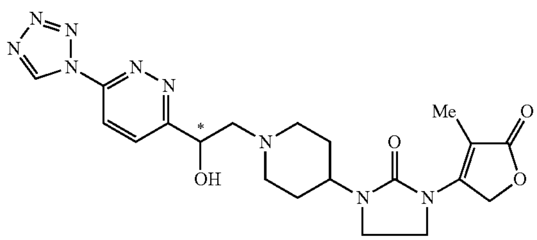 [SMILES: CC1=C(N2CCN(C3CCN(CC(O)c4ccc(-n5cnnn5)nn4)CC3)C2=O)COC1=O] | 456 1-(1-(2-(6-(1H-tetrazol-1-yl)pyridazin-3-yl)-2-hydroxyethyl)piperidin-4-yl)-3-(4-methyl-5-oxo-2,5-dihydrofuran-3-yl)imidazolidin-2-one, single enantiomer, opposite stereochemistry to 23A |
| 24A | 6A, 36 | 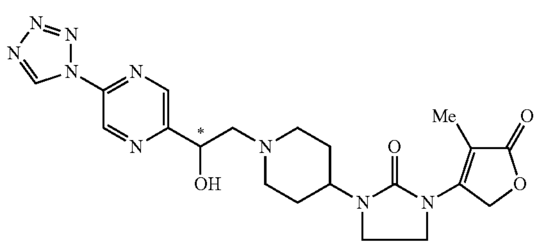 [SMILES: CC1=C(N2CCN(C3CCN(CC(O)c4cnc(-n5cnnn5)cn4)CC3)C2=O)COC1=O] | 456 1-(1-(2-(5-(1H-tetrazol-1-yl)pyrazin-3-yl)-2-hydroxyethyl)piperidin-4-yl)-3-(4-methyl-5-oxo-2,5-dihydrofuran-3-yl)imidazolidin-2-one, single enantiomer (absolute stereochemistry not established) |
| 24B | 6B, 36 | 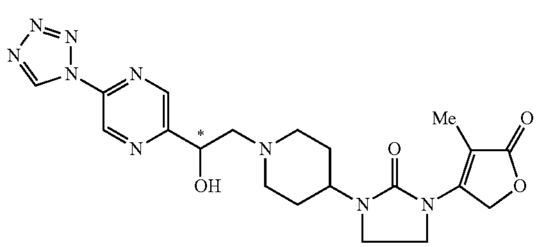 [SMILES: CC1=C(N2CCN(C3CCN(CC(O)c4cnc(-n5cnnn5)cn4)CC3)C2=O)COC1=O] | 456 1-(1-(2-(5-(1H-tetrazol-1-yl)pyrazin-3-yl)-2-hydroxyethyl)piperidin-4-yl)-3-(4-methyl-5-oxo-2,5-dihydrofuran-3-yl)imidazolidin-2-one, single enantiomer, opposite stereochemistry to 24A |

-continued

| # | Intermediates | Structure | LC-MS (ESI, m/z): [M + 1]+ or NMR | IUPAC name |
|---|---|---|---|---|
| 25A | 3B, 54 | Faster eluting peak from SFC purification using OJ column | 456 | 3-(4-((R)-2-hydroxy-2-(4-methyl-1-oxo-1,3-dihydroisobenzofuran-5-yl)piperazin-1-yl)-1-(4-methyl-5-oxo-2,5-dihydrofuran-3-yl)pyrrolidin-2-one, single enantiomer (absolute stereochemistry not established) |
| 25B | 3B, 54 | Slower eluting peak from SFC purification using OJ column | 456 | 3-(4-((R)-2-hydroxy-2-(4-methyl-1-oxo-1,3-dihydroisobenzofuran-5-yl)piperazin-1-yl)-1-(4-methyl-5-oxo-2,5-dihydrofuran-3-yl)pyrrolidin-2-one, single enantiomer, opposite stereochemistry to 25A |
| 26A | 7A, 54 | Faster eluting peak from SFC purification using AS column | 469 | 3-(4-(2-hydroxy-2-(2-methyl-6-(1H-tetrazol-1-yl)pyridin-3-yl)ethyl)piperazin-1-yl)-1-(4-methyl-5-oxo-2,5-dihydrofuran-3-yl)pyrrolidin-2-one, single enantiomer (absolute stereochemistry not established) |
| 26B | 8B, 54 | Slower eluting peak from SFC purification using AS column | 469 | 3-(4-(2-hydroxy-2-(2-methyl-6-(1H-tetrazol-1-yl)pyridin-3-yl)ethyl)piperazin-1-yl)-1-(4-methyl-5-oxo-2,5-dihydrofuran-3-yl)pyrrolidin-2-one, single enantiomer, opposite stereochemistry at pyrrolidinone stereocenter to 26A |
| 27A | 5A, 37 | 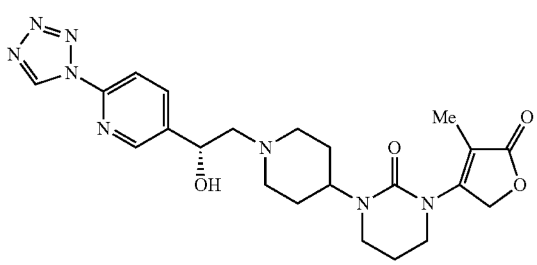 [SMILES: CC1=C(N2CCCN(C3CCN(C[C@H](O)c4ccc(-n5cnnn5)nc4)CC3)C2=O)COC1=O] | 469 | (R)-1-(1-(2-(6-(1H-tetrazol-1-yl)pyridin-3-yl)-2-hydroxyethyl)piperidin-4-yl)-3-(4-methyl-5-oxo-2,5-dihydrofuran-3-yl)tetrahydropyrimidin-2(1H)-one |

| # | Intermediates | Structure | LC-MS (ESI, m/z): [M + 1]+ or NMR IUPAC name |
|---|---|---|---|
| 27B | 5B, 37 | 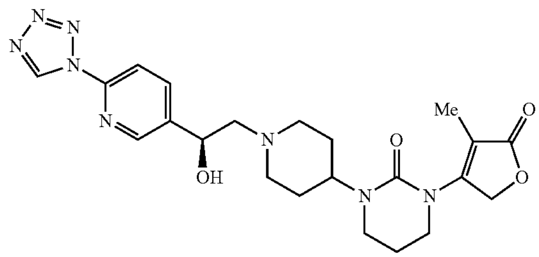 [SMILES: CC1=C(N2CCCN(C3CCN(C[C@@H](O)c4ccc(-n5cnnn5)nc4)CC3)C2=O)COC1=O] | 469 (S)-1-(1-(2-(6-(1H-tetrazol-1-yl)pyridin-3-yl)-2-hydroxyethyl)piperidin-4-yl)-3-(4-methyl-5-oxo-2,5-dihydrofuran-3-yl)tetrahydropyrimidin-2(1H)-one |
| 28 | 7A, 49A | 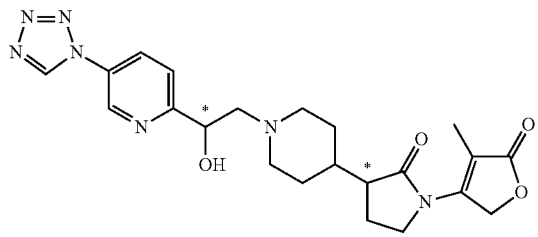 [SMILES: CC1=C(N2CCC(C3CCN(CC(O)c4ccc(-n5cnnn5)cn4)CC3)C2=O)COC1=O] | 454 3-(1-(2-(5-(1H-tetrazol-1-yl)pyridin-2-yl)-2-hydroxyethyl)piperidin-4-yl)-1-(4-methyl-5-oxo-2,5-dihydrofuran-3-yl)pyrrolidin-2-one, single isomer (absolute stereochemistry not established) |
| 29A | 3B, 42A | 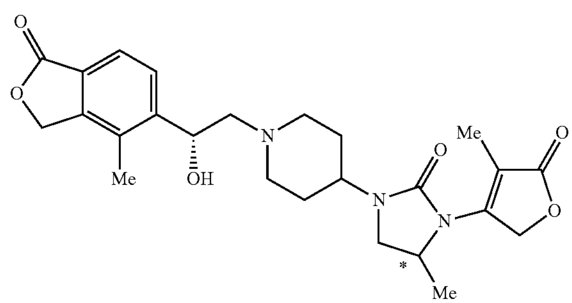 [SMILES: CC1=C(N2C(=O)N(C3CCN(C[C@H](O)c4ccc5c(c4C)COC5=O)CC3)CC2C)COC1=O] | 470 1-(1-((R)-2-hydroxy-2-(4-methyl-1-oxo-1,3-dihydroisobenzofuran-5-yl)ethyl)piperidin-4-yl)-4-methyl-3-(4-methyl-5-oxo-2,5-dihydrofuran-3-yl)imidazolidin-2-one, single isomer, absolute stereochemistry not established but opposite to 29B at cyclic urea stereocenter |
| 29B | 3B, 42B | 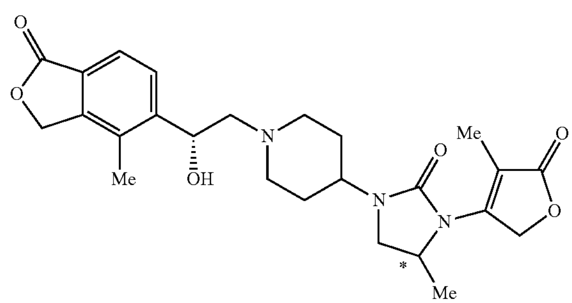 [SMILES: CC1=C(N2C(=O)N(C3CCN(C[C@H](O)c4ccc5c(c4C)COC5=O)CC3)CC2C)COC1=O] | 470 1-(1-((R)-2-hydroxy-2-(4-methyl-1-oxo-1,3-dihydroisobenzofuran-5-yl)ethyl)piperidin-4-yl)-4-methyl-3-(4-methyl-5-oxo-2,5-dihydrofuran-3-yl)imidazolidin-2-one, single isomer, absolute stereochemistry not established but opposite to 29A at cyclic urea stereocenter |
| 30A | 5A, 42A | 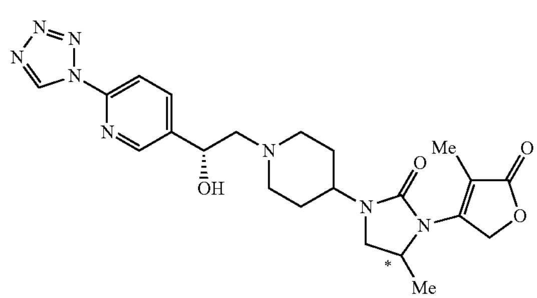 [SMILES: CC1=C(N2C(=O)N(C3CCN(C[C@H](O)c4ccc(-n5cnnn5)nc4)CC3)CC2C)COC1=O] | 469 1-(1-((R)-2-(6-(1H-tetrazol-1-yl)pyridin-3-yl)-2-hydroxyethyl)piperidin-4-yl)-4-methyl-3-(4-methyl-5-oxo-2,5-dihydrofuran-3-yl)imidazolidin-2-one, single isomer, absolute stereochemistry opposite to 30B at cyclic urea stereocenter |

-continued

| # | Intermediates | Structure | LC-MS (ESI, m/z): [M + 1]+ or NMR IUPAC name |
|---|---|---|---|
| 30B | 5A, 42B | 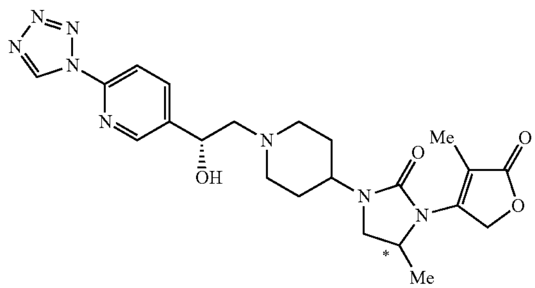 [SMILES: CC1=C(N2C(=O)N(C3CCN(C[C@H](O)c4ccc(-n5cnnn5)nc4)CC3)CC2C)COC1=O] | 469 1-(1-((R)-2-(6-(1H-tetrazol-1-yl)pyridin-3-yl)-2-hydroxyethyl)piperidin-4-yl)-4-methyl-3-(4-methyl-5-oxo-2,5-dihydrofuran-3-yl)imidazolidin-2-one, single isomer, absolute stereochemistry opposite to 30A at cyclic urea stereocenter |
| 30C | 5B, 42A | 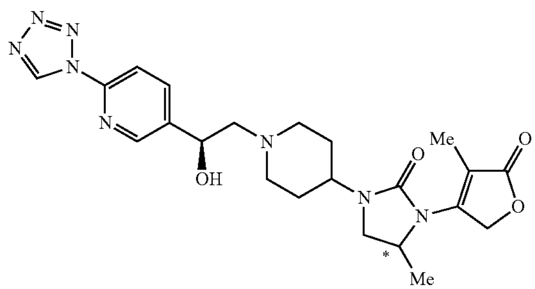 [SMILES: CC1=C(N2C(=O)N(C3CCN(C[C@@H](O)c4ccc(-n5cnnn5)nc4)CC3)CC2C)COC1=O] | 469 1-(1-((S)-2-(6-(1H-tetrazol-1-yl)pyridin-3-yl)-2-hydroxyethyl)piperidin-4-yl)-4-methyl-3-(4-methyl-5-oxo-2,5-dihydrofuran-3-yl)imidazolidin-2-one, single isomer, absolute stereochemistry opposite to 30D at cyclic urea stereocenter |
| 30D | 5B, 42B | 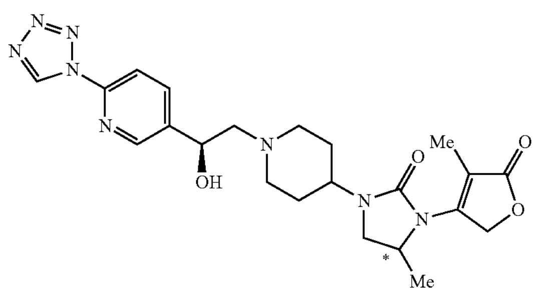 [SMILES: CC1=C(N2C(=O)N(C3CCN(C[C@@H](O)c4ccc(-n5cnnn5)nc4)CC3)CC2C)COC1=O] | 469 1-(1-((S)-2-(6-(1H-tetrazol-1-yl)pyridin-3-yl)-2-hydroxyethyl)piperidin-4-yl)-4-methyl-3-(4-methyl-5-oxo-2,5-dihydrofuran-3-yl)imidazolidin-2-one, single isomer, absolute stereochemistry opposite to 30C at cyclic urea stereocenter |
| 31 | 5A, 52A | 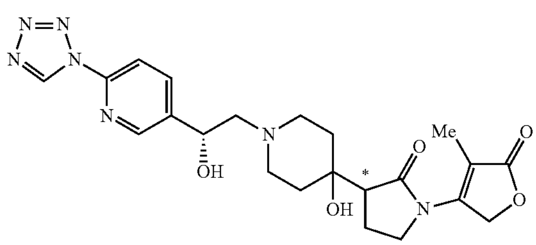 [SMILES: CC1=C(N2CCC(C3(O)CCN(C[C@H](O)c4ccc(-n5cnnn5)nc4)CC3)C2=O)COC1=O] | 470 3-(1-((R)-2-(6-(1H-tetrazol-1-yl)pyridin-3-yl)-2-hydroxyethyl)-4-hydroxypiperidin-4-yl)-1-(4-methyl-5-oxo-2,5-dihydrofuran-3-yl)pyrrolidin-2-one, single isomer, unknown absolute stereochemistry at lactam stereocenter |
| 32A | 3B, 44A | 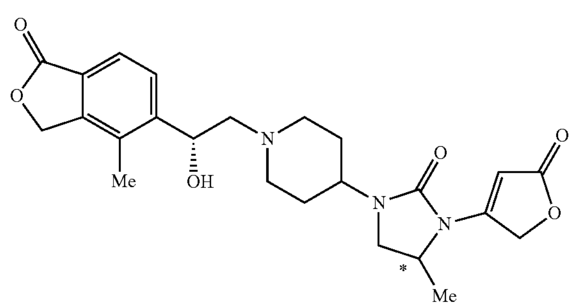 [SMILES: Cc1c([C@@H](O)CN2CCC(N3CC(C)N(C4=CC(=O)OC4)C3=O)CC2)ccc2c1COC2=O] | 456 1-(1-((R)-2-hydroxy-2-(4-methyl-1-oxo-1,3-dihydroisobenzofuran-5-yl)ethyl)piperidin-4-yl)-4-methyl-3-(5-oxo-2,5-dihydrofuran-3-yl)imidazolidin-2-one, single isomer, absolute stereochemistry not established but opposite to 32B at cyclic urea stereocenter |

-continued

| # | Intermediates | Structure | LC-MS (ESI, m/z): [M + 1]+ or NMR IUPAC name |
|---|---|---|---|
| 32B | 3B, 44B | 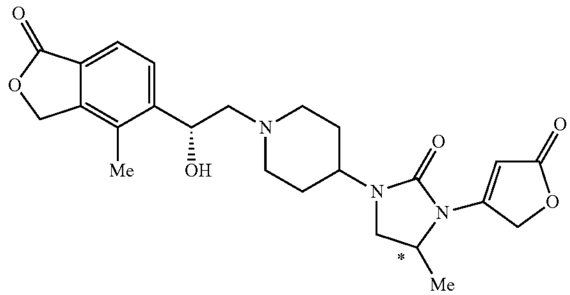 [SMILES: Cc1c([C@@H](O)CN2CCC(N3CC(C)N(C4=CC(=O)OC4)C3=O)CC2)ccc2c1COC2=O] | 456  1-(1-((R)-2-hydroxy-2-(4-methyl-1-oxo-1,3-dihydroisobenzofuran-5-yl)ethyl)piperidin-4-yl)-4-methyl-3-(5-oxo-2,5-dihydrofuran-3-yl(imidazolidin-2-one, single isomer, absolute stereochemistry not established but opposite to 32A at cyclic urea stereocenter |
| 33A | 5A, 44A | 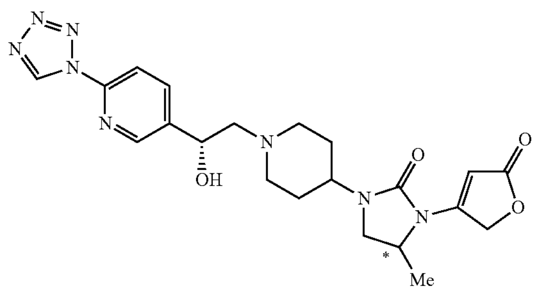 [SMILES: CC1CN(C2CCN(C[C@H](O)c3ccc(-n4cnnn4)nc3)CC2)C(=O)N1C1=CC(=O)OC1] | 455  1-(1-((R)-2-(6-(1H-tetrazol-1-yl)pyridin-3-yl)-2-hydroxyethyl)piperidin-4-yl)-4-methyl-3-(5-oxo-2,5-dihydrofuran-3-yl)imidazolidin-2-one, single isomer, absolute stereochemistry opposite to 33B at cyclic urea stereocenter |
| 33B | 5A, 44B | 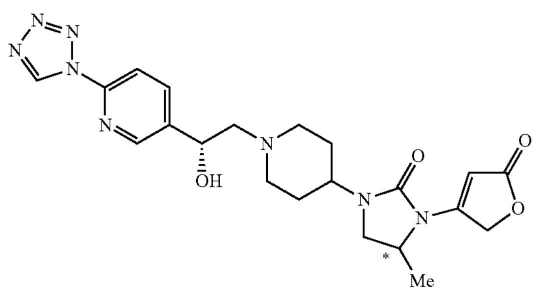 [SMILES: CC1CN(C2CCN(C[C@H](O)c3ccc(-n4cnnn4)nc3)CC2)C(=O)N1C1=CC(=O)OC1] | 455  1-(1-((R)-2-(6-(1H-tetrazol-1-yl)pyridin-3-yl)-2-hydroxyethyl)piperidin-4-yl)-4-methyl-3-(5-oxo-2,5-dihydrofuran-3-yl)imidazolidin-2-one, single isomer, absolute stereochemistry opposite to 33A at cyclic urea stereocenter |
| 33C | 5B, 44A | 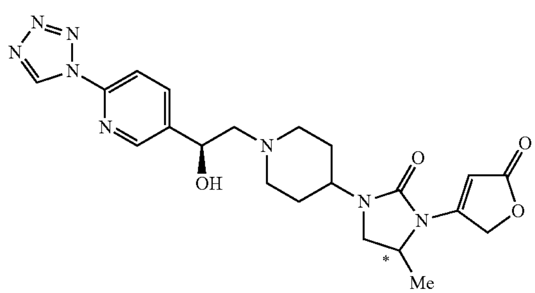 [SMILES: CC1CN(C2CCN(C[C@@H](O)c3ccc(-n4cnnn4)nc3)CC2)C(=O)N1C1=CC(=O)OC1] | 455  1-(1-((S)-2-(6-(1H-tetrazol-1-yl)pyridin-3-yl)-2-hydroxyethyl)piperidin-4-yl)-4-methyl-3-(5-oxo-2,5-dihydrofuran-3-yl)imidazolidin-2-one, single isomer, absolute stereochemistry opposite to 33D at cyclic urea stereocenter |
| 33D | 5B, 44B | 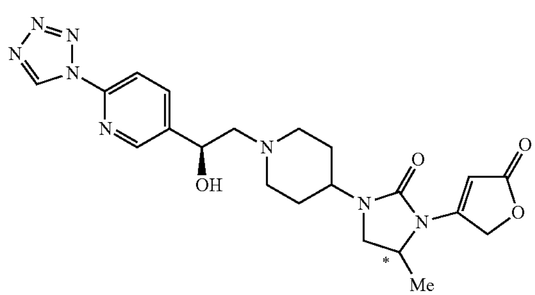 [SMILES: CC1CN(C2CCN(C[C@@H](O)c3ccc(-n4cnnn4)nc3)CC2)C(=O)N1C1=CC(=O)OC1] | 455  1-(1-((S)-2-(6-(1H-tetrazol-1-yl)pyridin-3-yl)-2-hydroxyethyl)piperidin-4-yl)-4-methyl-3-(5-oxo-2,5-dihydrofuran-3-yl)imidazolidin-2-one, single isomer, absolute stereochemistry opposite to 33C at cyclic urea stereocenter |

-continued

| # | Intermediates | Structure | LC-MS (ESI, m/z): [M + 1]+ or NMR IUPAC name |
|---|---|---|---|
| 34 | 5A, 57 | 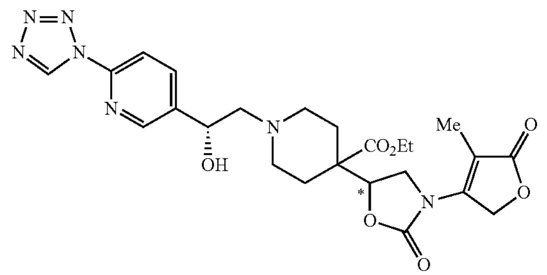 [SMILES: CCOC(=O)C1(C2CN(C3=C(C)C(=O)OC3)C(=O)O2)CCN(C[C@H](O)c2ccc(-n3cnnn3)nc2)CC1] | 528 ethyl 1-((R)-2-(6-(1H-tetrazol-1-yl)pyridin-3-yl)-2-hydroxyethyl)-4-(3-(4-methyl-5-oxo-2,5-dihydrofuran-3-yl)-2-oxooxazolidin-5-yl)piperidine-4-carboxylate, mixture of two diastereomers |
| 35 | 3B, 57 | 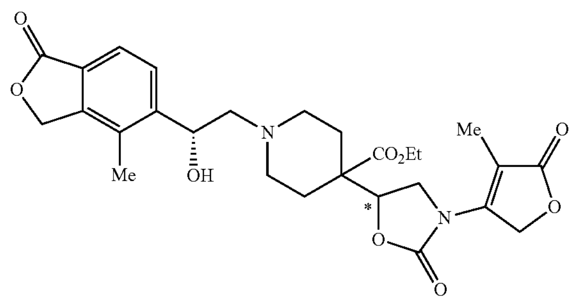 [SMILES: CCOC(=O)C1(C2CN(C3=C(C)C(=O)OC3)C(=O)O2)CCN(C[C@H](O)c2ccc3c(c2C)COC3=O)CC1] | 529 ethyl 1-((R)-2-hydroxy-2-(4-methyl-1-oxo-1,3-dihydroisobenzofuran-5-yl)ethyl)-4-(3-(4-methyl-5-oxo-2,5-dihydrofuran-3-yl)-2-oxooxazolidin-5-yl)piperidine-4-carboxylate, mixture of two diastereomers |
| 36A | 3B, 52A | 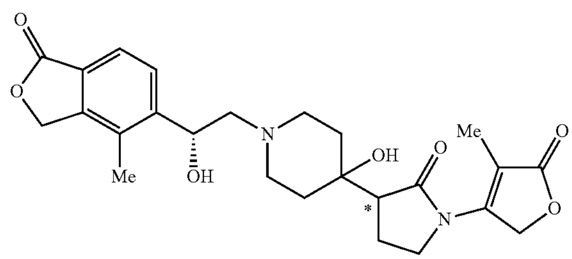 [SMILES: CC1=C(N2CCC(C3(O)CCN(C[C@H](O)c4ccc5c(c4C)COC5=O)CC3)C2=O)COC1=O] | 471 3-(4-hydroxy-1-((R)-2-hydroxy-2-(4-methyl-1-oxo-1,3-dihydroisobenzofuran-5-yl)ethyl)piperidin-4-yl)-1-(4-methyl-5-oxo-2,5-dihydrofuran-3-yl)pyrrolidin-2-one, single diastereomer, absolute stereochemistry not determined |
| 36B | 3B, 52B | 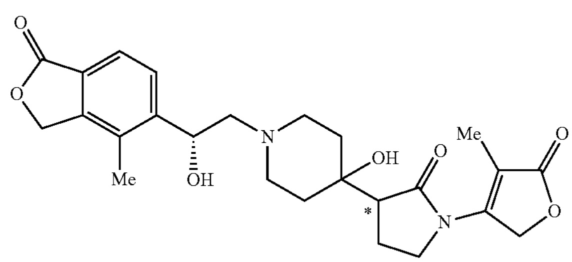 [SMILES: CC1=C(N2CCC(C3(O)CCN(C[C@H](O)c4ccc5c(c4C)COC5=O)CC3)C2=O)COC1=O] | 471 3-(4-hydroxy-1-((R)-2-hydroxy-2-(4-methyl-1-oxo-1,3-dihydroisobenzofuran-5-yl)ethyl)piperidin-4-yl)-1-(4-methyl-5-oxo-2,5-dihydrofuran-3-yl)pyrrolidin-2-one, single diastereomer, absolute stereochemistry not determined but opposite to 36A |
| 37A | 3B, 51A | 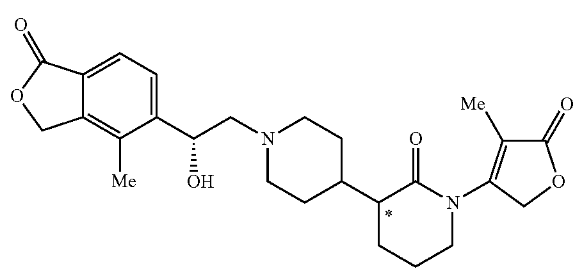 [SMILES: CC1=C(N2CCCC(C3CCN(C[C@H](O)c4ccc5c(c4C)COC5=O)CC3)C2=O)COC1=O] | 469 1'-((R)-2-hydroxy-2-(4-methyl-1-oxo-1,3-dihydroisobenzofuran-5-yl)ethyl)-1-(4-methyl-5-oxo-2,5-dihydrofuran-3-yl)-[3,4'-bipiperidin]-2-one, single diastereomer, absolute stereochemistry not determined |

| # | Intermediates | Structure | LC-MS (ESI, m/z): [M + 1]+ or NMR IUPAC name |
|---|---|---|---|
| 37B | 3B, 51B | 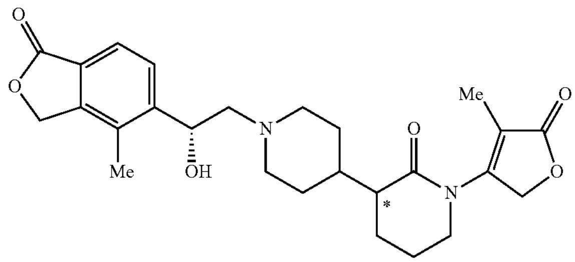 [SMILES: CC1=C(N2CCCC(C3CCN(C[C@H](O)c4ccc5c(c4C)COC5=O)CC3)C2=O)COC1=O] | 469 1'-((R)-2-hydroxy-2-(4-methyl-1-oxo-1,3-dihydroisobenzofuran-5-yl)ethyl)-1-(4-methyl-5-oxo-2,5-dihydrofuran-3-yl)-[3,4'-bipiperidin]-2-one, single diastereomer, absolute stereochemistry not determined but opposite to 37A |
| 38A | 3B, 53 | 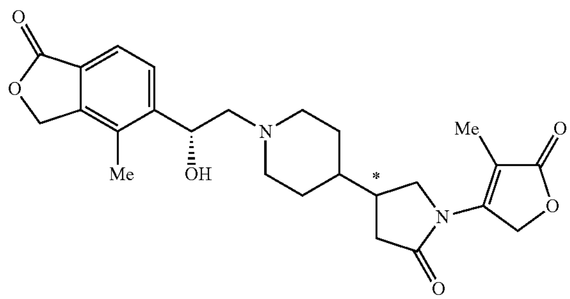 [SMILES: CC1=C(N2CC(C3CCN(C[C@H](O)c4ccc5c(c4C)COC5=O)CC3)CC2=O)COC1=O] | 455 4-(1-((R)-2-hydroxy-2-(4-methyl-1-oxo-1,3-dihydroisobenzofuran-5-yl)ethyl)piperidin-4-yl)-1-(4-methyl-5-oxo-2,5-dihydrofuran-3-yl)pyrrolidin-2-one, single diastereomer, absolute stereochemistry not determined |
| 38B | 3B, 53 | 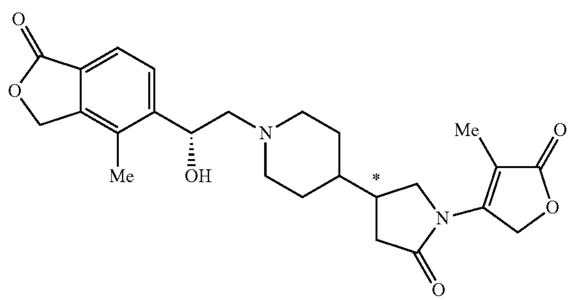 [SMILES: CC1=C(N2CC(C3CCN(C[C@H](O)c4ccc5c(c4C)COC5=O)CC3)CC2=O)COC1=O] | 455 4-(1-((R)-2-hydroxy-2-(4-methyl-1-oxo-1,3-dihydroisobenzofuran-5-yl)ethyl)piperidin-4-yl)-1-(4-methyl-5-oxo-2,5-dihydrofuran-3-yl)pyrrolidin-2-one, single diastereomer, absolute stereochemistry not determined but opposite to 38A |
| 39 | 3B, 50A | 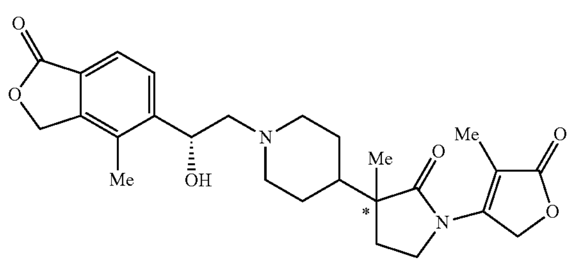 [SMILES: CC1=C(N2CCC(C)(C3CCN(C[C@H](O)c4ccc5c(c4C)COC5=O)CC3)C2=O)COC1=O] | 469 3-(1-((R)-2-hydroxy-2-(4-methyl-1-oxo-1,3-dihydroisobenzofuran-5-yl)ethyl)piperidin-4-yl)-3-methyl-1-(4-methyl-5-oxo-2,5-dihydrofuran-3-yl)pyrrolidin-2-one, single diastereomer, absolute stereochemistry not determined |
| 40 | 5A, 50A | 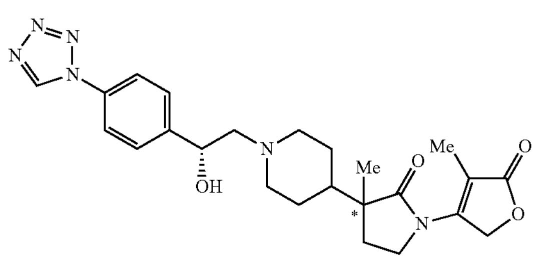 [SMILES: CC1=C(N2CCC(C)(C3CCN(C[C@H](O)c4ccc(-n5cnnn5)cc4)CC3)C2=O)COC1=O] | 468 3-(1-((R)-2-(6-(1H-tetrazol-1-yl)pyridin-3-yl)-2-hydroxyethyl)piperidin-4-yl)-3-methyl-1-(4-methyl-5-oxo-2,5-dihydrofuran-3-yl)pyrrolidin-2-one, single diastereomer, absolute stereochemistry not determined |

-continued

| # | Intermediates | Structure | LC-MS (ESI, m/z): [M + 1]+ or NMR IUPAC name |
|---|---|---|---|
| 41A | 5A, 43A | 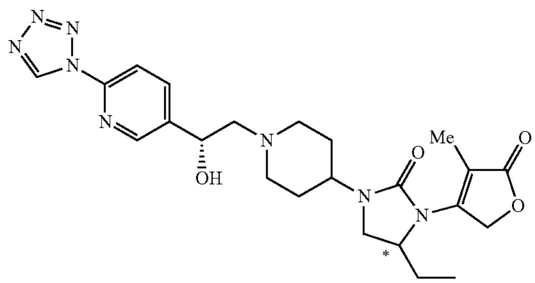 [SMILES: CCC1CN(C2CCN(C[C@H](O)c3ccc(-n4cnnn4)nc3)CC2)C(=O)N1C1=C(C)C(=O)OC1] | 483 1-(1-((R)-2-(6-(1H-tetrazol-1-yl)pyridin-3-yl)-2-hydroxyethyl)piperidin-4-yl)-4-ethyl-3-(4-methyl-5-oxo-2,5-dihydrofuran-3-yl)imidazolidin-2-one, single diastereomer, absolute stereochemistry not determined |
| 41B | 5A, 43B | 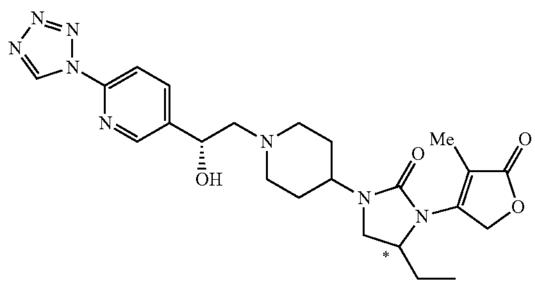 [SMILES: CCC1CN(C2CCN(C[C@H](O)c3ccc(-n4cnnn4)nc3)CC2)C(=O)N1C1=C(C)C(=O)OC1] | 483 1-(1-((R)-2-(6-(1H-tetrazol-1-yl)pyridin-3-yl)-2-hydroxyethyl)piperidin-4-yl)-4-ethyl-3-(4-methyl-5-oxo-2,5-dihydrofuran-3-yl)imidazolidin-2-one, single diastereomer, absolute stereochemistry not determined but opposite to 41A at cyclic urea stereomer |
| 42A | 3B, 43A | 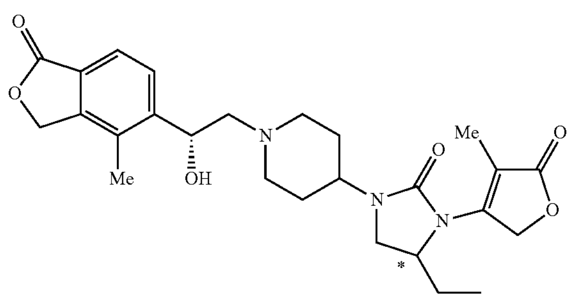 [SMILES: CCC1CN(C2CCN(C[C@H](O)c3ccc4c(c3C)COC4=O)CC2)C(=O)N1C1=C(C)C(=O)OC1] | 484 4-ethyl-1-(1-((R)-2-hydroxy-2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one, single diastereomer, absolute stereochemistry not determined |
| 42B | 3B, 43B | 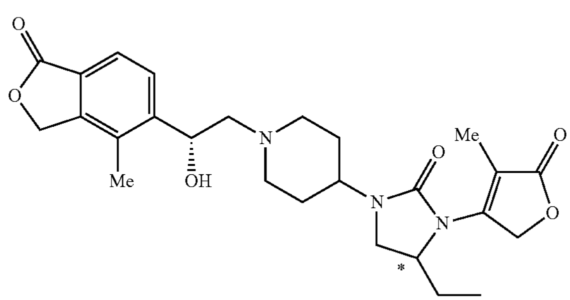 [SMILES: CCC1CN(C2CCN(C[C@H](O)c3ccc4c(c3C)COC4=O)CC2)C(=O)N1C1=C(C)C(=O)OC1] | 484 4-ethyl-1-(1-((R)-2-hydroxy-2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one, single diastereomer, absolute stereochemistry not determined but opposite to 42A at cyclic urea stereocenter |
| 43 | 3B, 43B | 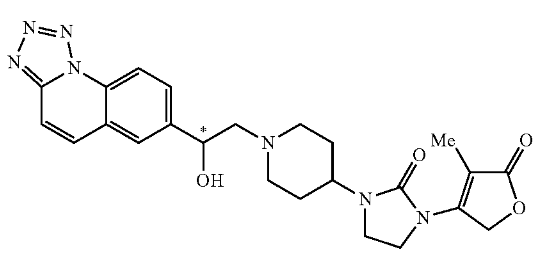 [SMILES: CC1=C(N2CCN(C3CCN(CC(O)c4ccc5c(ccc6nnnn65)c4)CC3)C2=O)COC1=O] | 478 1-(1-(2-hydroxy-2-(tetrazolo[1,5-a]quinolin-7-yl)ethyl)piperidin-4-yl)-3-(4-methyl-5-oxo-2,5-dihydrofuran-3-yl)imidazolidin-2-one, single enantiomer from chiral SFC separation, absolute stereochemistry not established |

Example 44

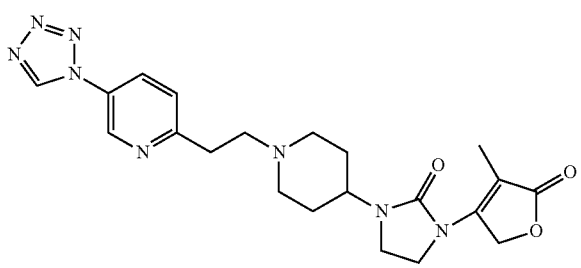 [SMILES: CC1=C(N2CCN(C3CCN(CCc4ccc(-n5cnnn5)cn4)CC3)C2=O)COC1=O]

1-(1-(2-(5-(1H-Tetrazol-1-yl)pyridin-2-yl)ethyl)piperidin-4-yl)-3-(4-methyl-5-oxo-2,5-dihydrofuran-3-yl)imidazolidin-2-one 1-(4-Methyl-5-oxo-2,5-dihydrofuran-3-yl)-3-(piperidin-4-yl)imidazolidin-2-one (Intermediate 36, 72 mg, 0.27 mmol), 5-(1H-tetrazol-1-yl)-2-vinylpyridine (Intermediate 13, 188 mg, 1.1 mmol), DPEphos (15 mg, 0.027 mmol) and Rh(COD)BF$_4$ (11 mg, 0.027 mmol) in toluene (1.5 mL) was stirred at 70° C. for 24 h under N$_2$. The mixture was concentrated and purified by preparative HPLC to afford the title compound. $^1$H-NMR (400 MHz, DMSO) δ ppm 10.42 (s, 1H), 10.12 (s, 1H), 9.06 (d, J=2.3 Hz, 1H), 8.30-8.38 (m, 1H), 7.65 (d, J=8.6 Hz, 1H), 5.10 (s, 2H), 4.13 (t, J=7.8 Hz, 2H), 3.10-3.65 (m, 10H), 2.00-2.18 (m, 2H), 1.80-1.90 (m, 5H). LC-MS (ESI, m/z): 439 [M+1]$^+$.

The following compounds were prepared in an analogous fashion to that described for 1-(1-(2-(5-(1H-Tetrazol-1-yl)pyridin-2-yl)ethyl)piperidin-4-yl)-3-(4-methyl-5-oxo-2,5-dihydrofuran-3-yl)imidazolidin-2-one (immediately above, Example 44) using styrenes and amities prepared as described previously.

Example 47

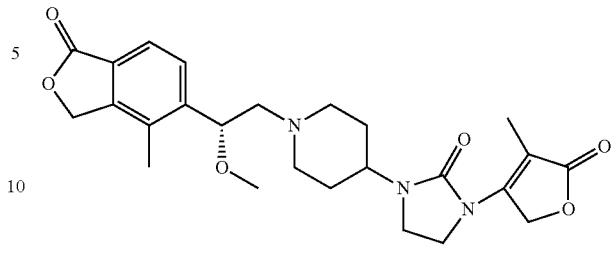

(R)-1-(1-(2-methoxy-2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one NaBH(OAc)$_3$ (633 mg, 3.00 mmol) was added to a solution of (R)-2-methoxy-2-(4-methyl-1-oxo-1,3-dihydroisobenzofuran-5-yl)acetaldehyde (222 mg, 1.00 mmol) and 1-(4-methyl-5-oxo-2,5-dihydrofuran-3-yl)-3-(piperidin-4-yl)imidazolidin-2-one (240 mg, 0.80 mmol) in DCM (5 mL) and AcOH (0.1 mL). The resulting mixture was stirred at room temperature for 0.5 h. The mixture was partitioned between water and DCM. The organic layer was separated and concentrated, the residue was purified by column chromatography eluted with EtOAc:MEOH=5:1 to afford the title compound. $^1$H-NMR (400 MHz, MeOD) δ ppm 7.75 (m, 1H), 7.64 (m, 1H), 5.38 (s, 2H), 5.21 (s, 2H), 4.22 (m, 2H), 3.63 (m, 1H), 3.59 (m, 1H), 3.32 (s, 3H), 3.31 (m, 2H), 2.78 (m, 1H), 2.46 (m, 1H), 2.37 (s, 3H), 2.33 (m, 1H), 1.98 (s, 3H), 1.88 (m, 2H), 1.74 (m, 2H); LC-MS (ESI, m/z): 470 [M+1]$^+$.

The following compounds were prepared in an analagous fashion to that described for (R)-1-(1-(2-methoxy-2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one (Example 47) using aldehydes and amines prepared as described previously.

| Ex. | Intermediates | Example structure | LC/MS [M + 1]$^+$ | Example Name |
|---|---|---|---|---|
| 45 | 11, 36 | | 440 | 1-(1-(2-(6-(1H-tetrazol-1-yl)pyridazin-3-yl)ethyl)piperidin-4-yl)-3-(4-methyl-5-oxo-2,5-dihydrofuran-3-yl)imidazolidin-2-one |
| 46 | 10, 36 | | 440 | 1-(1-(2-(5-(1H-tetrazol-1-yl)pyrazin-2-yl)ethyl)piperidin-4-yl)-3-(4-methyl-5-oxo-2,5-dihydrofuran-3-yl)imidazolidin-2-one |

| Ex. | Intermediates | Example structure | LC/MS [M + 1]+ | Example IUPAC Name |
|---|---|---|---|---|
| 48 | 17, 36 | | 484 | (R)-1-(1-(2-ethoxy-2-(4-methyl-1-oxo-1,3-dihydrobenzofuran-5-yl)ethyl)piperidin-4-yl)-3-(4-methyl-5-oxo-2,5-dihydrofuran-3-yl)imidazolidin-2-one |
| 49 | 18, 36 | | 469 | (R)-1-(1-(2-(6-(1H-tetrazol-1-yl)pyridin-3-yl)-2-methoxyethyl)piperidin-4-yl)-3-(4-methyl-5-oxo-2,5-dihydrofuran-3-yl)imidazolidin-2-one |
| 50 | 15, 36 | | 439 | 1-(1-(2-(6-(1H-Tetrazol-1-yl)pyridin-3-yl)ethyl)piperidin-4-yl)-3-(4-methyl-5-oxo-2,5-dihydrofuran-3-yl)imidazolidin-2-one |
| 51 | 2, 36 | | 440 | 1-(1-(2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one |

Examples 52A, 52B, 52C, 52D (Four Individual Diastereomers)

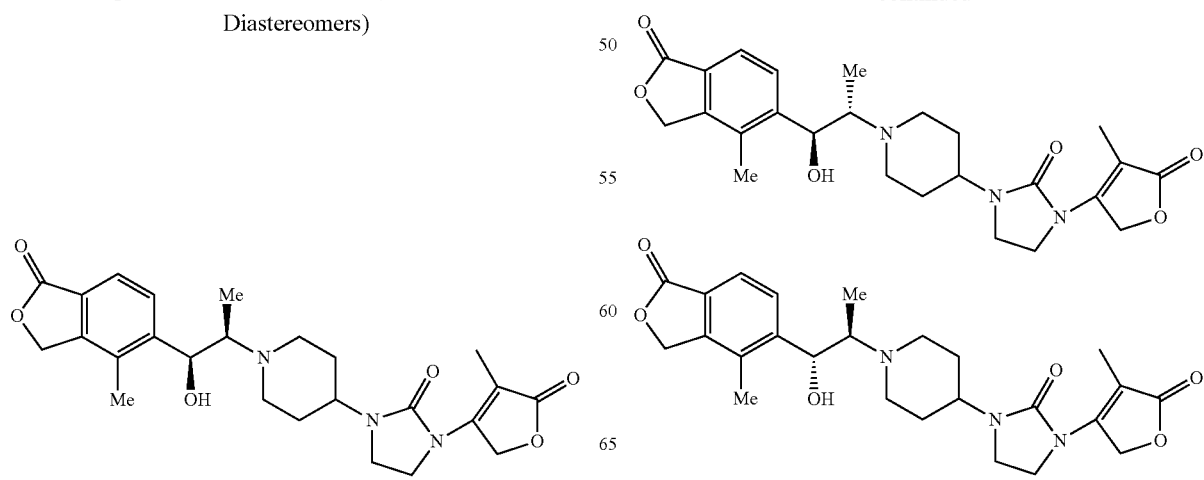

-continued

-continued

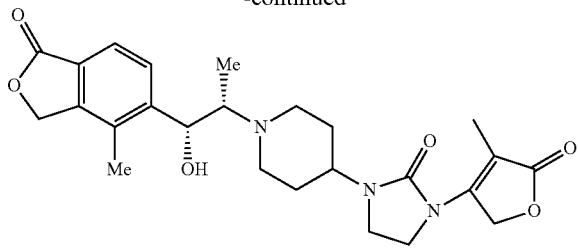

1-(1-(1-hydroxy-1-(4-methyl-1-oxo-1,3-dihydroisobenzofuran-5-yl)propan-2-yl)piperidin-4-yl)-3-(4-methyl-5-oxo-2,5-dihydrofuran-3-yl)imidazolidin-2-one (individual isomers are: 1-(1-((1R,2R)-1-hydroxy-1-methyl-1-oxo-1,3-dihydroisobenzofuran-5-yl)propan-2-yl)piperidin-4-yl)-3-(4-methyl-5-oxo-2,5-dihydrofuran-3-yl)imidazolidin-2-one; 1-(1-((1R,2S)-1-hydroxy-1-(4-methyl-1-oxo-1,3-dihydroisobenzofuran-5-yl)propan-2-yl)piperidin-4-yl)-3-(4-methyl-5-oxo-2,5-dihydrofuran-3-yl)imidazolidin-2-one; 1-(1-((1S,2R)-1-hydroxy-1-(4-methyl-1-oxo-1,3-dihydroisobenzofuran-5-yl)propan-2-yl)piperidin-4-yl)-3-(4-methyl-5-oxo-2,5-dihydrofuran-3-yl)imidazolidin-2-one; 1-(1-((1S,2S)-1-hydroxy-1-(4-methyl-1-oxo-1,3-dihydroisobenzofuran-5-yl)propan-2-yl) piperidin-4-yl)-3-(4-methyl-5-oxo-2,5-dihydrofuran-3-yl) imidazolidin-2-one)

Step A: 4-methyl-5-(prop-1-en-1-yl)isobenzofuran-1(3H)-one

To a solution of 4-methyl-1-oxo-1,3-dihydroisobenzofuran-5-yl trifluoromethanesulfonate (1.50 g, 5.1 mmol) in 30 mL of THF was added (E)-prop-1-en-1-ylboronic acid (700 mg, 1.6 mmol) and Pd-118 (326 mg, 0.5 mmol) under $N_2$ atmosphere, followed by $K_3PO_4$ (2.15 g, 10 mmol, 1 M in $H_2O$). The resulting mixture was stirred at 75° C. overnight under $N_2$, cooled and concentrated, the residue was diluted with ethyl acetate and $H_2O$, filtered, aqueous layer was extracted with EtOAc, the combined organic layers were washed with brine, dried over anhydrous $Na_2SO_4$, filtered and concentrated, the residue was purified by flash chromatography (0-20% EtOAc in petroleum ether) to afford the title compound. $^1$H-NMR (400 MHz, CDCl$_3$) δ ppm 7.67 (d, J=8.0 Hz, 1H), 7.56 (d, J=8.0 Hz, 1H), 663 (dd, J=13 Hz, 1.2 Hz, 1H), 6.34-6.26 (m, 1H), 5.23 (s, 2H), 2.27 (s, 3H), 1.95 (dd, J=6.8 Hz, 1.6 Hz, 3H).

Step B: 5-(1,2-dihydroxypropyl)-4-methylisobenzofuran-1(3H)-one

To a solution of 4-methyl-5-(prop-1-en-1-yl)isobenzofuran-1(3H)-one (930 mg, 4.9 mmol) in 40 mL of $CH_3CN$ and 4 mL of water was added NMO (746 mg, 5.4 mmol), followed by $K_2OsO_5 \cdot 2H_2O$ (91 mg, 0.25 mmol) at 0° C., the resulting mixture was warmed to room temperature and stirred for 2 hrs under $N_2$ atmosphere. The resulting mixture was diluted with DCM and washed with $Na_2S_2O_3$ solution (25% aq) and water, the organic layer was dried over anhydrous $Na_2SO_4$, filtered and concentrated, the residue was purified by flash chromatography (0 to 65% EtOAc in petroleum ether) to afford the title compound. $^1$H-NMR (400 MHz, CDCl$_3$) δ ppm 7.77 (d, J=8.0 Hz, 1H), 7.64 (d, J=8.0 Hz, 1H), 5.25 (s, 2H), 4.82 (dd, J=7.2 Hz, 3.6 Hz, 1H), 3.98-3.90 (m, 1H), 2.78 (d, J=3.2 Hz, 1H), 2.39 (d, J=4.0 Hz, 1H), 2.34 (s, 3H), 1.12 (d, J=6.4 Hz, 3H).

Step C: 1-(1-(1-hydroxy-1-(4-methyl-1-oxo-1,3-dihydroisobenzofuran-5-yl)propan-2-yl)piperidin-4-yl)-3-(4-methyl-5-oxo-2,5-dihydrofuran-3-yl)imidazolidin-2-one To a MW vial was charged with 5-(1,2-dihydroxypropyl)-4-methylisobenzofuran-1(3H)-one (170 mg, 0.76 mmol), 1-(4-methyl-5-oxo-2,5-dihydrofuran-3-yl)-3-(piperidin-4-yl)imidazolidin-2-one (243 mg, 0.92 mmol), $Ru_3(CO)_{12}$ (147 mg, 0.23 mmol), 2-(dicyclohexylphosphino)-1-phenyl-1H-pyrrole (156 mg, 0.46 mmol) and 1.7 mL of tert-amyl alcohol, the MW vial was degassed, sealed, and heated at 145° C. over weekend, then filtered and washed with DCM, concentrated, the residue was purified by flash chromatography (from 0 to 15 of MeOH in EtOAc) to afford the title compounds separated into syn products as a pair of enantiomers and anti products as a pair of enantiomers); the syn and anti enantiomer pairs were individually separated by chiral SFC [eluting with 40% MeOH (0.05% DEA)/CO$_2$ on Chiralpak AS-H column] to afford the four single diastereomer products.

52A: less polar on TLC fast eluting on SFC. $^1$H-NMR (400 MHz, CDCl$_3$) δ ppm 7.74 (d, J=8.0 Hz, 1H), 7.60 (d, J=8.4 Hz, 1H), 15.24 (s, 2H), 5.20 (s, 2H), 4.66 (d, J=9.6 Hz, 1H), 4.16 (t, J=8.0 Hz, 2H), 3.84-3.74 (m, 1H), 3.62-3.55 (m, 2H), 2.96 (d, J=12 Hz, 1H), 2.85-2.68 (m, 3H), 2.60-2.50 (br, 1H), 2.31 (s, 3H), 1.98 (s, 3H), 1.85-1.78 (m, 3H), 1.75-1.63 (m, 1H), 0.76 (d, J=6.4 Hz, 3H). LC-MS (ESI, m/z): 470 [M+1]$^+$.

52B: less polar on TLC, slow eluting on SFC. $^1$H-NMR (400 MHz, CDCl$_3$) δ ppm 7.75 (d, J=8.4 Hz, 1H), 7.62 (d, J=8.0 Hz, 1H), 5.25 (s, 2H), 5.21 (s, 2H), 4.70 (d, J=9.6 Hz, 1H), 4.17 (t, J=8.0 Hz, 2H), 3.88-3.77 (m, 1H), 3.60 (t, J=9.2 Hz, 2H), 3.06-3.00 (br, 1H), 2.90-2.73 (m, 3H), 2.44-2.35 (m, 1H), 2.32 (s, 3H), 2.01 (s, 3H), 1.83 (d, J=8.8 Hz, 3H), 1.23 (s, 1H), 0.79 (d, J=6.4 Hz, 3H). LC-MS (ESI, m/z): 470 [M+1]$^+$.

52C: more polar on TLC, fast eluting on SFC. $^1$H-NMR (400 MHz, CDCl$_3$) δ ppm 7.78 (s, 2H), 2.25-5.21 (m, 5H), 4.19 (t, J=8.0 Hz, 2H), 3.86-3.78 (m, 1H), 3.58 (t, J=8.0 Hz, 2H), 3.35 (d, J=12 Hz, 1H), 3.10 (d, J=11 Hz, 2.80-2.70 (m, 1H), 2.45-2.30 (m, 2H), 2.28 (s, 3H), 2.02 (s, 3H), 1.80-1.60 (m, 4H), 1.25 (s, 1H), 0.82 (d, J=6.4 Hz, 3H). LC-MS (ESI, m/z): 470 [M+1]$^+$.

52D: more polar on TLC, slow eluting on SFC. $^1$H-NMR (400 MHz, CDCl$_3$) δ ppm 7.80-7.70 (m, 2H), 5.23 (s, 2H), 5.17 (s, 2H), 4.14 (t, J=8.4 Hz, 2H), 3.95-3.85 (br, 1H), 3.70-3.58 (m, 2H), 2.33 (s, 3H), 1.97 (s, 3H), 1.90-1.80 (br, 2H), 1.75-1.38 (m, 4H), 1.30-1.18 (m, 5H), 1.15-1.00 (m, 3H). LC-MS (ESI, m/z): 470 [M+1]$^-$.

The Examples in the table below were prepared in an analogous fashion as that described for 3-(1-((R)-2-hydroxy-2-(4-methyl-1-oxo-1,3-dihydroisobenzofuran-5-yl) ethyl)piperidin-4-yl)-1-(4-methyl-5-oxo-2,5-dihydrofuran-3-yl)pyrrolidin-2-one (EXAMPLE 1) from the amine and epoxide Intermediates indicated, which were, in turn, prepared as described above.

| # | Intermediates | Structure | LC-MS (ESI, m/z): [M + 1]+ or NMR | IUPAC name |
|---|---|---|---|---|
| 53 | 3B, 58 | 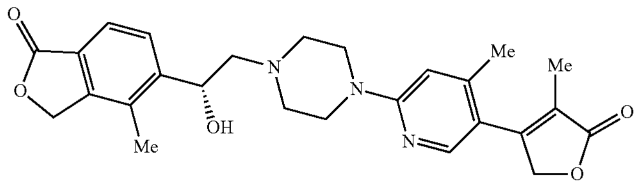 [SMILES: CC1=C(c2cnc(N3CCN(C[C@H](O)c4ccc5c(c4C)COC5=O)CC3)cc2C)COC1=O] | | (R)-5-(1-hydroxy-2-(4-(4-methyl-5-(4-methyl-5-oxo-2,5-dihydrofuran-3-yl)pyridin-2-yl)piperazin-1-yl)ethyl)-4-methylisobenzofuran-1(3H)-one |
| 54 | 3B, 64 | 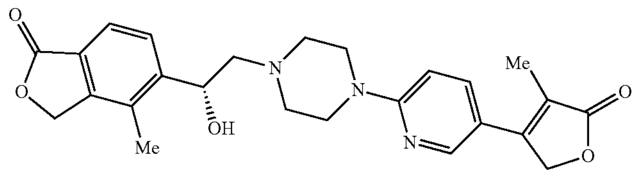 [SMILES: CC1=C(c2ccc(N3CCN(C[C@H](O)c4ccc5c(c4C)COC5=O)CC3)nc2)COC1=O] | 449 | (R)-5-(1-hydroxy-2-(4-(5-(4-methyl-5-oxo-2,5-dihydrofuran-3-yl)pyridin-2-yl)piperidin-1-yl)ethyl)-4-methylisobenzofuran-1(3H)-one |
| 55 | 3B, 61 | 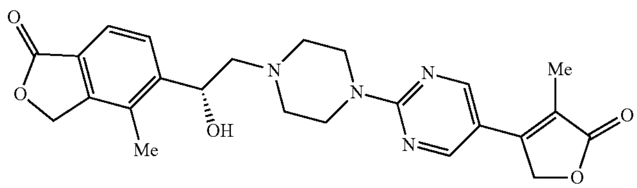 [SMILES: CC1=C(c2cnc(N3CCN(C[C@H](O)c4ccc5c(c4C)COC5=O)CC3)nc2)COC1=O] | 451 | (R)-5-(1-hydroxy-2-(4-(5-(4-methyl-5-oxo-2,5-dihydrofuran-3-yl)pyrimidin-2-yl)piperazin-1-yl)ethyl)-4-methylisobenzofuran-1(3H)-one |
| 56 | 3B, 60 | 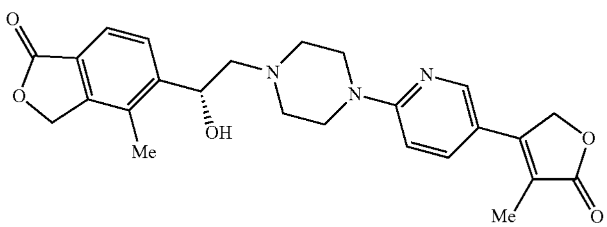 [SMILES: CC1=C(c2ccc(N3CCN(C[C@H](O)c4ccc5c(c4C)COC5=O)CC3)nc2)COC1=O] | 449 | (R)-5-(1-hydroxy-2-(4-(5-(4-methyl-5-oxo-2,5-dihydrofuran-3-yl)pyridin-2-yl)piperazin-1-yl)ethyl)-4-methylisobenzofuran-1(3H)-one |
| 57 | 3B, 62 | 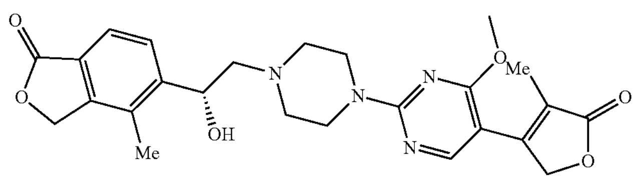 [SMILES: COc1nc(N2CCN(C[C@H](O)c3ccc4c(c3C)COC4=O)CC2)ncc1C1=C(C)C(=O)OC1] | 481 | (R)-5-(1-hydroxy-2-(4-(4-methoxy-5-(4-methyl-5-oxo-2,5-dihydrofuran-3-yl)pyrimidin-2-yl)piperazin-1-yl)ethyl)-4-methylisobenzofuran-1(3H)-one |
| 58 | 3B, 63 | 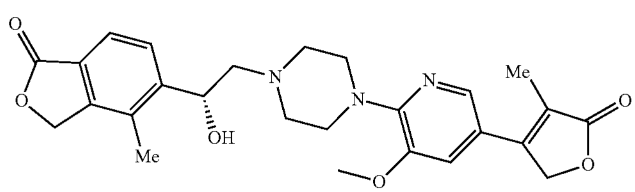 [SMILES: COc1cc(C2=C(C)C(=O)OC2)cnc1N1CCN(C[C@H](O)c2ccc3c(c2C)COC3=O)CC1] | 479 | (R)-5-(1-hydroxy-2-(4-(3-methoxy-5-(4-methyl-5-oxo-2,5-dihydrofuran-3-yl)pyridin-2-yl)piperazin-1-yl)ethyl)-4-methylisobenzofuran-1(3H)-one |
| 59 | 3B, 65 | 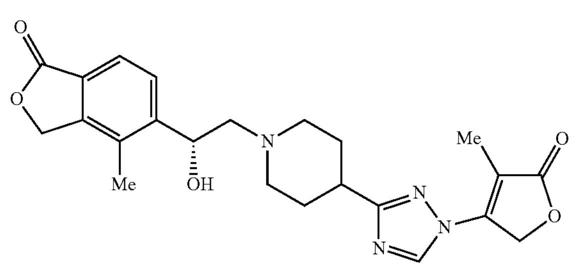 [SMILES: CC1=C(n2cnc(C3CCN(C[C@H](O)c4ccc5c(c4C)COC5=O)CC3)n2)COC1=O] | 439 | (R)-5-(1-hydroxy-2-(4-(1-(4-methyl-5-oxo-2,5-dihydrofuran-3-yl)-1H-1,2,4-triazol-3-yl)piperidin-1-yl)ethyl)-4-methylisobenzofuran-1(3H)-one |

| # | Intermediates | Structure | LC-MS (ESI, m/z): [M + 1]+ or NMR | IUPAC name |
|---|---|---|---|---|
| 60 | 5A, 65 | 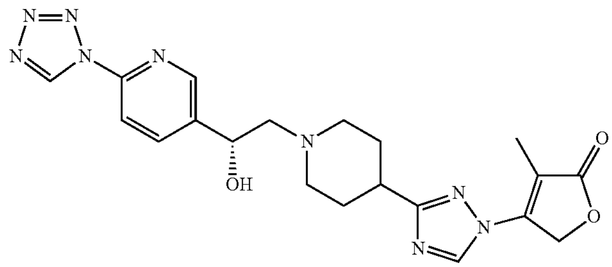 [SMILES: CC1=C(n2cnc(C3CCN(C[C@H](O)c4ccc(-n5cnnn5)nc4)CC3)n2)COC1=O] | 438 | (R)-4-(3-(1-(2-(6-(1H-tetrazol-1-yl)pyridin-3-yl)-2-hydroxyethyl)piperidin-4-yl)-1H-1,2,4-triazol-1-yl)-3-methylfuran-2(5H)-one |
| 61 | 5B, 65 | 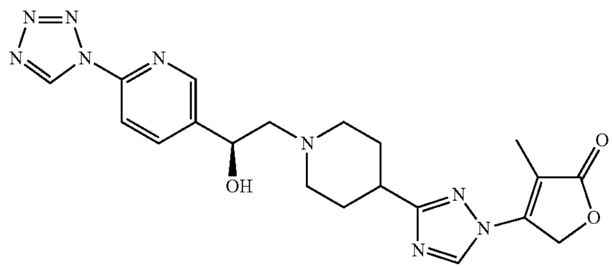 [SMILES: CC1=C(n2cnc(C3CCN(C[C@@H](O)c4ccc(-n5cnnn5)nc4)CC3)n2)COC1=O] | 438 | (S)-4-(3-(1-(2-(6-(1H-tetrazol-1-yl)pyridin-3-yl)-2-hydroxyethyl)piperidin-4-yl)-1H-1,2,4-triazol-1-yl)-3-methylfuran-2(5H)-one |

The following Thallium Flux Assay and/or the Electrophysiology Assays were performed on each of the final product compounds in the Examples unless otherwise noted.

Thallium Flux Assay

A Thallium Flux Assay was performed on the compounds of the Examples. This assay has been described previously; see, e.g., PCT Published Application WO 2013/062900.

Data collected for compounds in the Examples of the present invention using the Thallium Flux Assay are shown in Table 9 below. All of the tested final product compounds in the Examples (diastereomeric mixtures and individual diastereomers) had IC50 potencies less than 1 µM in the Thallium Flux Assay.

Electrophysiology Assay

Blocking of Kir1.1 (ROMK1) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 mL of Versene (Invitrogen 15040-066), a non-enzymatic cell dissociation reagent, for approximately 6 min at 37° C. and suspended in 10 mL of bath solution containing (in mM): 150 NaCl, 10 KCl, 2.7 $CaCl_2$, 0.5 $MgCl_2$, and 5 HEPES, at pH 7.4. After centrifugation, the cell pellet was resuspended in approximately 4.0 mL of bath solution and placed in the IonWorks instrument. The intracellular solution consisted of (in mM): 80 K gluconate, 40 KCl, 20 KF, 3.2 $MgCl_2$, 3 EGTA, and 5 Hepes, at pH 7.4. Electrical access to the cytoplasm was achieved by perforation in 0.13 mg/mL amphotericin B for 4 min. Amphotericin B (Sigma A-4888) was prepared as a 40 mg/mL solution in DMSO.

Voltage protocols and current recordings were performed using the IonWorks HT software/hardware system. Currents were sampled at 1 kHz. There was no correction for liquid junction potentials. The test pulse, consisting of a 100 ms (millisecond) step to 0 mV (millivolts) from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Although not required, a control compound is typically included to support that the assay is giving consistent results compared to previous measurements. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

Data collected for compounds in the Examples of the present invention using the Thallium Flux Assay and the Electrophysiology Assay are shown in Table 4 below. All of the tested final product compounds in the Examples (diastereomeric mixtures and individual diastereomers) had $IC_{50}$ potencies less than 1 µM in one or both of the Thallium Flux Assay and the Electrophysiology Assay.

TABLE in vitro potency

| EXAMPLE # | Thallium Flux IC$_{50}$ (M) | Electrophysiology IC$_{50}$ (M) |
|---|---|---|
| 1A | 0.0071 | 0.0041 |
| 1B | 0.0084 | 0.0019 |
| 2A | 0.042 | 0.038 |
| 2B | 0.24 | — |
| 3A | 0.14 | — |
| 3B | 0.11 | — |
| 3C | 0.024 | 0.011 |
| 3D | 0.021 | 0.0035 |
| 4A | 0.033 | 0.010 |
| 4B | 0.12 | — |
| 5A | 0.069 | — |
| 5B | 0.060 | 0.027 |
| 6A | 0.091 | — |
| 6B | 0.023 | — |
| 7A | 0.16 | — |
| 7B | 0.36 | — |
| 8 | 0.018 | 0.022 |
| 9A | 0.036 | — |
| 9B | 0.11 | — |
| 10A | 0.035 | 0.058 |
| 10B | 0.20 | — |
| 11 | 0.060 | — |
| 12 | 0.037 | 0.026 |
| 13A | 0.23 | — |
| 13B | 0.14 | — |
| 14 | 0.14 | — |
| 15 | 0.040 | 0.075 |
| 16 | 0.046 | 0.056 |
| 17 | 0.20 | — |
| 18A | 0.046 | — |
| 18B | 0.27 | — |
| 18C | 0.062 | 0.067 |
| 18D | 0.078 | — |
| 19A | 0.081 | — |
| 19B | 0.081 | 0.07 |
| 20A | 0.16 | — |
| 20B | 0.33 | — |
| 21A | 0.23 | — |
| 21B | 0.32 | — |
| 22A | 0.36 | — |
| 22B | 0.21 | — |
| 23A | 0.085 | — |
| 23B | 0.42 | — |
| 24A | 0.15 | — |
| 24B | 0.30 | — |
| 25A | 0.015 | — |
| 25B | 0.020 | 0.049 |
| 26A | 0.27 | — |
| 26B | 0.061 | — |
| 27A | 0.039 | 0.02 |
| 27B | 0.40 | — |
| 28 | 0.084 | — |
| 29A | 0.019 | 0.013 |
| 29B | 0.031 | 0.012 |
| 30A | 0.26 | — |
| 30B | 0.10 | — |
| 30C | 0.46 | — |
| 30D | 0.33 | — |
| 31 | 0.44 | — |
| 32A | 0.032 | 0.017 |
| 32B | 0.038 | 0.02 |
| 33A | 0.057 | 0.013 |
| 33B | 0.22 | — |
| 33C | 0.12 | — |
| 33D | 0.42 | — |
| 34 | 0.34 | — |
| 35 | 0.17 | — |
| 36A | 0.073 | 0.04 |
| 36B | 0.049 | — |
| 37A | 0.15 | — |
| 37B | 0.26 | — |
| 38A | 0.041 | — |
| 38B | 0.071 | — |
| 39 | 0.066 | 0.015 |
| 40 | 0.27 | — |
| 41A | 0.29 | — |
| 41B | 0.18 | — |
| 42A | 0.087 | 0.061 |
| 42B | 0.089 | 0.084 |
| 43 | 0.40 | — |
| 44 | 0.049 | — |
| 45 | 0.11 | — |
| 46 | 0.11 | — |
| 47 | 0.053 | 0.018 |
| 48 | 0.15 | — |
| 49 | 0.19 | — |
| 50 | 0.050 | — |
| 51 | 0.013 | 0.017 |
| 52A | 0.070 | 0.05 |
| 52B | 0.042 | — |
| 52C | 0.042 | — |
| 52D | 0.15 | — |
| 53 | 0.57 | — |
| 54 | 0.024 | — |
| 55 | 0.087 | 0.090 |
| 56 | 0.047 | 0.068 |
| 57 | 0.16 | — |
| 58 | 0.067 | — |
| 59 | 0.010 | 0.0026 |
| 60 | 0.16 | — |
| 61 | 0.53 | — |

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneuously hypertensive rats (SHR): Spontaneously hypertensive rats (SHR, male, 6 months, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. HCTZ (25 mg/kg/day, PO) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis.

The Spontaneously Hypertensive Rat Assay is well known and often used in the art as an experimental model simulating human hypertension (see, e.g., Lerman, L. O., et al., *J Lab Clin Med,* 2005; 146:160-173).

While the invention has been described with reference to certain particular embodiments thereof, numerous alternative embodiments will be apparent to those skilled in the art from the teachings described herein. The scope of the claims

What is claimed is:

1. A compound of the formula:

wherein X is N or CR$^b$;
Z is O or CH$_2$;

Ⓑ is

A is or a six-membered aromatic ring containing one or two nitrogen atoms which is optionally substituted with one or two substituents independently selected from the group consisting of tetrazolyl and C$_{1-3}$ alkyl;

R$^1$ is H, OH or O(C$_{1-3}$ alkyl);
R$^2$ is H or C$_{1-3}$ alkyl;
R$^4$ is H or C$_{1-3}$ alkyl;
R$^5$ is H or C$_{1-3}$ alkyl;
R$^6$ is H or C$_{1-3}$ alkyl;
R$^7$ is H, C$_{1-3}$ alkyl or O(C$_{1-3}$ alkyl);
R$^a$ is H or C$_{1-3}$ alkyl;
R$^b$ is H, OH, C$_{1-3}$ alkyl or (C=O)OC$_{1-3}$ alkyl;
R$^x$ is H, halo, C$_{1-3}$ alkyl or O(C$_{1-3}$ alkyl);
n is 0, 1 or 2;
- - - - is an optional bond;
or a pharmaceutically acceptable salt thereof.

2. The compound of claim 1 wherein

Ⓑ is or a pharmaceutically acceptable salt thereof.

3. The compound of claim 1 of the formula wherein

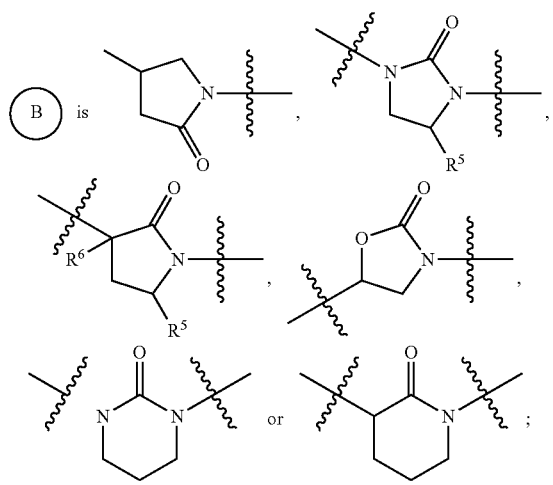

B is

A is

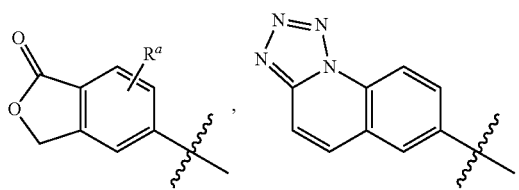

or a six-membered aromatic ring containing one or two nitrogen atoms which is optionally substituted with one or two substituents independently selected from the group consisting of tetrazolyl and $C_{1-3}$ alkyl;

$R^1$ is H, OH or $O(C_{1-3}$ alkyl);
$R^2$ is H or $C_{1-3}$ alkyl;
$R^4$ is H or $C_{1-3}$ alkyl;
$R^5$ is H or $C_{1-3}$ alkyl;
$R^6$ is H or $C_{1-3}$ alkyl;
$R^7$ is H or $O(C_{1-3}$ alkyl);
$R^a$ is H or $C_{1-3}$ alkyl;
$R^b$ is H, OH, $C_{1-3}$ alkyl or (C=O)$OC_{1-3}$ alkyl;
$R^x$ is H, halo, $C_{1-3}$ alkyl or $O(C_{1-3}$ alkyl);
or a pharmaceutically acceptable salt thereof.

4. The compound of claim 1 wherein A is

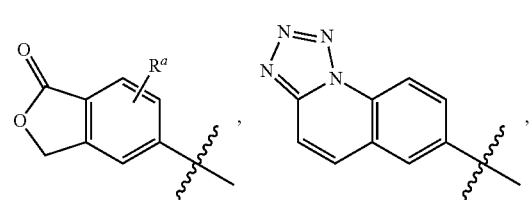

pyridinyl, pyrazinyl or pyridazinyl, wherein said pyridinyl, pyrazinyl or pyridazinyl are optionally substituted with one or two substituents independently selected from the group consisting of tetrazolyl and $C_{1-3}$ alkyl; or a pharmaceutically acceptable salt thereof.

5. The compound of claim 1 wherein A is

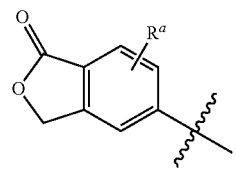

or a pharmaceutically acceptable salt thereof.

6. The compound of claim 1 wherein $R^1$ is OH, or a pharmaceutically acceptable salt thereof.

7. The compound of claim 1 wherein $R^2$ is H or methyl; or a pharmaceutically acceptable salt thereof.

8. The compound of claim 1 wherein $R^4$ is H or methyl; or a pharmaceutically acceptable salt thereof.

9. The compound of claim 1 selected from:
3-(1-((R)-2-hydroxy-2-(4-methyl-1-oxo-1,3-dihydroisobenzofuran-5-yl)ethyl)piperidin-4-yl)-1-(4-methyl-5-oxo-2, 5-dihydrofuran-3-yl)pyrrolidin-2-one;
1-((3S,4S)-1-((R)-2-(6-(1H-tetrazol-1-yl)pyridin-3-yl)-2-hydroxyethyl)-3-fluoropiperidin-4-yl)-3-(4-methyl-5-oxo-2, 5-dihydrofuran-3-yl)imidazolidin-2-one;
1-((3R,4R)-1-((R)-2-(6-(1H-tetrazol-1-yl)pyridin-3-yl)-2-hydroxyethyl)-3-fluoropiperidin-4-yl)-3-(4-methyl-5-oxo-2, 5-dihydrofuran-3-yl)imidazolidin-2-one,
3-(1-((R)-2-(6-(1H-tetrazol-1-yl)pyridin-3-yl)-2-hydroxyethyl)piperidin-4-yl)-1-(4-methyl-5-oxo-2,5-dihydrofuran-3-yl)pyrrolidin-2-one;
3-(1-((S)-2-(6-(1H-tetrazol-1-yl)pyridin-3-yl)-2-hydroxyethyl)piperidin-4-yl)-1-(4-methyl-5-oxo-2,5-dihydrofuran-3-yl)pyrrolidin-2-one;
3-(1-((R)-2-(6-(1H-tetrazol-1-yl)pyridin-3-yl)-2-hydroxyethyl)piperidin-4-yl)-1-(4-methyl-5-oxo-2,5-dihydrofuran-3-yl)pyrrolidin-2-one;
3-(1-((S)-2-(6-(1H-tetrazol-1-yl)pyridin-3-yl)-2-hydroxyethyl)piperidin-4-yl)-1-(4-methyl-5-oxo-2,5-dihydrofuran-3-yl)pyrrolidin-2-one;
(R)-1-(1-(2-(6-(1H-tetrazol-1-yl)pyridin-3-yl)-2-hydroxyethyl)piperidin-4-yl)-3-(4-methyl-5-oxo-2,5-dihydrofuran-3-yl)imidazolidin-2-one;
(S)-1-(1-(2-(6-(1H-tetrazol-1-yl)pyridin-3-yl)-2-hydroxyethyl)piperidin-4-yl)-3-(4-methyl-5-oxo-2,5-dihydrofuran-3-yl)imidazolidin-2-one;
4-(3-((R)-2-hydroxy-2-(4-methyl-1-oxo-1,3-dihydroisobenzofuran-5-yl)ethyl)-3-azabicyclo[3.1.0]hexan-6-yl)-1-(5-oxo-2,5-dihydrofuran-3-yl)pyrrolidin-2-one;
4-(3-((R)-2-hydroxy-2-(4-methyl-1-oxo-1,3-dihydroisobenzofuran-5-yl)ethyl)-3-azabicyclo[3.1.0]hexan-6-yl)-1-(4-methyl-5-oxo-2,5-dihydrofuran-3-yl)pyrrolidin-2-one;
4-(3-((R)-2-(6-(1H-tetrazol-1-yl)pyridin-3-yl)-2-hydroxyethyl)-3-azabicyclo[3.1.0]hexan-6-yl)-1-(4-methyl-5-oxo-2, 5-dihydrofuran-3-yl)pyrrolidin-2-one;
1-(3-((R)-2-hydroxy-2-(4-methyl-1-oxo-1,3-dihydroisobenzofuran-5-yl)ethyl)-3-azabicyclo[3.1.0]hexan-6-yl)-3-(4-methyl-5-oxo-2,5-dihydrofuran-3-yl)imidazolidin-2-one;
1-(3-((R)-2-(6-(1H-tetrazol-1-yl)pyridin-3-yl)-2-hydroxyethyl)-3-azabicyclo[3.1.0]hexan-6-yl)-3-(4-methyl-5-oxo-2, 5-dihydrofuran-3-yl)imidazolidin-2-one;
1-(3-((S)-2-(6-(1H-tetrazol-1-yl)pyridin-3-yl)-2-hydroxyethyl)-3-azabicyclo[3.1.0]hexan-6-yl)-3-(4-methyl-5-oxo-2, 5-dihydrofuran-3-yl)imidazolidin-2-one;

1-(3-(2-hydroxy-2-(2-methyl-6-(1H-tetrazol-1-yl)pyridin-3-yl)ethyl)-3-azabicyclo[3.1.0]hexan-6-yl)-3-(4-methyl-5-oxo-2,5-dihydrofuran-3-yl)imidazolidin-2-one;

1-(3-((R)-2-hydroxy-2-(4-methyl-1-oxo-1,3-dihydroisobenzofuran-5-yl)ethyl)-3-azabicyclo[3.1.0]hexan-6-yl)-3-(3-oxocyclopent-1-en-1-yl)imidazolidin-2-one;

(R)-1-(1-(2-hydroxy-2-(4-methyl-1-oxo-1,3-dihydroisobenzofuran-5-yl)ethyl)piperidin-4-yl)-3-(4-methyl-5-oxo-2, 5-dihydrofuran-3-yl)imidazolidin-2-one;

1-(1-(2-hydroxy-2-(2-methyl-6-(1H-tetrazol-1-yl)pyridin-3-yl)ethyl)pyrrolidin-3-yl)-3-(4-methyl-5-oxo-2,5-dihydrofuran-3-yl)imidazolidin-2-one;

1-(1-((R)-2-hydroxy-2-(4-methyl-1-oxo-1,3-dihydroisobenzofuran-5-yl)ethyl)pyrrolidin-3-yl)-3-(4-methyl-5-oxo-2, 5-dihydrofuran-3-yl)imidazolidin-2-one;

(R)-1-(1-(2-hydroxy-2-(4-methyl-1-oxo-1,3-dihydroisobenzofuran-5-yl)ethyl)piperidin-4-yl)-3-(4-methyl-5-oxo-2, 5-dihydrofuran-3-yl)tetrahydropyrimidin-2(1H)-one;

1-(1-(2-hydroxy-2-(2-methyl-6-(1H-tetrazol-1-yl)pyridin-3-yl)ethyl)piperidin-4-yl)-3-(4-methyl-5-oxo-2,5-dihydrofuran-3-yl)tetrahydropyrimidin-2(1H)-one;

1-(3-fluoro-1-(2-hydroxy-2-(2-methyl-6-(1H-tetrazol-1-yl)pyridin-3-yl)ethyl)piperidin-4-yl)-3-(4-methyl-5-oxo-2, 5-dihydrofuran-3-yl)imidazolidin-2-one;

1-(3-fluoro-1-((R)-2-hydroxy-2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one;

1-(3-fluoro-1-((R)-2-hydroxy-2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one;

1-(1-((R)-2-hydroxy-2-(4-methyl-1-oxo-1,3-dihydroisobenzofuran-5-yl)ethyl)-3-methoxypiperidin-4-yl)-3-(4-methyl-5-oxo-2, 5-dihydrofuran-3-yl)imidazolidin-2-one;

1-(1-(2-(5-(1H-tetrazol-1-yl)pyrazin-2-yl)-2-hydroxyethyl)-3-methoxypiperidin-4-yl)-3-(4-methyl-5-oxo-2, 5-dihydrofuran-3-yl)imidazolidin-2-one;

1-(1-(2-(5-(1H-tetrazol-1-yl)pyrazin-2-yl)-2-hydroxyethyl)-3-fluoropiperidin-4-yl)-3-(4-methyl-5-oxo-2,5-dihydrofuran-3-yl)imidazolidin-2-one;

1-(1-(2-(5-(1H-tetrazol-1-yl)pyrazin-2-yl)-2-hydroxyethyl)piperidin-4-yl)-3-(4-methyl-5-oxo-2,5-dihydrofuran-3-yl)tetrahydropyrimidin-2(1H)-one;

1-(1-(2-(6-(1H-tetrazol-1-yl)pyridazin-3-yl)-2-hydroxyethyl)piperidin-4-yl)-3-(4-methyl-5-oxo-2,5-dihydrofuran-3-yl)imidazolidin-2-one;

1-(1-(2-(5-(1H-tetrazol-1-yl)pyrazin-2-yl)-2-hydroxyethyl)piperidin-4-yl)-3-(4-methyl-5-oxo-2,5-dihydrofuran-3-yl)imidazolidin-2-one;

3-(4-((R)-2-hydroxy-2-(4-methyl-1-oxo-1,3-dihydroisobenzofuran-5-yl)ethyl)piperazin-1-yl)-1-(4-methyl-5-oxo-2,5-dihydrofuran-3-yl)pyrrolidin-2-one;

3-(4-(2-hydroxy-2-(2-methyl-6-(1H-tetrazol-1-yl)pyridin-3-yl)ethyl)piperazin-1-yl)-1-(4-methyl-5-oxo-2,5-dihydrofuran-3-yl)pyrrolidin-2-one;

(R)-1-(1-(2-(6-(1H-tetrazol-1-yl)pyridin-3-yl)-2-hydroxyethyl)piperidin-4-yl)-3-(4-methyl-5-oxo-2,5-dihydrofuran-3-yl)tetrahydropyrimidin-2(1H)-one;

(S)-1-(1-(2-(6-(1H-tetrazol-1-yl)pyridin-3-yl)-2-hydroxyethyl)piperidin-4-yl)-3-(4-methyl-5-oxo-2,5-dihydrofuran-3-yl)tetrahydropyrimidin-2(1H)-one;

3-(1-(2-(5-(1H-tetrazol-1-yl)pyridin-2-yl)-2-hydroxyethyl)piperidin-4-yl)-1-(4-methyl-5-oxo-2,5-dihydrofuran-3-yl)pyrrolidin-2-one;

1-(1-((R)-2-hydroxy-2-(4-methyl-1-oxo-1,3-dihydroisobenzofuran-5-yl)ethyl)piperidin-4-yl)-4-methyl-3-(4-methyl-5-oxo-2,5-dihydrofuran-3-yl)imidazolidin-2-one;

1-(1-((R)-2-(6-(1H-tetrazol-1-yl)pyridin-3-yl)-2-hydroxyethyl)piperidin-4-yl)-4-methyl-3-(4-methyl-5-oxo-2, 5-dihydrofuran-3-yl)imidazolidin-2-one;

1-(1-((S)-2-(6-(1H-tetrazol-1-yl)pyridin-3-yl)-2-hydroxyethyl)piperidin-4-yl)-4-methyl-3-(4-methyl-5-oxo-2,5-dihydrofuran-3-yl)imidazolidin-2-one;

3-(1-((R)-2-(6-(1H-tetrazol-1-yl)pyridin-3-yl)-2-hydroxyethyl)-4-hydroxypiperidin-4-yl)-1-(4-methyl-5-oxo-2, 5-dihydrofuran-3-yl)pyrrolidin-2-one;

1-(1-((R)-2-hydroxy-2-(4-methyl-1-oxo-1,3-dihydroisobenzofuran-5-yl)ethyl)piperidin-4-yl)-4-methyl-3-(5-oxo-2,5-dihydrofuran-3-yl)imidazolidin-2-one;

1-(1-((R)-2-(6-(1H-tetrazol-1-yl)pyridin-3-yl)-2-hydroxyethyl)piperidin-4-yl)-4-methyl-3-(5-oxo-2,5-dihydrofuran-3-yl)imidazolidin-2-one;

1-(1-((R)-2-(6-(1H-tetrazol-1-yl)pyridin-3-yl)-2-hydroxyethyl)piperidin-4-yl)-4-methyl-3-(5-oxo-2,5-dihydrofuran-3-yl)imidazolidin-2-one;

1-(1-((S)-2-(6-(1H-tetrazol-1-yl)pyridin-3-yl)-2-hydroxyethyl)piperidin-4-yl)-4-methyl-3-(5-oxo-2,5-dihydrofuran-3-yl)imidazolidin-2-one;

ethyl 1-((R)-2-(6-(1H-tetrazol-1-yl)pyridin-3-yl)-2-hydroxyethyl)-4-(3-(4-methyl-5-oxo-2, 5-dihydrofuran-3-yl)-2-oxooxazolidin-5-yl)piperidine-4-carboxylate;

ethyl 1-((R)-2-hydroxy-2-(4-methyl-1-oxo-1,3-dihydroisobenzofuran-5-yl)ethyl)-4-(3-(4-methyl-5-oxo-2, 5-dihydrofuran-3-yl)-2-oxooxazolidin-5-yl)piperidine-4-carboxylate;

3-(4-hydroxy-1-((R)-2-hydroxy-2-(4-methyl-1-oxo-1,3-dihydroisobenzofuran-5-yl)ethyl)piperidin-4-yl)-1-(4-methyl-5-oxo-2, 5-dihydrofuran-3-yl)pyrrolidin-2-one;

1'-((R)-2-hydroxy-2-(4-methyl-1-oxo-1,3-dihydroisobenzofuran-5-yl)ethyl)-1-(4-methyl-5-oxo-2,5-dihydrofuran-3-yl)-[3,4'-bipiperidin]-2-one;

4-(1-((R)-2-hydroxy-2-(4-methyl-1-oxo-1,3-dihydroisobenzofuran-5-yl)ethyl)piperidin-4-yl)-1-(4-methyl-5-oxo-2,5-dihydrofuran-3-yl)pyrrolidin-2-one;

3-(1-((R)-2-hydroxy-2-(4-methyl-1-oxo-1,3-dihydroisobenzofuran-5-yl)ethyl)piperidin-4-yl)-3-methyl-1-(4-methyl-5-oxo-2,5-dihydrofuran-3-yl)pyrrolidin-2-one;

3-(1-((R)-2-(6-(1H-tetrazol-1-yl)pyridin-3-yl)-2-hydroxyethyl)piperidin-4-yl)-3-methyl-1-(4-methyl-5-oxo-2, 5-dihydrofuran-3-yl)pyrrolidin-2-one;

1-(1-((R)-2-(6-(1H-tetrazol-1-yl)pyridin-3-yl)-2-hydroxyethyl)piperidin-4-yl)-4-ethyl-3-(4-methyl-5-oxo-2,5-dihydrofuran-3-yl)imidazolidin-2-one;

4-ethyl-1-(1-((R)-2-hydroxy-2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one;

1-(1-(2-hydroxy-2-(tetrazolo[1,5-a]quinolin-7-yl)ethyl)piperidin-4-yl)-3-(4-methyl-5-oxo-2,5-dihydrofuran-3-yl)imidazolidin-2-one;

1-(1-(2-(5-(1H-Tetrazol-1-yl)pyridin-2-yl)ethyl)piperidin-4-yl)-3-(4-methyl-5-oxo-2,5-dihydrofuran-3-yl)imidazolidin-2-one;

1-(1-(2-(6-(1H-tetrazol-1-yl)pyridazin-3-yl)ethyl)piperidin-4-yl)-3-(4-methyl-5-oxo-2,5-dihydrofuran-3-yl)imidazolidin-2-one;
1-(1-(2-(5-(1H-tetrazol-1-yl)pyrazin-2-yl)ethyl)piperidin-4-yl)-3-(4-methyl-5-oxo-2, 5-dihydrofuran-3-yl)imidazolidin-2-one;
(R)-1-(1-(2-methoxy-2-(4-methyl-1-oxo-1,3-dihydroisobenzofuran-5-yl)ethyl)piperidin-4-yl)-3-(4-methyl-5-oxo-2, 5-dihydrofuran-3-yl)imidazolidin-2-one;
(R)-1-(1-(2-ethoxy-2-(4-methyl-1-oxo-1,3-dihydroisobenzofuran-5-yl)ethyl)piperidin-4-yl)-3-(4-methyl-5-oxo-2, 5-dihydrofuran-3-yl)imidazolidin-2-one;
(R)-1-(1-(2-(6-(1H-tetrazol-1-yl)pyridin-3-yl)-2-methoxyethyl)piperidin-4-yl)-3-(4-methyl-5-oxo-2,5-dihydrofuran-3-yl)imidazolidin-2-one;
1-(1-(2-(6-(1H-Tetrazol-1-yl)pyridin-3-yl)ethyl)piperidin-4-yl)-3-(4-methyl-5-oxo-2,5-dihydrofuran-3-yl)imidazolidin-2-one;
1-(1-(2-(4-methyl-1-oxo-1,3-dihydroisobenzofuran-5-yl)ethyl)piperidin-4-yl)-3-(4-methyl-5-oxo-2,5-dihydrofuran-3-yl)imidazolidin-2-one;
1-(1-(1-hydroxy-1-(4-methyl-1-oxo-1,3-dihydroisobenzofuran-5-yl)propan-2-yl)piperidin-4-yl)-3-(4-methyl-5-oxo-2, 5-dihydrofuran-3-yl)imidazolidin-2-one;
1-(1-(((1R,2R)-1-hydroxy-1-(4-methyl-1-oxo-1,3-dihydroisobenzofuran-5-yl)propan-2-yl)piperidin-4-yl)-3-(4-methyl-5-oxo-2, 5-dihydrofuran-3-yl)imidazolidin-2-one;
1-(1-(((1R,2S)-1-hydroxy-1-(4-methyl-1-oxo-1,3-dihydroisobenzofuran-5-yl)propan-2-yl)piperidin-4-yl)-3-(4-methyl-5-oxo-2, 5-dihydrofuran-3-yl)imidazolidin-2-one;
1-(1-(((1S,2R)-1-hydroxy-1-(4-methyl-1-oxo-1,3-dihydroisobenzofuran-5-yl)propan-2-yl)piperidin-4-yl)-3-(4-methyl-5-oxo-2, 5-dihydrofuran-3-yl)imidazolidin-2-one;
1-(1-(((1S,2S)-1-hydroxy-1-(4-methyl-1-oxo-1,3-dihydroisobenzofuran-5-yl)propan-2-yl)piperidin-4-yl)-3-(4-methyl-5-oxo-2, 5-dihydrofuran-3-yl)imidazolidin-2-one;
(R)-5-(1-hydroxy-2-(4-(4-methyl-5-(4-methyl-5-oxo-2,5-dihydrofuran-3-yl)pyridin-2-yl)piperazin-1-yl)ethyl)-4-methylisobenzofuran-1 (3H)-one;
(R)-5-(1-hydroxy-2-(4-(5-(4-methyl-5-oxo-2, 5-dihydrofuran-3-yl)pyridin-2-yl)piperidin-1-yl)ethyl)-4-methylisobenzofuran-1 (3H)-one;
(R)-5-(1-hydroxy-2-(4-(5-(4-methyl-5-oxo-2,5-dihydrofuran-3-yl)pyrimidin-2-yl)piperazin-1-yl)ethyl)-4-methylisobenzofuran-1 (3H)-one;
(R)-5-(1-hydroxy-2-(4-(5-(4-methyl-5-oxo-2,5-dihydrofuran-3-yl)pyridin-2-yl)piperazin-1-yl)ethyl)-4-methylisobenzofuran-1 (3H)-one;
(R)-5-(1-hydroxy-2-(4-(4-methoxy-5-(4-methyl-5-oxo-2, 5-dihydrofuran-3-yl)pyrimidin-2-yl)piperazin-1-yl)ethyl)-4-methylisobenzofuran-1 (3H)-one;
(R)-5-(1-hydroxy-2-(4-(3-methoxy-5-(4-methyl-5-oxo-2, 5-dihydrofuran-3-yl)pyridin-2-yl)piperazin-1-yl)ethyl)-4-methylisobenzofuran-1 (3H)-one;
(R)-5-(1-hydroxy-2-(4-(1-(4-methyl-5-oxo-2,5-dihydrofuran-3-yl)-1H-1,2,4-triazol-3-yl)piperidin-1-yl)ethyl)-4-methylisobenzofuran-1 (3H)-one;
(R)-4-(3-(1-(2-(6-(1H-tetrazol-1-yl)pyridin-3-yl)-2-hydroxyethyl)piperidin-4-yl)-1H-1,2,4-triazol-1-yl)-3-methylfuran-2(5H)-one
(S)-4-(3-(1-(2-(6-(1H-tetrazol-1-yl)pyridin-3-yl)-2-hydroxyethyl)piperidin-4-yl)-1H-1,2,4-triazol-1-yl)-3-methylfuran-2(5H)-one;

or a pharmaceutically acceptable salt thereof.

10. A pharmaceutical composition comprising a compound of claim 1 or a pharmaceutically acceptable salt thereof and a pharmaceutically acceptable carrier.

11. The pharmaceutical composition of claim 10 further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, trandolapril, amiloride, spironolactone, epleranone, triamterene, riociguat or vericiguat, or a pro-drug thereof, or a pharmaceutically acceptable salt of any of the foregoing.

12. A method for inhibiting ROMK comprising administering a compound of claim 1 or a pharmaceutically acceptable salt thereof in a ROMK-inhibitory effective amount to a patient in need thereof.

13. A method for causing dieresis, natriuresis or both, comprising administering a compound of claim 1 or a pharmaceutically acceptable salt thereof in a therapeutically effective amount to a patient in need thereof.

14. A method for the treatment of one or more disorders selected from hypertension, acute heart failure, chronic heart failure, pulmonary arterial hypertension, cardiovascular disease, diabetes, endothelial dysfunction, diastolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, nephrotic syndrome, acute kidney insufficiency, chronic kidney disease, hypercalcemia, Dent's disease, Meniere's disease, or edematous states comprising administering a compound of claim 1 or a pharmaceutically acceptable salt thereof in a therapeutically effective amount to a patient in need thereof.

* * * * *